United States Patent
Stupp et al.

(10) Patent No.: US 12,122,811 B2
(45) Date of Patent: Oct. 22, 2024

(54) BDNF MIMETIC PEPTIDE AMPHIPHILES

(71) Applicant: Northwestern University, Evanston, IL (US)

(72) Inventors: Samuel I. Stupp, Chicago, IL (US); Alexandra N. Kolberg, Chicago, IL (US); Zaida Alvarez, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/045,728

(22) PCT Filed: Apr. 5, 2019

(86) PCT No.: PCT/US2019/026077
§ 371 (c)(1),
(2) Date: Oct. 6, 2020

(87) PCT Pub. No.: WO2019/195741
PCT Pub. Date: Oct. 10, 2019

(65) Prior Publication Data
US 2021/0163556 A1 Jun. 3, 2021

Related U.S. Application Data

(60) Provisional application No. 62/653,939, filed on Apr. 6, 2018.

(51) Int. Cl.
*C07K 14/475* (2006.01)
*C07K 7/64* (2006.01)

(52) U.S. Cl.
CPC .............. *C07K 14/475* (2013.01); *C07K 7/64* (2013.01)

(58) Field of Classification Search
None
See application file for complete search history.

(56) References Cited

U.S. PATENT DOCUMENTS

| | | |
|---|---|---|
| 6,890,654 B2 | 5/2005 | Stupp et al. |
| 7,371,719 B2 | 5/2008 | Stupp et al. |
| 7,390,526 B2 | 6/2008 | Stupp et al. |
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 7,838,491 B2 | 11/2010 | Stupp et al. |
| 7,851,445 B2 | 12/2010 | Stupp et al. |
| 8,063,014 B2 | 11/2011 | Stupp et al. |
| 8,080,262 B2 | 12/2011 | Lee et al. |
| 8,114,834 B2 | 2/2012 | Hsu et al. |
| 8,114,835 B2 | 2/2012 | Mata et al. |
| 8,124,583 B2 | 2/2012 | Stupp et al. |
| 8,138,140 B2 | 3/2012 | Stupp et al. |
| 8,450,271 B2 | 5/2013 | Shah et al. |
| 8,512,693 B2 | 8/2013 | Capito et al. |
| 2003/0191278 A1 | 10/2003 | Peng et al. |
| 2006/0247165 A1* | 11/2006 | Stupp .................. A61K 49/0021 424/85.2 |
| 2012/0264912 A1 | 10/2012 | Stupp et al. |
| 2014/0248257 A1 | 9/2014 | Tymianski |
| 2015/0182596 A1* | 7/2015 | Lee .......................... A61K 38/16 435/320.1 |
| 2016/0354480 A1 | 12/2016 | Jacquot et al. |
| 2017/0368200 A1 | 12/2017 | Bancel et al. |

FOREIGN PATENT DOCUMENTS

WO   WO 2016/168302 A1   10/2016

OTHER PUBLICATIONS

Fletcher et al. (J Biol Chem. Nov. 28, 2008; 283(48): 33375-33383) (Year: 2008).*
Fletcher et al., Bioorganic & Medicinal Chemistry 17 (2009) 2695-2702 (Year: 2009).*
Guichard et al., Proc. Nati. Acad. Sci. USA vol. 91, pp. 9765-9769 (Year: 1994).*
International Search Report and Written Opinion for PCT/US2019/026077. Mailed Jul. 1, 2019. 15 pages.
Barde et al., Purification of a new neurotrophic factor from mammalian brain. EMBO J. 1982;1(5):549-53.
Basso et al., Basso Mouse Scale for locomotion detects differences in recovery after spinal cord injury in five common mouse strains. J Neurotrauma. May 2006;23(5):635-59.
Behar et al., Neurotrophins stimulate chemotaxis of embryonic cortical neurons. Eur J Neurosci. Dec. 1997;9(12):2561-70.
Berns et al., A tenascin-C mimetic peptide amphiphile nanofiber gel promotes neurite outgrowth and cell migration of neurosphere-derived cells. Acta Biomater. Jun. 2016;37:50-8.
Blesch et al., Transient growth factor delivery sustains regenerated axons after spinal cord injury. J Neurosci. Sep. 26, 2007;27(39):10535-45.
Brewer. Serum-free B27/neurobasal medium supports differentiated growth of neurons from the striatum, substantia nigra, septum, cerebral cortex, cerebellum, and dentate gyrus. J Neurosci Res. Dec. 1995;42(5):674-83.
Burkhalter et al., Brain-derived neurotrophic factor stimulates energy metabolism in developing cortical neurons. J Neurosci. Sep. 10, 2003;23(23):8212-20.
Chao. Neurotrophins and their receptors: a convergence point for many signalling pathways. Nat Rev Neurosci. Apr. 2003;4(4):299-309.

(Continued)

*Primary Examiner* — Sergio Coffa
(74) *Attorney, Agent, or Firm* — Casimir Jones, S.C.; Rikki A. Hullinger

(57) ABSTRACT

Provided herein are peptide amphiphiles (PAs) and supramolecular PA nanostructures that mimic brain derived neurotrophic factor (BDNF), a growth factor that induces neuronal survival, maturation, and increased electrical activity. In particular, injectable biomaterials comprising BDNF mimetic PAs are provided, as well as methods of using BDNF mimetic PAs for the treatment or prevention of neurological injuries, diseases, and disorders.

12 Claims, 58 Drawing Sheets

Specification includes a Sequence Listing.

(56) References Cited

OTHER PUBLICATIONS

Chiaramello et al., BDNF/ TrkB interaction regulates migration of SVZ precursor cells via PI3-K and MAP-K signalling pathways. Eur J Neurosci. Oct. 2007;26(7):1780-90.
Cohen-Cory et al., Brain-derived neurotrophic factor and the development of structural neuronal connectivity. Dev Neurobiol. Apr. 2010;70(5):271-88.
Connor et al., Brain-derived neurotrophic factor is reduced in Alzheimer's disease. Brain Res Mol Brain Res. Oct. 3, 1997;49(1-2):71-81.
Dehmelt et al., The MAP2/Tau family of microtubule-associated proteins. Genome Biol. 2005;6(1):204.
Discher et al., Growth factors, matrices, and forces combine and control stem cells. Science. Jun. 26, 2009;324(5935):1673-7.
Eide et al., Neurotrophins and their receptors—current concepts and implications for neurologic disease. Exp Neurol. Jun. 1993;121(2):200-14.
Figurov et al., Regulation of synaptic responses to high-frequency stimulation and LTP by neurotrophins in the hippocampus. Nature. Jun. 20, 1996;381(6584):706-9.
Fletcher et al., Modified low molecular weight cyclic peptides as mimetics of BDNF with improved potency, proteolytic stability and transmembrane passage in vitro. Bioorg Med Chem. Apr. 1, 2009;17(7):2695-702.
Fletcher et al., Design of a conformationally defined and proteolytically stable circular mimetic of brain-derived neurotrophic factor. J Biol Chem. Nov. 28, 2008;283(48):33375-83.
Fletcher et al., Novel monocyclic and bicyclic loop mimetics of brain-derived neurotrophic factor. J Pept Sci. Aug. 2006;12(8):515-24.
Gentry et al., The p75 neurotrophin receptor: multiple interactors and numerous functions. Prog Brain Res. 2004;146:25-39.
Goldberger et al., Electrostatic control of bioactivity. Angew Chem Int Ed Engl. Jul. 4, 2011;50(28):6292-5.
Gonsalvez et al., A Brain-Derived Neurotrophic Factor-Based p75 NTR Peptide Mimetic Ameliorates Experimental Autoimmune Neuritis Induced Axonal Pathology and Demyelination. eNeuro. Jul. 4, 2017;4(3):ENEURO.0142-17.2017.
Gorski et al., Brain-derived neurotrophic factor is required for the maintenance of cortical dendrites. J Neurosci. Jul. 30, 2003;23(17):6856-65.
Gottschalk et al., Signaling mechanisms mediating BDNF modulation of synaptic plasticity in the hippocampus. Learn Mem. May-Jun. 1999;6(3):243-56.
Hallböök. Evolution of the vertebrate neurotrophin and Trk receptor gene families. Curr Opin Neurobiol. Oct. 1999;9(5):616-21.
Hartgerink et al., Self-assembly and mineralization of peptide-amphiphile nanofibers. Science. Nov. 23, 2001;294(5547):1684-8.
Hu et al., BDNF stabilizes synapses and maintains the structural complexity of optic axons in vivo. Development. Oct. 2005;132(19):4285-98.
Huang et al., Trk receptors: roles in neuronal signal transduction. Annu Rev Biochem. 2003;72:609-42.
Huang et al., Neurotrophins: roles in neuronal development and function. Annu Rev Neurosci. 2001;24:677-736.
Ibáñez. Neurotrophic factors: from structure-function studies to designing effective therapeutics. Trends Biotechnol. Jun. 1995;13(6):217-27.
Israelachvili Intermolecular and surface forces; 2nd ed.; Academic: London San Diego, 1992. TOC only. 2 pages.
Ji et al., Acute and gradual increases in BDNF concentration elicit distinct signaling and functions in neurons. Nat Neurosci. Mar. 2010;13(3):302-9.
Ji et al., Cyclic AMP controls BDNF-induced TrkB phosphorylation and dendritic spine formation in mature hippocampal neurons. Nat Neurosci. Feb. 2005;8(2):164-72.
Kang et al., Long-lasting neurotrophin-induced enhancement of synaptic transmission in the adult hippocampus. Science. Mar. 17, 1995;267(5204):1658-62.

Lu et al., BDNF-based synaptic repair as a disease-modifying strategy for neurodegenerative diseases. Nat Rev Neurosci. Jun. 2013;14(6):401-16.
Lu et al., BDNF-expressing marrow stromal cells support extensive axonal growth at sites of spinal cord injury. Exp Neurol. Feb. 2005;191(2):344-60.
Martínez et al., TrkB and TrkC signaling are required for maturation and synaptogenesis of hippocampal connections. J Neurosci. Sep. 15, 1998;18(18):7336-50.
Mayo et al., A recipe for designing water-soluble, beta-sheet-forming peptides. Protein Sci. Jul. 1996;5(7):1301-15.
Meyer et al., Balance and stability of synaptic structures during synaptic plasticity. Neuron. Apr. 16, 2014;82(2):430-43.
Mogi et al., Brain-derived growth factor and nerve growth factor concentrations are decreased in the substantia nigra in Parkinson's disease. Neurosci Lett. Jul. 23, 1999;270(1):45-8.
Nagahara et al., Neuroprotective effects of brain-derived neurotrophic factor in rodent and primate models of Alzheimer's disease. Nat Med. Mar. 2009;15(3):331-7.
Nagahara et al., Potential therapeutic uses of BDNF in neurological and psychiatric disorders. Nat Rev Drug Discov. Mar. 2011;10(3):209-19.
Ochs et al., A phase I/II trial of recombinant methionyl human brain derived neurotrophic factor administered by intrathecal infusion to patients with amyotrophic lateral sclerosis. Amyotroph Lateral Scler Other Motor Neuron Disord. Jun. 2000;1(3):201-6.
Okada et al., Differential effects of phospholipase inhibitors in long-term potentiation in the rat hippocampal mossy fiber synapses and Schaffer/commissural synapses. Neurosci Lett. May 22, 1989;100(1-3):141-6.
Olbrich et al., Surfaces modified with covalently-immobilized adhesive peptides affect fibroblast population motility. Biomaterials. Apr. 1996;17(8):759-64.
O'Leary et al., Design of potent peptide mimetics of brain-derived neurotrophic factor. J Biol Chem. Jul. 11, 2003;278(28):25738-44.
O'Leary et al., Structure-activity relationships of conformationally constrained peptide analogues of loop 2 of brain-derived neurotrophic factor. J Neurochem. Apr. 1998;70(4):1712-21.
Pan et al., β1-Integrin and integrin linked kinase regulate astrocytic differentiation of neural stem cells. PLoS One . Aug. 6, 2014;9(8):e104335. 12 pages.
Pardridge. Neurotrophins, neuroprotection and the blood-brain barrier. Curr Opin Investig Drugs. Dec. 2002;3(12):1753-7.
Park et al., Neurotrophin regulation of neural circuit development and function. Nat Rev Neurosci. Jan. 2013;14(1):7-23.
Pérez et al., Mimicking the Bioactivity of Fibroblast Growth Factor-2 Using Supramolecular Nanoribbons. ACS Biomater Sci Eng. Sep. 11, 2017;3(9):2166-2175.
Rauskolb et al., Global deprivation of brain-derived neurotrophic factor in the CNS reveals an area-specific requirement for dendritic growth. J Neurosci. Feb. 3, 2010;30(5):1739-49.
Rodriguez-Tébar et al., Binding of brain-derived neurotrophic factor to the nerve growth factor receptor. Neuron. Apr. 1990;4(4):487-92.
Sargent et al., Membrane lipid phase as catalyst for peptide-receptor interactions. Proc Natl Acad Sci U S A. Aug. 1986;83(16):5774-8.
Sleep et al., Injectable biomimetic liquid crystalline scaffolds enhance muscle stem cell transplantation. Proc Natl Acad Sci U S A. Sep. 19, 2017;114(38):E7919-E7928.
Sur et al., Epitope topography controls bioactivity in supramolecular nanofibers. Biomater Sci. Mar. 2015;3(3):520-32.
Tanaka et al., Protein synthesis and neurotrophin-dependent structural plasticity of single dendritic spines. Science. Mar. 21, 2008;319(5870):1683-7.
Tapley, P.; Lamballe, F.; Barbacid, M., K252a is a selective inhibitor of the tyrosine protein kinase activity of the trk family of oncogenes and neurotrophin receptors. Oncogene 1992, 7 (2), 371-81.
Thoenen et al., Neurotrophins: from enthusiastic expectations through sobering experiences to rational therapeutic approaches. Nat Neurosci. Nov. 2002;5 Suppl:1046-50.
Thomas et al., MAPK cascade signalling and synaptic plasticity. Nat Rev Neurosci. Mar. 2004;5(3):173-83.

(56) References Cited

OTHER PUBLICATIONS

Webber et al., Supramolecular nanostructures that mimic VEGF as a strategy for ischemic tissue repair. Proc Natl Acad Sci U S A. Aug. 16, 2011;108(33):13438-43.
Wellmer et al., A double-blind placebo-controlled clinical trial of recombinant human brain-derived neurotrophic factor (rhBDNF) in diabetic polyneuropathy. J Peripher Nerv Syst. Dec. 2001;6(4):204-10.
Yoshii et al., Postsynaptic BDNF-TrkB signaling in synapse maturation, plasticity, and disease. Dev Neurobiol. Apr. 2010;70(5):304-22.
Zhang et al., A self-assembly pathway to aligned monodomain gels. Nat Mater. Jul. 2010;9(7):594-601.

* cited by examiner a

BDNF Mimetic Peptide b

R = BDNF Mimetic PA c

R = Linear BDNF Mimetic PA

BDNF MIMETIC PEPTIDE AMPHIPHILES

CROSS-REFERENCE TO RELATED APPLICATIONS

The present invention claims priority to U.S. Provisional Patent Application 62/653,939, filed Apr. 6, 2018, which is incorporated by reference in its entirety.

STATEMENT REGARDING FEDERAL FUNDING

This invention was made with government support under EB003806 awarded by the National Institutes of Health. The government has certain rights in the invention.

FIELD

Provided herein are peptide amphiphiles (PAs) and supramolecular PA nanostructures that mimic brain derived neurotrophic factor (BDNF), a growth factor that induces neuronal survival, maturation, and increased electrical activity. In particular, injectable biomaterials comprising BDNF mimetic PAs are provided, as well as methods of using BDNF mimetic PAs for the treatment or prevention of neurological injuries, diseases, and disorders.

BACKGROUND

Brain derived neurotrophic factor (BDNF), a growth factor that induces neuronal survival, maturation, and increased electrical activity. Direct BDNF protein delivery has had little success in clinical trials because its fast degradation limits improvement.

SUMMARY

Provided herein are peptide amphiphiles (PAs) and supramolecular PA nanostructures that mimic brain derived neurotrophic factor (BDNF), a growth factor that induces neuronal survival, maturation, and increased electrical activity. In particular, injectable biomaterials comprising BDNF mimetic PAs are provided, as well as methods of using BDNF mimetic PAs for the treatment or prevention of neurological injuries, diseases, and disorders. In some embodiments, provided herein are compositions comprising brain derived neurotrophic factor (BDNF) peptide amphiphiles. In some embodiments, the peptide amphiphiles comprise a hydrophobic non-peptide tail, a structured peptide segment, a charged peptide segment, and a BDNF peptide. In some embodiments, the hydrophobic non-peptide tail comprises an 8-24 carbon alkyl chain ($C_{8-24}$). In some embodiments, the structured peptide segment comprises VVAA (SEQ ID NO: 2) or any suitable combination or V and/or A residues. In some embodiments, the structured peptide segment has propensity to form β-sheet-like structures with adjacent structured peptide segments. In some embodiments, the charged peptide segment comprises an acidic, basic, or zwitterionic peptide segment. In some embodiments, the charged peptide segment comprises EE or KK. In some embodiments, the charged peptide segment comprises EEEE (SEQ ID NO: 10). In some embodiments, the peptide amphiphile comprises EEEEAAVV-$C_{8-24}$ (SEQ ID NO: 3). In some embodiments, the BDNF peptide comprises at least 70% sequence similarity with one of SEQ ID NO: 1. In some embodiments, the BDNF peptide comprises at least 70% sequence identity with one of SEQ ID NO: 1. In some embodiments, the BDNF peptide comprises SEQ ID NO: 1. In some embodiments, the BDNF peptide is a cyclic peptide. In some embodiments, the BDNF peptide comprises SEQ ID NO: 1 and is cyclized using the d-Proline [dP]. In some embodiments, the BDNF peptide is attached to the charged peptide by a linker. In some embodiments, the linker comprises a PEG linker. In some embodiments, the linker comprises a PEG6 linker. In some embodiments, the linker is attached to the BDNF peptide at lysine(aK). In some embodiments, the peptide amphiphile comprises RKK(aK)(dP)-(PEG6 Spacer)-EEEEAAVV-$C_{8-24}$ (SEQ ID NO: 4). In some embodiments, the peptide amphiphile comprises RKK(aK)(dP)-(PEG6 Spacer)-EEEEAAVV-$C_{16}$ (SEQ ID NO: 5).

In some embodiments, provided herein are nanofibers comprising the self-assembled peptide amphiphiles described herein. In some embodiments, nanofibers further comprise filler peptide amphiphiles, wherein the filler peptide amphiphiles do not comprise a bioactive moiety. In some embodiments, the filler peptide amphiphiles comprise a hydrophobic non-peptide tail, a structured peptide segment, and a charged peptide segment. In some embodiments, the hydrophobic non-peptide tail of the filler peptide comprises an 8-24 carbon alkyl chain ($C_{8-24}$). In some embodiments, the structured peptide segment of the filler peptide comprises VVAA (SEQ ID NO: 2) or any suitable combination or V and/or A residues. In some embodiments, the structured peptide segment of the filler peptide has propensity to form β-sheet-like structures with adjacent structured peptide segments. In some embodiments, the charged peptide segment of the filler peptide comprises an acidic, basic, or zwitterionic peptide segment. In some embodiments, the charged peptide segment comprises EE or KK. In some embodiments, the filler peptide amphiphile comprises EEAAVV-$C_{8-24}$ (SEQ ID NO: 6).

In some embodiments, provided herein are methods comprising administering a nanofiber described herein to a subject. In some embodiments, the nanofiber is pharmaceutically formulated. In some embodiments, the nanofiber is administered by injection (or any other suitable route of administration). In some embodiments, the nanofiber is administered to enhance neuronal survival, growth, and/or synaptic plasticity. In some embodiments, the nanofiber is administered to treat and/or prevent a neurological and/or psychiatric disease or condition. In some embodiments, administering the nanofiber activates TrkB signaling. In some embodiments, administering the nanofiber activates MAPK, PI3K and/or PLCγ. In some embodiments, administering the nanofiber guides endogenous neural cells to repopulate dysfunctional areas of the central nervous system.

In some embodiments, provided herein are kits comprising the nanofibers described herein and one or more additional components for delivering the nanofiber, storing the nanofiber, and/or for the treatment/prevention of a neurological and/or psychiatric disease or condition.

DEFINITIONS

Figure 1:
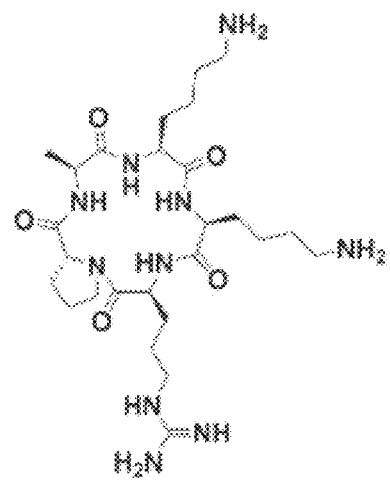
FIG. 1. Design and characterization of BDNF mimetic peptide amphiphiles (PAs). (a-d) Chemical structures of (a) BDNF peptide (b) BDNF PA, (c) Linear BDNF PA and (d) $E_2$ filler PA. (e j) Structural analysis of PAs. (e) Cryo-TEM and (f) DLS of BDNF PA at 100 mol % with average size distribution of particles at ~12 nm in diameter. (g-i) Cryo-TEM of (g) $E_2$ filler PA at 100 mol % (h) Linear BDNF PA and (i) BDNF PA, both co-assembled at 10 mol % with $E_2$ filler PA. (j) SAXS of PAs showing $E_2$ filler PA (fitted to lamellar head-to-tail form factor model), Linear BDNF PA (fitted to core shell cylinder model) and BDNF mimetic PA both co-assembled at 10 mol % with $E_2$ filler PA (fitted to core shell cylinder model), and BDNF PA at 100 mol % (fitted to sphere model).
Figure 1:
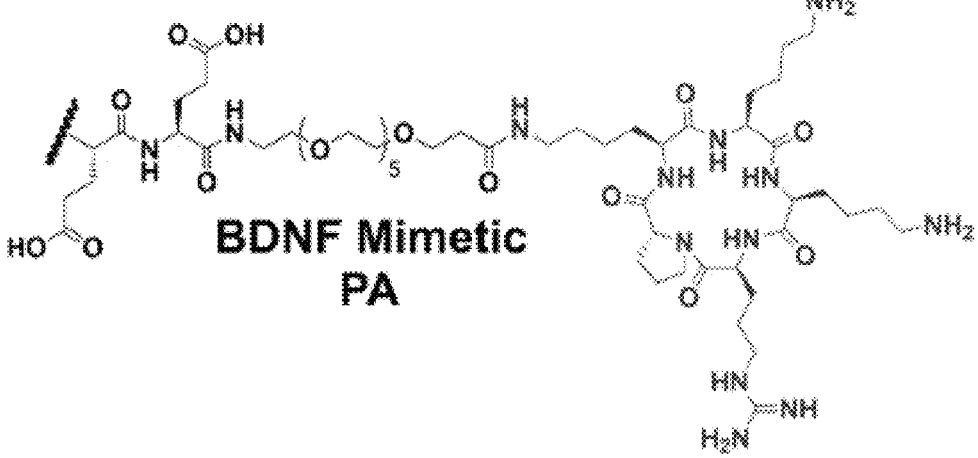
Figure 1:
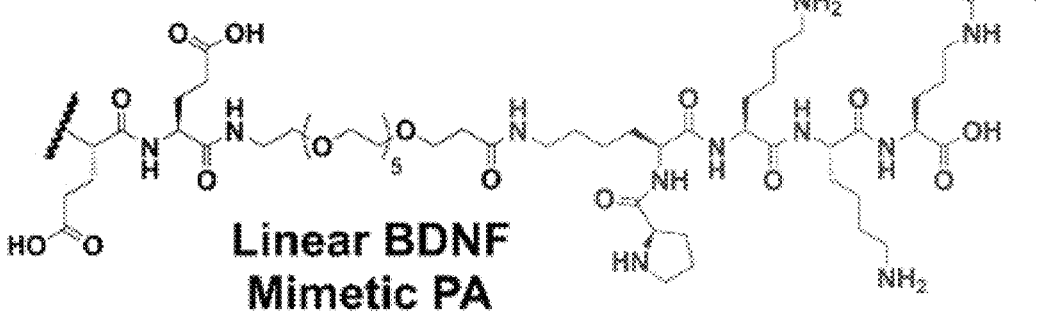
Figure 1:
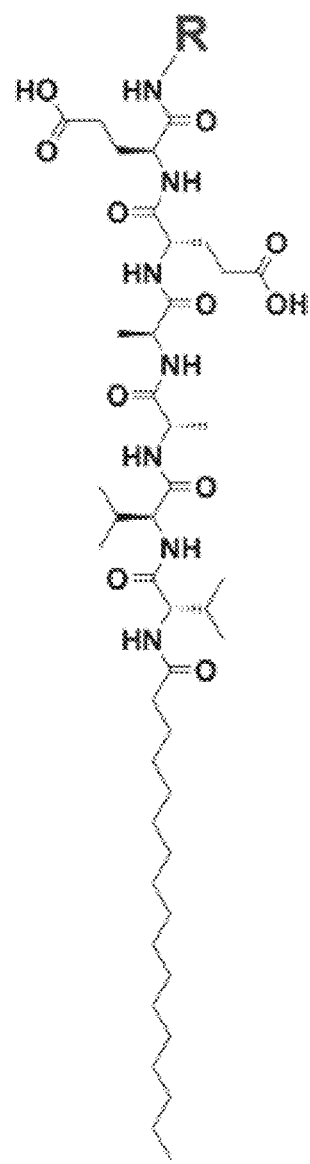
Figure 1:
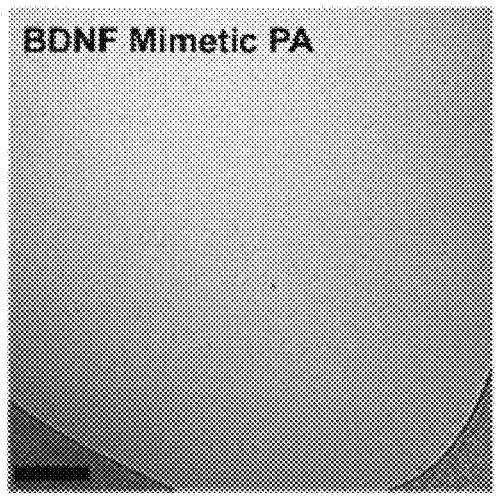
Figure 1:
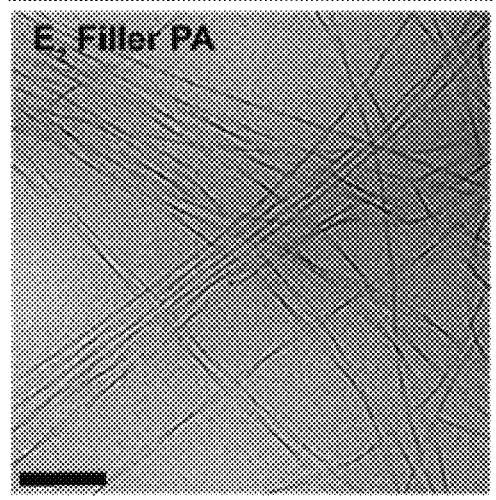
Figure 1:
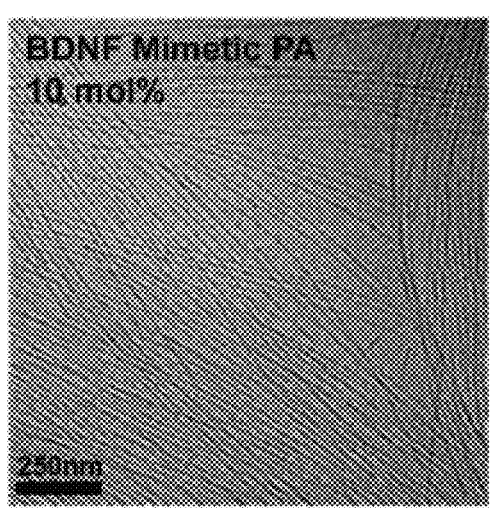
Figure 1:
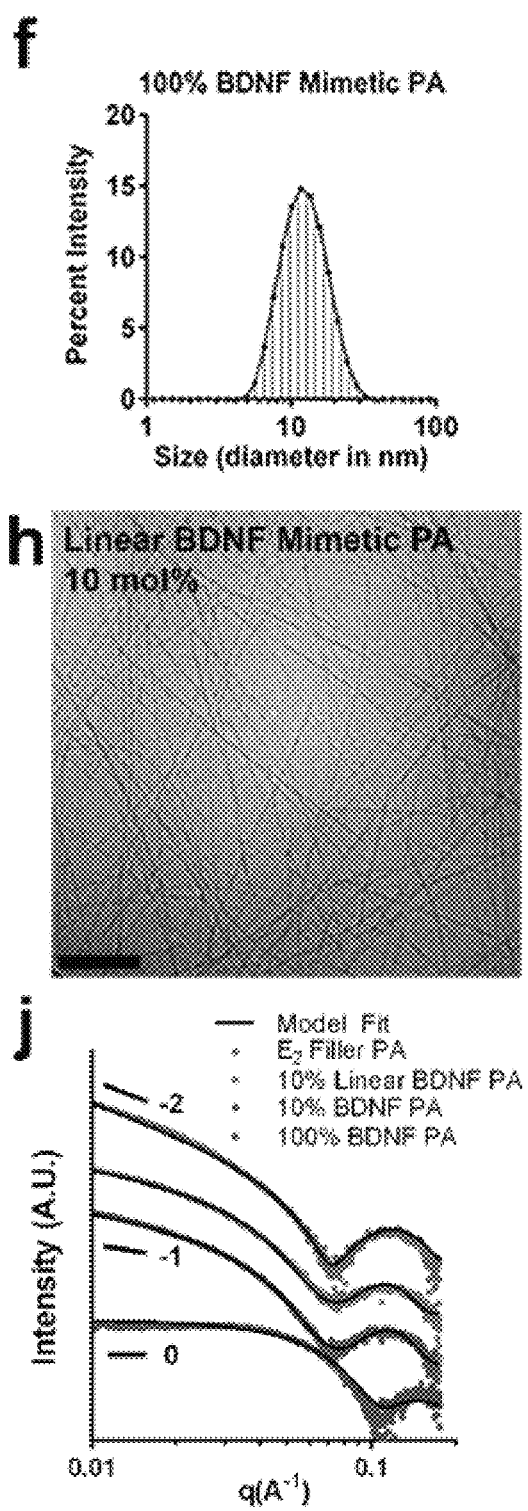

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "Pgly"), pipecolic acid, thioproline ("ThioP" or "tPro"), homoLysine ("hLys"), and diethyl dithio ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid I;
3) Asparagine (N) and Glutamine (Q);
4) Arginine I and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine I and Methionine (M).

Naturally occurring residues may be divided into classes based on common side chain properties, for example: polar positive (or basic) (histidine (H), lysine (K), and arginine I); polar negative (or acidic) (aspartic acid (D), glutamic acid I); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs. Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a bioactive segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a bioactive segment (e.g., linker segment).

As used herein and in the appended claims, the term "lipophilic moiety" or "hydrophobic moiety" refers to the moiety (e.g., an acyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by small angle x-ray scattering (SAXS) or circular dichroism (CD).

As used herein, the term "beta (β-sheet-forming peptide segment" refers to a structural peptide segment that has a propensity to display β-sheet-like character (e.g., when analyzed by CD). In some embodiments, amino acids in a beta (β-sheet-forming peptide segment are selected for their propensity to form a beta-sheet secondary structure. Examples of suitable amino acid residues selected from the twenty naturally occurring amino acids include Met (M), Val (V), Ile (I), Cys I, Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu I, Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg I, Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "bioactive peptide" refers to amino acid sequences that mediate the action of sequences, molecules, or supramolecular complexes associated therewith. Peptide amphiphiles and structures (e.g., nanofibers) bearing bioactive peptides (e.g., a BDNF mimetic sequence, etc.) exhibits the functionality of the bioactive peptide.

The term "effective dose" or "effective amount" refers to an amount of an agent that results in the reduction of symptoms in a patient or results in a desired biological outcome (e.g., cessation of bleeding).

As used herein, the terms "administration" and "administering" refer to the act of giving/taking a drug, prodrug, or other agent, or therapeutic to/by a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.). The term "treating" refers to administering an agent to a subject for therapeutic and/or prophylactic/preventative purposes.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are peptide amphiphiles (PAs) and supramolecular PA nanostructures that mimic brain derived neurotrophic factor (BDNF), a growth factor that induces neuronal survival, maturation, and increased electrical activity. In particular, injectable biomaterials comprising BDNF mimetic PAs are provided, as well as methods of using BDNF mimetic PAs for the treatment or prevention of neurological injuries, diseases, and disorders.

Peptide amphiphiles (PAs) are a class of biomaterials that have emerged as attractive candidates for regenerative medicine due to their ability to assemble into high-aspect ratio nanofibers capable of mimicking the extracellular matrix and gelling upon exposure to physiological ions (Refs. 26-27; herein incorporated by reference in their entireties). PAs are structural units, typically comprising: a hydrophobic tail (e.g., an alkyl group), a structural domain (e.g., β-sheet forming peptide domain), and often a bioactive peptide segment (e.g., BDNF peptide); suitable PAs self-assemble under aqueous conditions to for supramolecular nanostructures (e.g., nanofibers). PAs have been developed displaying diverse bioactive epitopes such as IKVAV, VEGF and FGF-2 with the ability to activate β-1 integrin, VEGFR-1, and FGFR-1 receptors, respectively (Refs. 28-31; herein incorporated by reference in their entireties).

Brain-derived neurotrophic factor, also known as BDNF, is a protein that, in humans, is encoded by the BDNF gene. BDNF is a member of the neurotrophin family of growth factors, which are related to the canonical nerve growth factor. Neurotrophic factors are found in the brain and the periphery. BDNF acts on certain neurons of the central nervous system and the peripheral nervous system, helping to support the survival of existing neurons, and encourage the growth and differentiation of new neurons and synapses. In the brain, it is active in the hippocampus, cortex, and basal forebrain—areas vital to learning, memory, and higher thinking. It is also expressed in the retina, motor neurons, the kidneys, saliva, and the prostate. BDNF binds at least two receptors on the surface of cells that are capable of responding to this growth factor, TrkB and the LNGFR (low-affinity nerve growth factor receptor).

Various studies have shown indicated links between BDNF and diseases/conditions, such as depression, schizophrenia, obsessive-compulsive disorder, Alzheimer's disease, Huntington's disease, Rett syndrome, and dementia, as well as anorexia nervosa and bulimia nervosa. For example, exposure to stress and the stress hormone corticosterone has been shown to decrease the expression of BDNF in rats, and, if exposure is persistent, this leads to an eventual atrophy of the hippocampus. Post mortem analysis has shown lowered levels of BDNF in the brain tissues of people with Alzheimer's disease. Epilepsy has been linked with polymorphisms in BDNF.

The ability of neurotrophic factors to regulate the developing central nervous system (CNS) and to promote survival has encouraged the idea that such proteins could be harnessed for the treatment of a variety of CNS diseases and injuries (Refs. 1-2; herein incorporated by reference in their entireties). The main neurotrophins include brain-derived neurotrophic factor (BDNF), nerve growth factor, neurotrophin-3, and neurotrophin-4.3 Among these, BDNF is the most extensively studied due to its potential capacity to mediate neuroprotection post-injury and functional recovery (Refs. 4-5; herein incorporated by reference in their entireties). It is well known that BDNF binds with high affinity to the tyrosine kinase B (TrkB) receptor and with low affinity to p75NTR, a non-specific neurotrophin receptor (Refs 6-8; herein incorporated by reference in their entireties). Additionally, BDNF activates certain cell pathways promoting neuronal survival, differentiation, maturation, re-myelination, and synaptic plasticity (Refs. 9-11; herein incorporated by reference in their entireties). A correlation between decreased levels of BDNF and the mechanisms underlying injuries in the CNS, as well as neurodegenerative conditions including Alzheimer's and Parkinson's diseases, has been demonstrated. These findings indicate the potential therapeutic role for BDNF in neural regeneration (Refs. 12-16; herein incorporated by reference in their entireties). However, BDNF-based therapies have had little success in the clinic because the native protein has a short half-life in serum, exhibits low blood-brain barrier penetration, and may cause adverse off-target effects at high concentrations (Refs. 17-20; herein incorporated by reference in their entireties).

Several BDNF mimetic peptide sequences were identified by Hughes et al. that promoted the survival of neuronal cultures (Refs. 21-22; herein incorporated by reference in their entireties). They utilized a computer-aided molecular design approach to identify these BDNF mimetic candidates. The most recently described mimetic peptide was a pentapeptide sequence (cyclic: RKKA$_D$P (SEQ ID NO: 1)) found in loop 4 of the native BDNF protein, which was the only monocyclic mimetic found to behave as a BDNF-like agonist (Refs. 23-24; herein incorporated by reference in their entireties). Studies demonstrated that this sequence increased survival of chick sensory neurons and re-myelination in a peripheral nerve injury via TrkB-independent mechanisms. Despite their mimetic design, Hughes et al. found that the RKKADP peptide in this monocyclic conformation cannot activate the TrkB receptor (Refs. 24-25; herein incorporated by reference in their entireties).

In some embodiments, provided herein is the incorporation of the RKKA$_D$P BDNF mimetic peptide (BDNF peptide) on a PA capable of assembling in aqueous media into one-dimensional supramolecular nanostructures. In some embodiments, the BDNF mimetic PAs (BDNF PAs) herein possess the ability to activate the TrkB receptor when displayed on a supramolecular nanofiber. The activation of the TrkB receptor and its corresponding pathways were characterized by studying intracellular signaling of primary cortical neurons treated with BDNF PA. Experiments were conducted during development of embodiments herein to demonstrate the impact of BDNF PAs on cell survival, growth and functional maturation in 2D and 3D cultures.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH2, and —NH2.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a nanofibers)) that bury the lipophilic segment in their core and display the bioactive peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; $2^{nd}$ ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 7), AAAVVV (SEQ ID NO: 8), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C=O groups (e.g., $CH_2(O(CH_2)_2)_2NH$, $CH_2(O(CH_2)_2)_2NHCO(CH_2)_2CCH$, etc.). In some embodiments, a spacer or linker further comprises additional bioactive groups, substituents, branches, etc.

Suitable peptide amphiphiles, PA segments, PA nanostructures, and associated reagents and methods are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA (SEQ ID NO: 2)); and (c) a charged segment (e.g., comprising KK, EE, etc). In some embodiments, any PAs within the scope described herein, comprising the components described herein, or within the skill of one in the field, may find use herein.

In some embodiments, peptide amphiphiles comprise a bioactive moiety. In particular embodiments, a bioactive moiety is the C-terminal or N-terminal most segment of the PA. In some embodiments, the bioactive moiety is attached to the end of the charged segment. In some embodiments, the bioactive moiety is exposed on the surface of an assembled PA structure (e.g., nanofiber). A bioactive moiety is typically a peptide (e.g., BDNF peptide, etc.), but is not limited thereto. Examples described in detail herein utilize a peptide sequence that binds TrkB as a bioactive moiety. In some embodiments, a bioactive peptide is a therapeutic peptide. Bioactive peptides and other moieties for achieving functionality will be understood. In some embodiments, bioactive moieties are provided having binding affinity for a target protein (e.g., TrkB). The binding affinity ($K_d$) may be chosen from one of: less than 10 µM, less than 1 µM, less than 100 nM, less than 10 nM, less than 1 nM, less than 100 µM.

In some embodiments, the bioactive peptide is a BDNF peptide. Suitable examples include SEQ ID NO: 1. In some embodiments, a bioactive peptide binds TrkB and has at least 50% (e.g., 50%, 60%, 70%, 75%, 80%, 85%, 90%, 95%, 100%, or more, or ranges therebetween) sequence identity with one of SEQ ID NO: 1. In some embodiments, a bioactive peptide binds TrkB and has at least 50% (e.g., 50%, 60%, 70%, 75%, 80%, 85%, 90%, 95%, 100%, or more, or ranges therebetween) sequence similarity (e.g., conservative or semi-conservative) with one of SEQ ID NO: 1. In some embodiments, a bioactive peptide binds TrkB and has 5 or fewer (e.g., 5, <5, 4, <4, 3, <3, 2, <2, 1, 0) substitutions relative to SEQ ID NO: 1. In some embodiments, a bioactive peptide binds TrkB and has 5 or fewer (e.g., 5, <5, 4, <4, 3, <3, 2, <2, 1, 0) non-conservative substitutions relative to SEQ ID NO: 1. In some embodiments, a bioactive peptide binds TrkB and has 5 or fewer (e.g., 5, <5, 4, <4, 3, <3, 2, <2, 1, 0) semi-conservative substitutions relative to SEQ ID NO: 1. In some embodiments, a bioactive peptide binds TrkB and has 5 or fewer (e.g., 5, <5, 4, <4, 3, <3, 2, <2, 1, 0) conservative substitutions relative to SEQ ID NO: 1.

In some embodiments, a peptide amphiphile comprises: (a) a hydrophobic tail comprising an alkyl chain of 8-24 carbons; (b) a structural segment (e.g., comprising VVAA (SEQ ID NO: 2), AAVV (SEQ ID NO: 7), VA, AV, etc.); (c) a charged segment (e.g., comprising KK, EE, EK, KE, etc.), and a bioactive peptide (e.g., BDNF peptide). In some embodiments, a PA further comprises an attachment segment or residue (e.g., K) for attachment of the hydrophobic tail to the peptide portion of the PA. In some embodiments, the hydrophobic tail is attached to a lysine side chain.

In some embodiments, a peptide amphiphile comprises (e.g., from C-terminus to N-terminus or from N-terminus to C-terminus): bioactive peptide (e.g., BDNF peptide)—charged segment (e.g., comprising KK, EE, EK, KE, etc.)—structural segment (e.g., comprising VVAA (SEQ ID NO: 2), AAVV (SEQ ID NO: 7), VA, AV, etc.)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., BDNF peptide)—charged segment (e.g., comprising KK, EE, EK, KE, etc.)—structural segment (e.g., comprising VVAA (SEQ ID NO: 2), AAVV (SEQ ID NO: 7), VA, AV, etc.)—attachment segment or peptide (e.g., K)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., BDNF peptide)—KKAAVV(K)—hydrophobic tail (SEQ ID NO: 9) (e.g., comprising an alkyl chain of 8-24 carbons). In some embodiments, the hydrophobic tail is attached to the (K) sidechain.

In some embodiments, provided herein are nanofibers and nanostructures assembled from the peptide amphiphiles described herein. In some embodiments, a nanofiber is prepared by the self-assembly of the PAs described herein. In some embodiments, a nanofiber comprises or consists of PAs displaying a BDNF peptide. In some embodiments, the BDNF peptides are displayed on the surface of the nanofiber. In some embodiments, in addition to PAs displaying BDNF peptides, filler PAs are included in the nanofibers. In some embodiments, filler PAs are peptide amphiphiles, as described herein (e.g., structural segment, charged segment, hydrophobic segment, etc.), but lacking a bioactive moiety. In some embodiments, the filler PAs and BDNF PAs self-assemble into a nanofiber comprising both types of PAs. In some embodiments, nanostructures (e.g., nanofibers) assembled from the peptide amphiphiles described herein are provided.

In some embodiments, nanostructures are assembled from (1) PAs bearing a bioactive moiety (e.g., BDNF moiety) and (2) filler PAs (e.g., PAs not-labeled or not displaying a bioactive moiety, etc.). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a bioactive moiety (e.g., BDNF moiety). In some embodiments, nanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) PAs bearing a bioactive moiety (e.g., BDNF moiety). In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of PAs bearing a bioactive moiety to filler PAs determines the density of bioactive moieties (e.g., BDNF moiety) displayed on the nanostructure surface.

In some embodiments, nanofibers additionally comprise PAs bearing bioactive moieties other than BDNF moieties. For example, in some embodiments, nanofibers comprise filler PAs, PAs bearing BDNF moieties, and PAs bearing a therapeutic moiety. In some embodiments, a therapeutic moiety is a peptide, antibody, nucleic acid (e.g., antisense RNA, siRNA, etc.), small molecule, etc. In some embodiments, a therapeutic moiety is a bioactive peptide. In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a therapeutic moiety.

In some embodiments, a therapeutic moiety is a peptide, nucleic acid, or small molecule that finds use in the treatment of neurologic damage and/or in the treatment of one or more neurological diseases or conditions.

In some embodiments, provided herein are methods of treating and/or preventing neurologic damage and/or in the treatment of one or more neurological diseases or conditions in a subject comprising administering the BDNF nanofibers described herein. In some embodiments, pharmaceutical compositions comprising BDNF nanofibers are provided. Such pharmaceutical compositions may be formulated for any suitable route of administration (e.g., oral, topical, inhalation, intravenous, transdermal, etc.). Embodiments herein are not limited by the route of administration. In some embodiments, the appropriate route of administration is selected based upon the particular indication. Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, the BDNF nanofibers described herein are provided in kits for use in the treatment neurological damage, disease or conditions.

EXPERIMENTAL

Example 1

Synthesis
General Synthesis

Unless otherwise noted, commercial reagents were used as received. For column chromatography, Silica gel 60 (particle size 60-200 μm; silica; Alfa Aesar) was used. $^1$H NMR spectra were recorded on a Varian model Inova 500 spectrometer, operating at 500 MHz, where chemical shifts were determined with respect to tetramethylsilane as an internal reference. Preparative reverse-phase high-performance liquid chromatography (RP-HPLC) was performed at 25° C. using a Phenomenex Kinetex column (C18 stationary phase, 5 μm, 100 Å pore size, 30.0×150 mm) on a Shimadzu model prominence modular HPLC system equipped with a DGU-20A5R degassing unit, two LC-20AP solvent delivery units, a SPD-M20A diode array detector and a FRC-10A fraction collector, using $H_2O/CH_3CN$ gradient containing 0.1% $NH_4OH$ (v/v) as an eluent at a flow rate of 75.0 mL min$^{-1}$. Electrospray ionization mass spectrometry (ESI-MS) was performed in positive scan mode on an Agilent model 6510 Quadrupole Time-of-Flight LC/MS spectrometer using direct injection. Matrix-assisted laser deposition ionization time-of-flight (MALDI-TOF) mass spectrometry was performed in the reflector mode on a Bruker autoflex III smartbeam spectrometer using α-cyano-4-hydroxycinnamic acid as a matrix.

Fmoc Deprotection. 4-Methylpiperidine (20% in DMF) was added (2×30 ml) and the mixture was shaken for 10 min at room temperature and washed with DMF (2×40 ml) and $CH_2Cl_2$ (2×40 ml).

Peptide Purification

PAs were purified using standard reversed-phase HPLC (Shimadzu). The purity and accurate mass for each PA was verified using liquid chromatography/MS on an electrospray ionization quadrupole time-of-flight mass spectrometer (Agilent).

LCMS Purity Measurements

Analytical liquid chromatography-mass spectroscopy (LC-MS) was performed on an Agilent 1200 system with a Phenomenex Jupiter C-12 column (100×1.00 mm; 5 μm) for acidic conditions or Phenomenex Gemini C-18, (100×1.00 mm; 5 μm) for basic conditions. The mass detector (MS) was an Agilent 6520 quadrupole-time of flight (Q-TOF)/MS. All gradient methods followed: acetonitrile at 5% for 5 min at 50 μL/min, 5-95% over 25 min at 50 μL min$^{-1}$ followed by 95% for 5 min at 50 μl min$^{-1}$. Ammonium hydroxide (0.1% v/v) for basic or formic acid (0.1% v/v) for acidic conditions was added to all solvents. Peaks were detected at 220 nm.

1.2 Synthesis of $E_2$ Filler PA, $E_4$ PA and $E_4$PEG PA. Molecules were synthesized using standard fluorenylmethyloxycarbonyl (Fmoc)-solid phase peptide chemistry. The peptide was synthesized on a Rink amide MBHA low loading resin in the Peptide Synthesis Core at the Simpson Querrey Institute for BioNanotechnology. The $E_2$ Filler PA, $E_4$ PA and $E_4$PEG PA were synthesized using a CEM Liberty microwave-assisted peptide synthesizer. The cleavage solution was prepared by mixing TFA/TIS/$CH_2Cl_2$ (2.5:2.5:95), which was added to the resin-bound peptide, the mixture was shaken for 3 hours after which the solution was collected. The crude peptide was dissolved in 0.1% $NH_4OH$ (aq.), filtered using a 0.2 μm syringe filter and subjected to HPLC purification.

Synthesis of BDNF PAs and Peptides

Loading Fmoc-Arg(Pbf)-OH to 2-chlorotrithyl chloride resin. DMF (15 mL) was used to swell the resin for 30 min. A DMF solution (15 mL) of Fmoc-Arg(Pbf)-OH (649 mg, 1.0 mmol) and N,N-diisopropylethylamine (DIPEA, 260 μL, 1.5 mmol) was added to peptidyl resin, and the reaction vessel was shaken for 2 hours at 25° C. MeOH (400 μL) was then added and the reaction vessel was shaken for another 5 min to cap the free groups on beads. After the coupling solution was drained off, the peptidyl resin was washed with DMF (3 times).

Deprotection of Fmoc group. 4-methylpiperidine in DMF (30% v/v) was added to the peptidyl resin, and the reaction vessel was shaken for 10 min at 25° C. After the reaction solution was drained off, this reaction was repeated one more time, and the resulting peptidyl resin was washed with DMF (3 times) and $CH_2Cl_2$ (1 time).

Peptide coupling using HBTU as a coupling reagent. To a DMF solution (30 mL) of Fmoc-protected amino acid (4.0 mmol) and N,N,N',N'-tetramethyl-O-(1H-benzotriazol-1-yl) uranium hexafluorophosphate (HBTU, 1.5 g, 3.95 mmol) was added DIPEA (1.0 mL, 6 mmol), and the mixture was stirred for 1 min for activation. The mixture was then added to peptidyl resin, and the reaction vessel was shaken for 2 hours at 25° C. After the coupling solution was drained off, the peptidyl resin was washed with DMF (3 times).

Peptide coupling using PyBOP as a coupling reagent. To a DMF solution (15 mL) of Fmoc-protected amino acid (1.1 mmol) and (Benzotriazol-1-yloxy)tripyrrolidinophosphonium hexafluorophosphate (PyBOP, 546 mg, 1.05 mmol) was added DIPEA (290 μL, 1.65 mmol), and the mixture was stirred for 1 min for activation. The mixture was then added to peptidyl resin, and the reaction vessel was shaken for 12 hours at 25° C. After the coupling solution was drained off, the resin was washed with DMF (3 times).

Deprotection of Alloc group. A $CH_2Cl_2$ solution (15 mL) of tetrakis(triphenylphosphine)palladium(0) (Pd(PPh$_3$)$_4$, 116 mg, 100 μmol) and phenylsilane (3.08 mL, 25 mmol) was added to the peptidyl resin, and the reaction vessel was shaken for 2 hours at 25° C. After the reaction solution was drained off, a DMF solution (10 mL) of sodium diethyldithiocarbamate trihydrate (1.0 g, 4.44 mmol) was added to the peptidyl resin, and the reaction vessel was shaken for 20 min at 25° C. This reaction was repeated one more time, and the resulting peptidyl resin was washed with DMF (3 times) and $CH_2Cl_2$ (10 times).

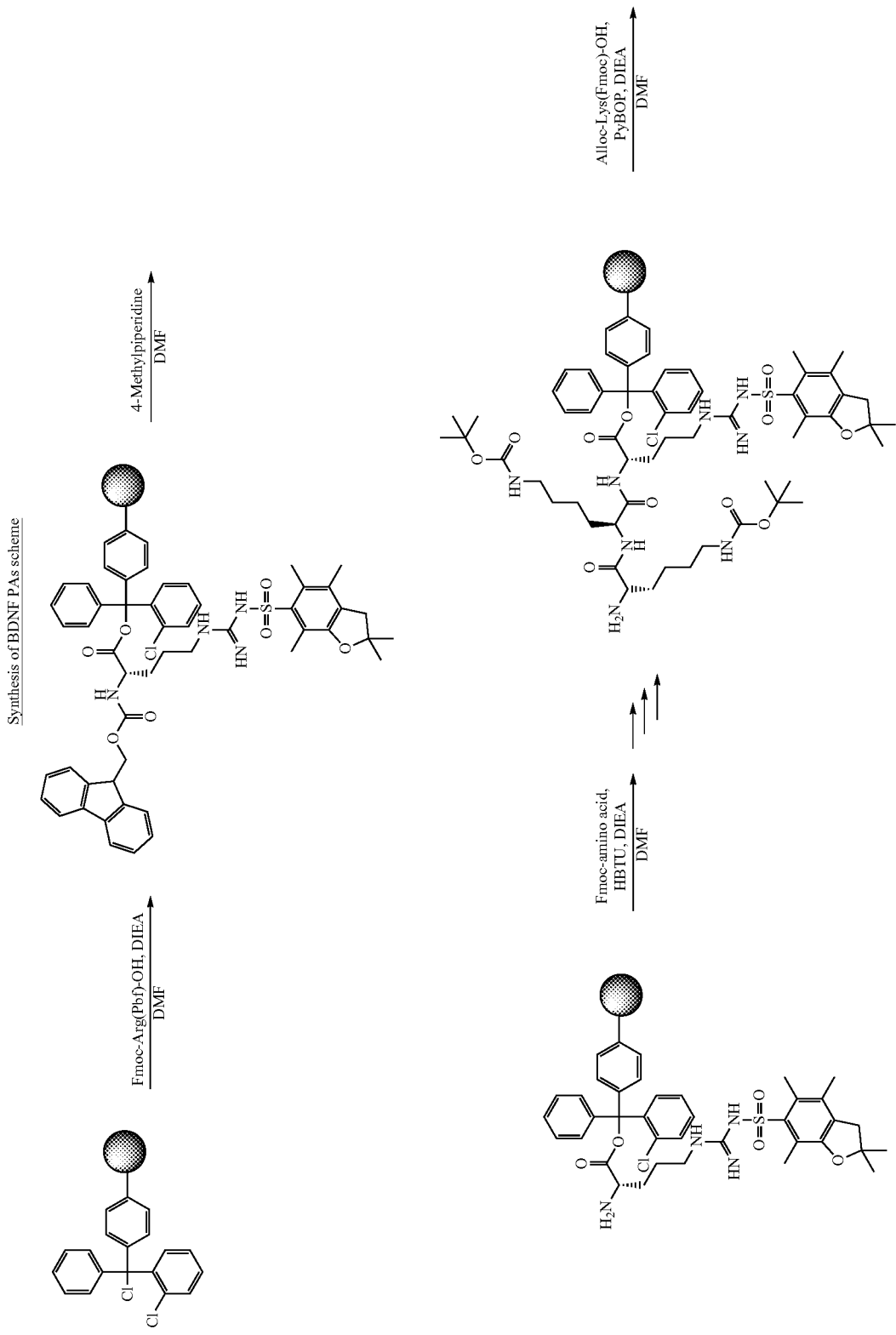

-continued
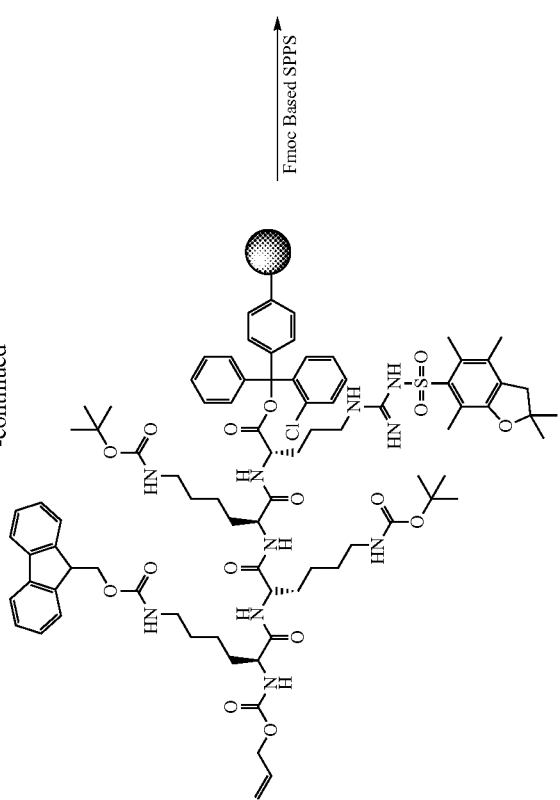
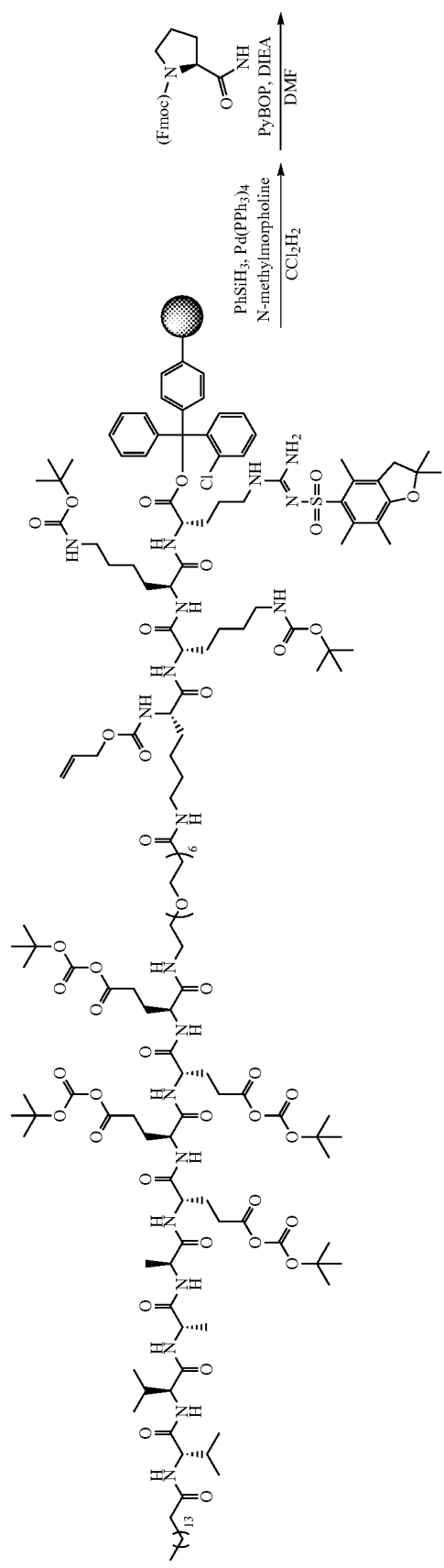

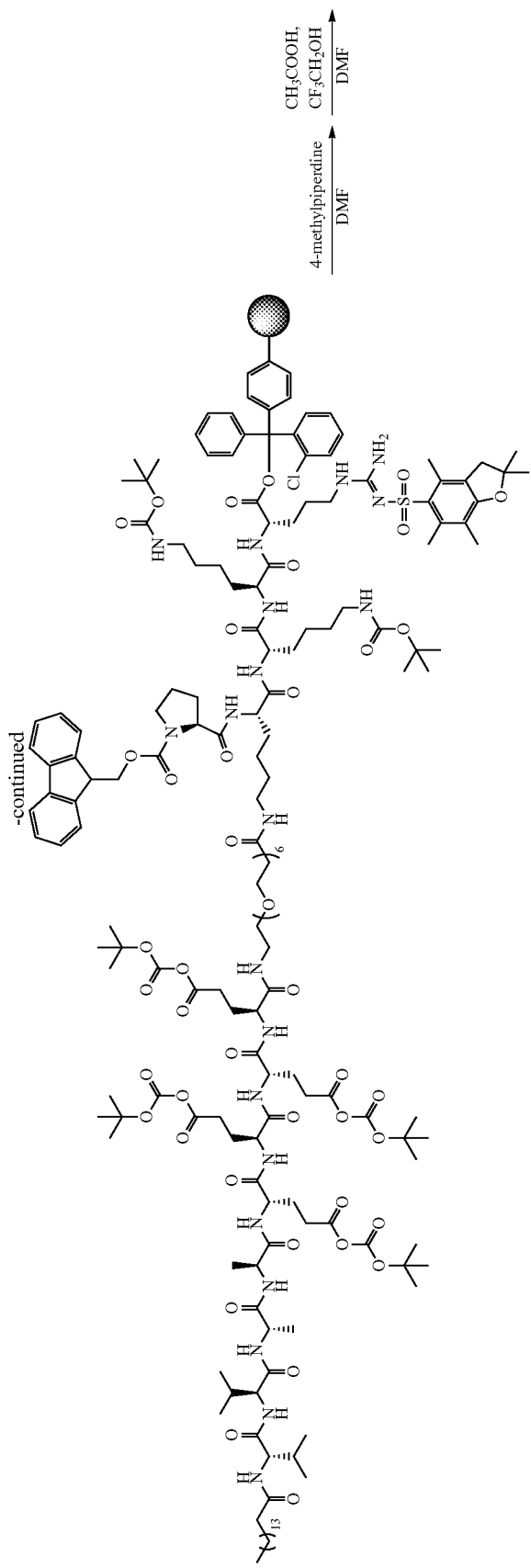
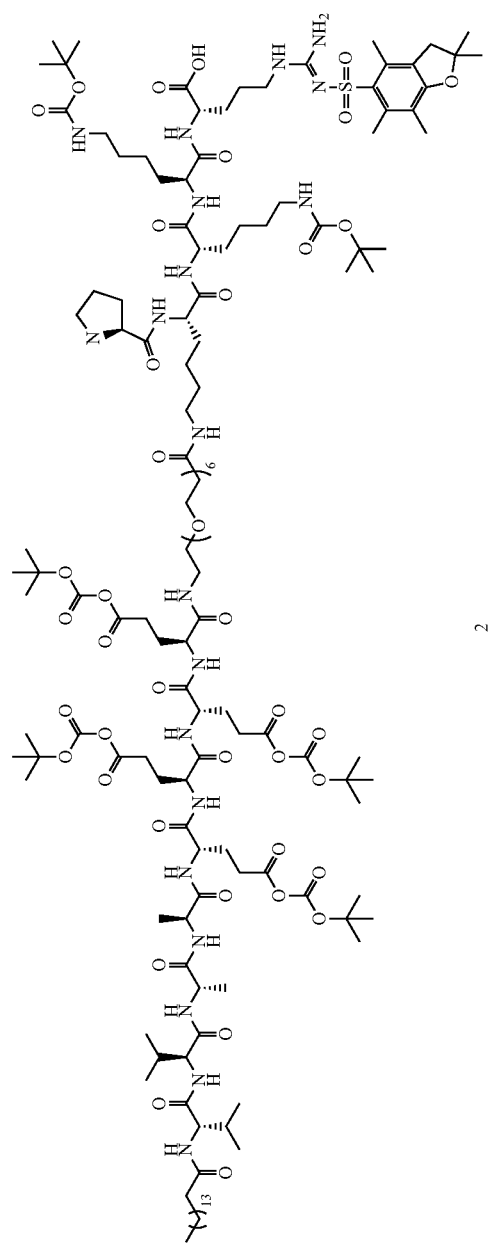

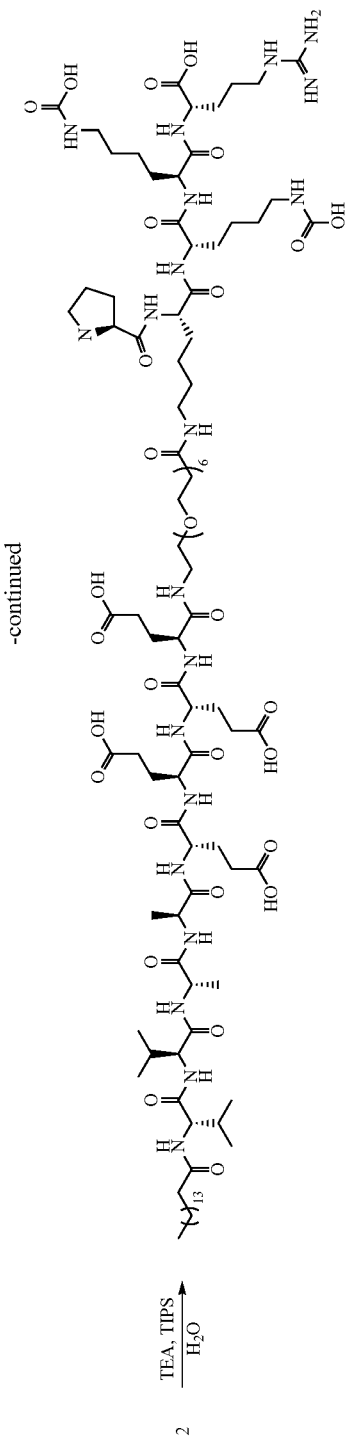
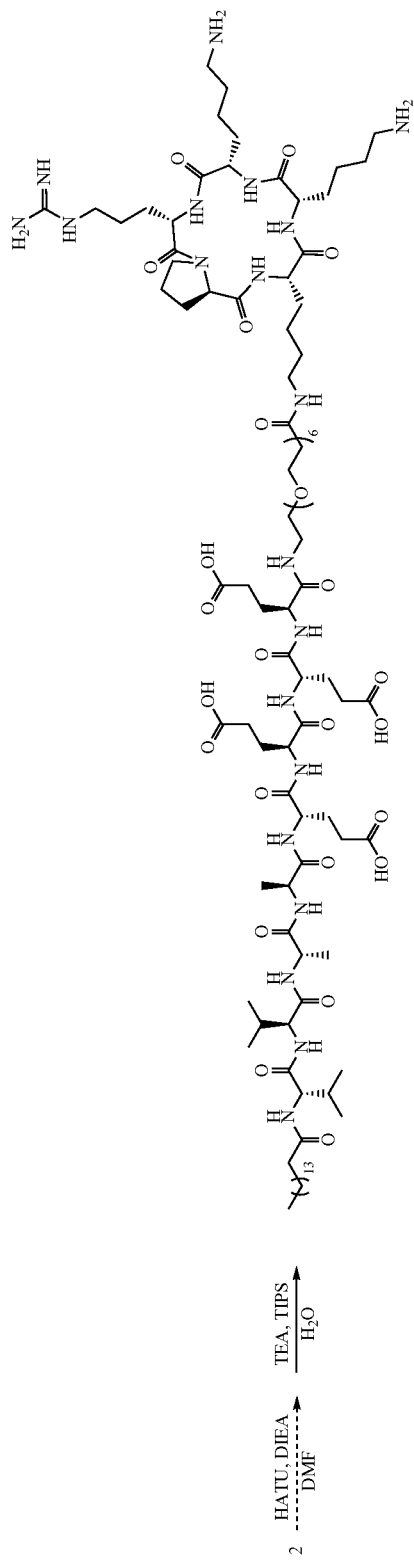
PAs were synthesized in a 2.0 mmol scale on 2-chlorotrityl chloride resin (1.176 g, 1.70 meq g⁻¹ 100-200 mesh) employing a standard Fmoc solid-phase peptide synthesis (SPPS) method.

Synthesis of Linear BDNF PA on Resin. After addition of the alloc-protected lysine to yield peptide 1, a PEG6 linker was added (633 mg, 1.1 mmol). Then, four glutamic acid residues, two alanine residues and two valine residues were sequentially added at 4 molar equivalence (glutamic acid; 1.70 g, alanine; 1.25 g, valine; 1.33 g, 4.0 mmol) using the general procedures described above. Palmitic acid was added and shaken for 3 days at 25° C. after which the alloc was deprotected and d-proline was attached (371 mg, 1.1 mmol) to form PA 2. A mixture of $CH_2Cl_2$/trifluoroethanol/acetic acid (7/2/1, v/v/v) (20 mL) was added to cleave the peptide from the 2-chlorotrithyl chloride resin selectively without deprotecting the amino acids. After shaking for 2 hours, the cleavage mixture and two subsequent $CH_2Cl_2$ washings were filtered. The combined solution was evaporated to a viscous solution under reduced pressure. Then, hexanes were added, and solvent was removed with rotary evaporation and subsequently dried in vacuo for 3 days to remove residual acetic acid. At this point, the batch was split, and half was set aside as PA 3.

Cyclization of linear protected BDNF PA. A DMF solution (15 mL) of 1-[bis(dimethylamino) methylene]-1H-1,2,3-triazolo[4,5-b]pyridinium3-oxid hexafluorophosphate (HATU, 210 mg, 0.55 mmol) and DIPEA (270 μL, 1.5 mmol) was added to PA 2 for 30 min at 25° C. Toluene was added and the solvent was then removed with rotary evaporation and remaining solvent was removed in vacuo over 3 days.

Deprotection of Cyclized BDNF PA and Linear BDNF PA. Remaining protecting groups were removed to form PA 3 and PA 4 with a mixture of trifluoroacetic acid (TFA)/triisopropylsilane (TIS)/$H_2O$ in a ratio of 95:2.5:2.5 for 3 hours. Excess TFA was removed by rotary evaporation. The remaining peptide solution was triturated with cold diethyl ether and the precipitate was collected with vacuum filtration. The crude precipitate was then stored at −20° C. until purification by HPLC.

Synthesis of BDNF Peptide scheme

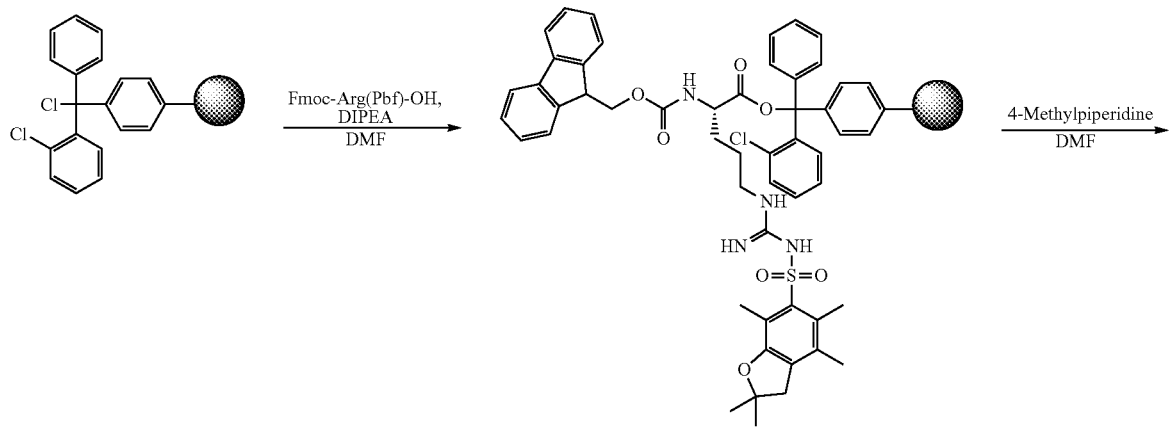

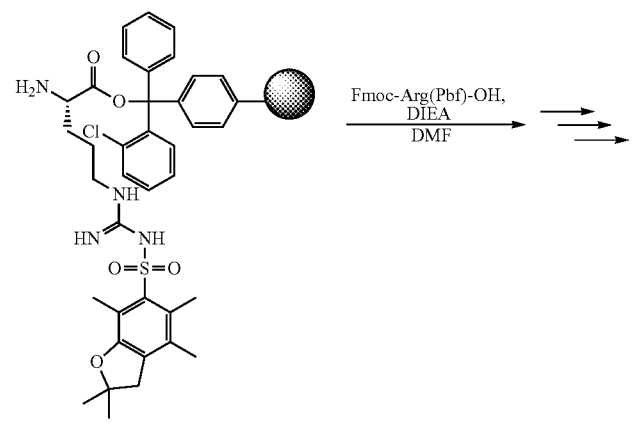

-continued
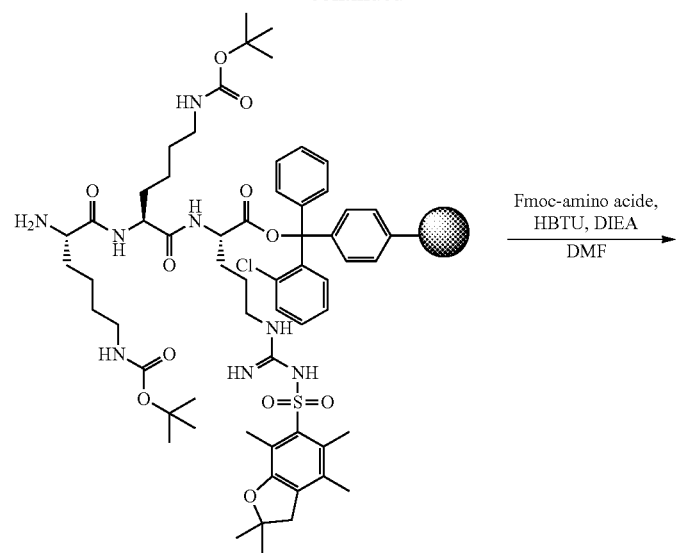
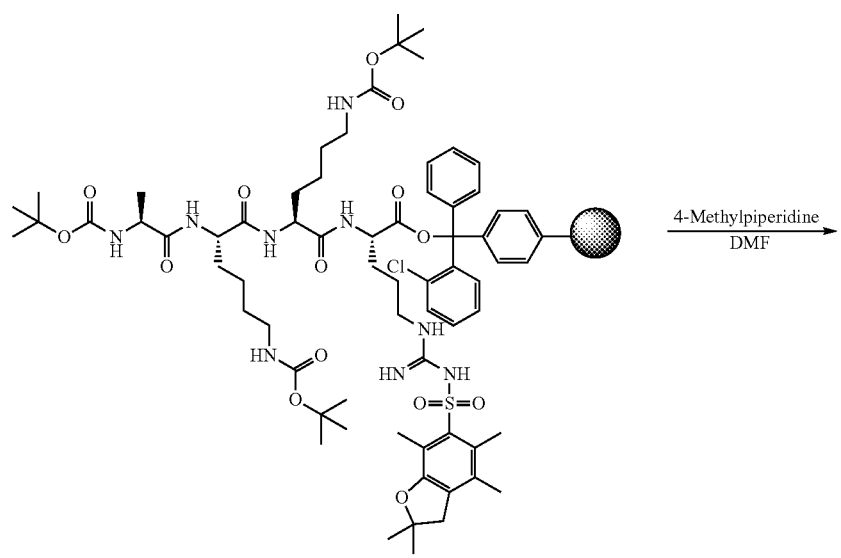
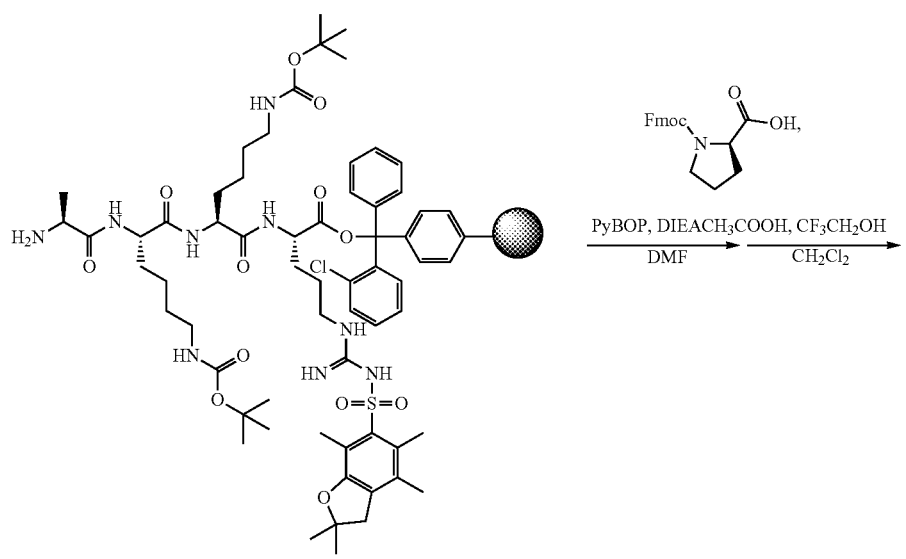

-continued
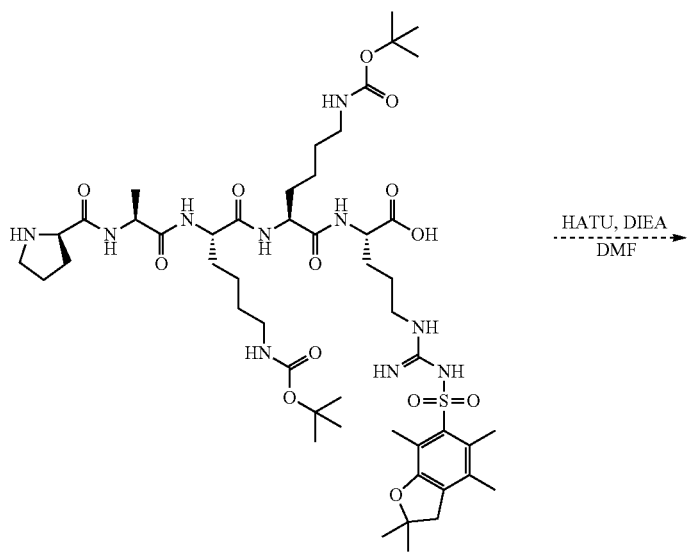
5
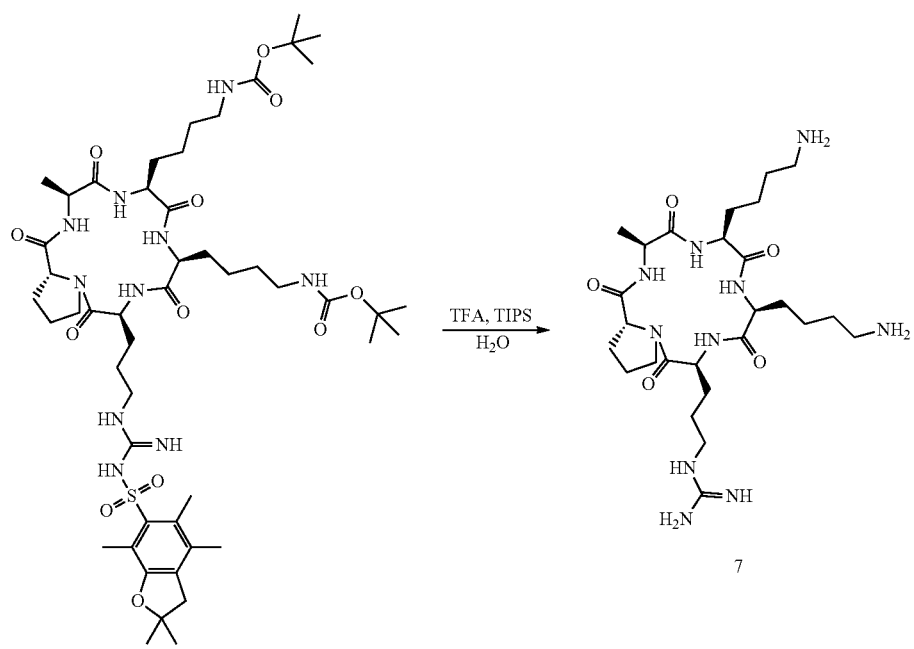
6 → 7
Synthesis of Immobilized BDNF Peptide scheme
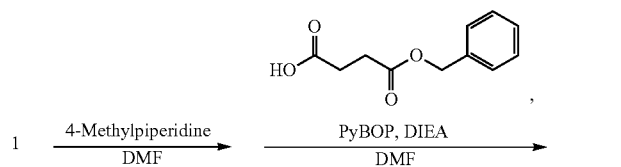

-continued
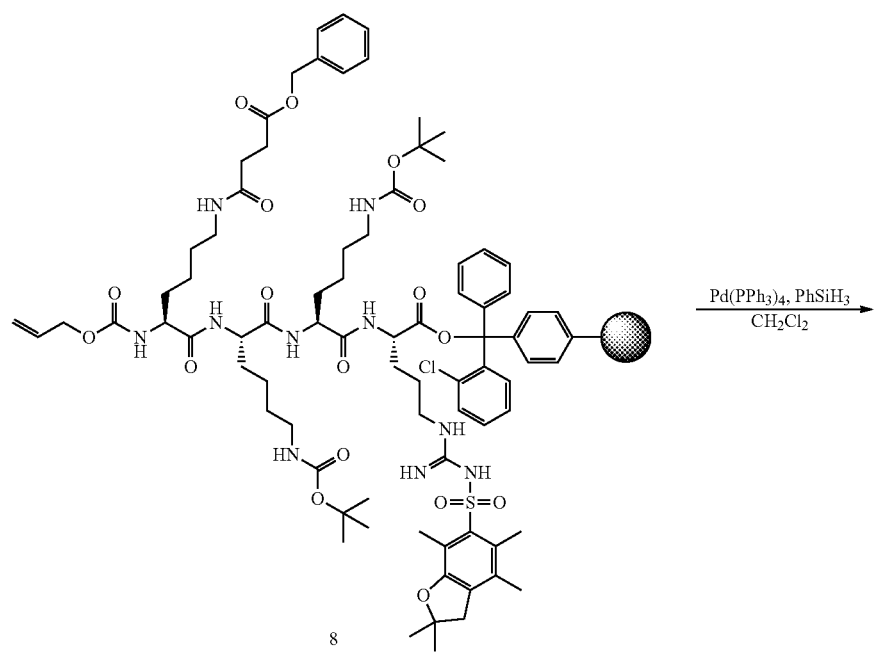
8
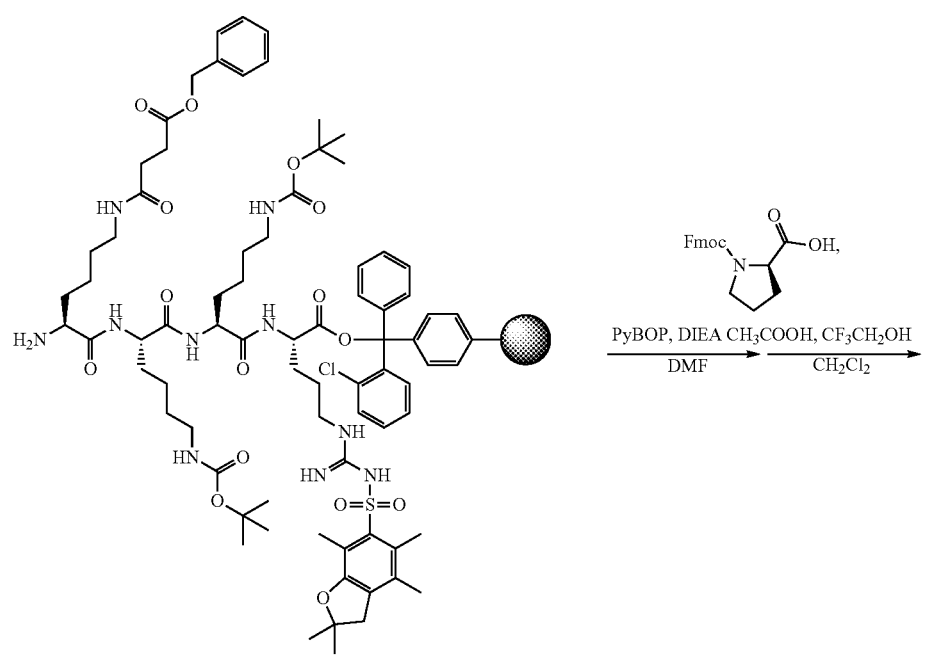

-continued
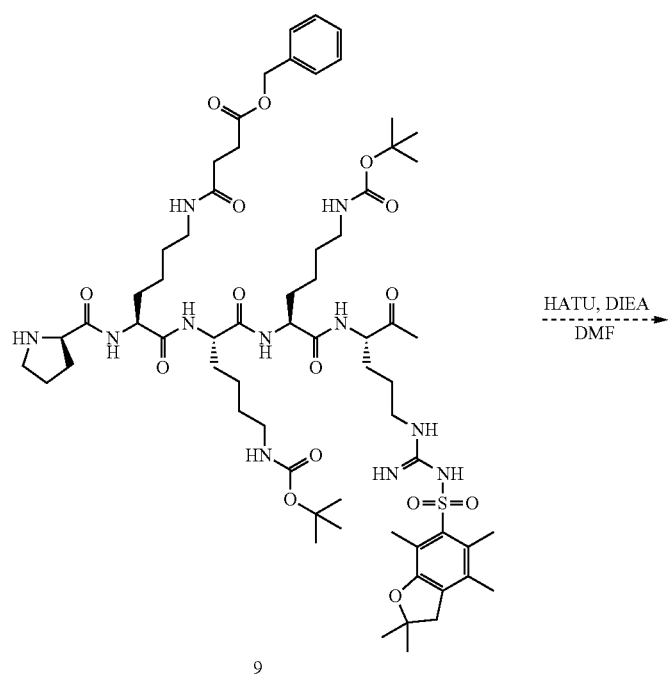
9
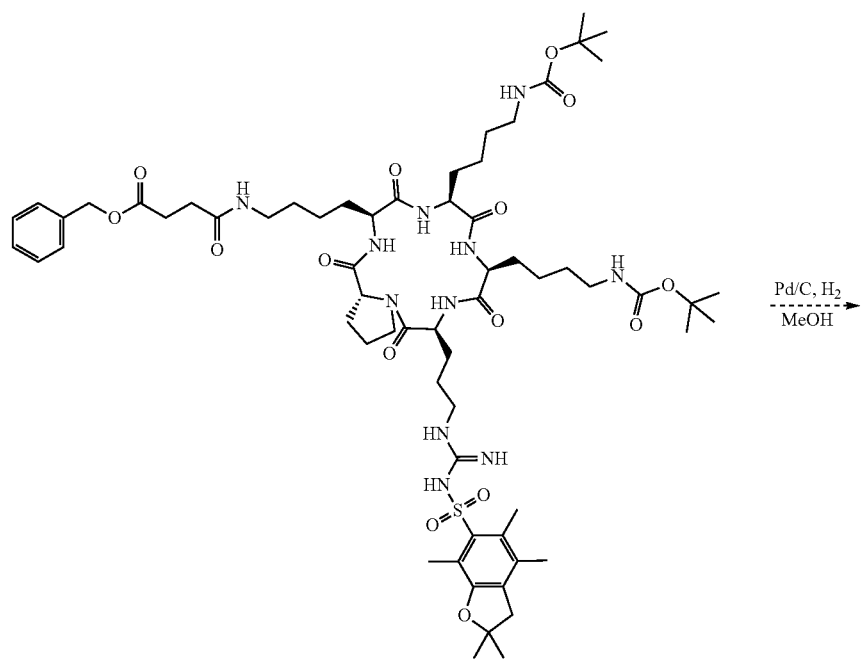
10

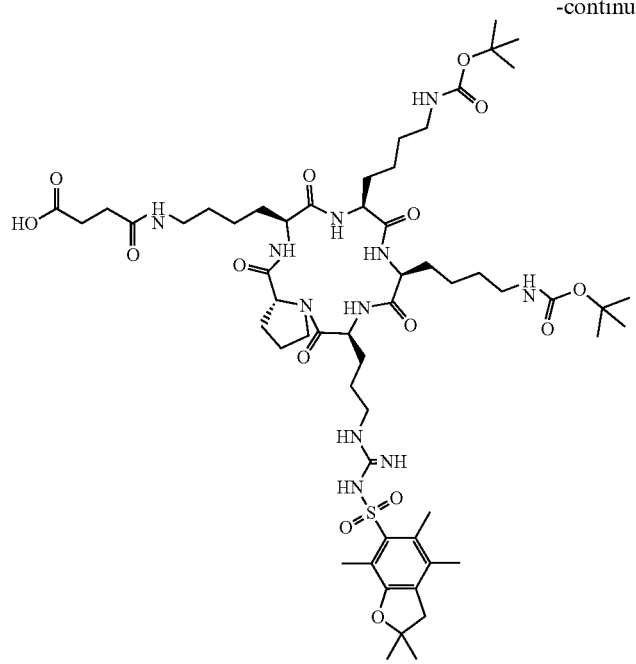

11

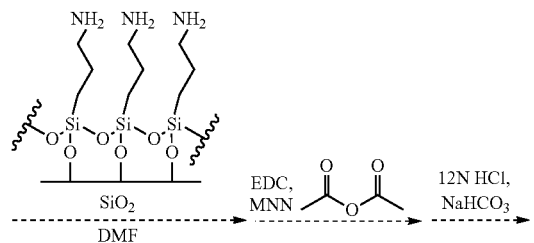

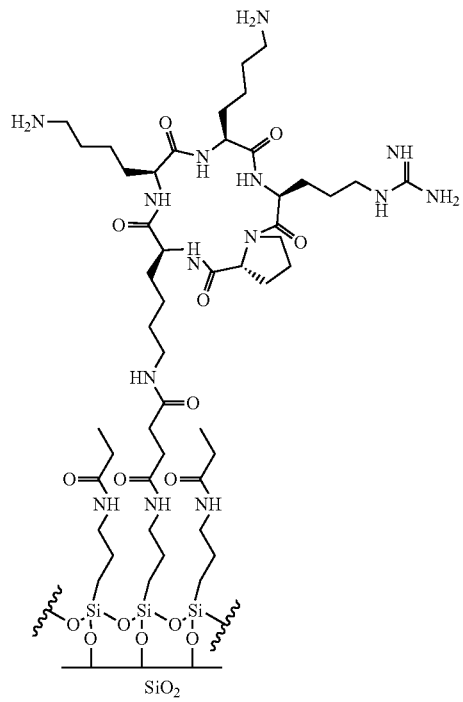

The free BDNF peptide was synthesized in a 1.0 mmol scale and the BDNF peptide for immobilization was synthesized in a 2.0 mmol scale on 2-chlorotrityl chloride resin (Free peptide; 0.588 g, 1.7 meq g$^{-1}$, Immobilized peptide; 1.32 g, 1.52 meq g$^{-1}$ 100-200 mesh) employing a standard Fmoc solid-phase peptide synthesis (SPPS) method.

Coupling 1 with succinic acid monobenzyl ester to form 8. To a DMF solution (15 mL) of succinic acid monobenzyl ester (416 mg, 2.0 mmol) and PyBOP (989 mg, 1.9 mmol) was added DIPEA (520 μL, 3.0 mmol), and the mixture was stirred for 1 min for activation. The mixture was then added to peptidyl resin, and the reaction vessel was shaken for 12 hours at 25° C. After the coupling solution was drained off, the peptidyl resin was washed with DMF (3 times).

Cleavage reaction of peptides 5 and 9 from the peptidyl resin. To a mixture of CH$_2$Cl$_2$/trifluoroethanol/acetic acid (7/2/1, v/v/v) (20 mL) was added the peptidyl resin (1.0 mmol). After shaking for 1.5 hours, the cleavage mixture and two subsequent CH$_2$Cl$_2$ washings were filtered. The combined solution was evaporated to a viscous solution under reduced pressure. Then, cold diethyl ether was added to the solution and the resulting precipitate was washed with cold Et$_2$O (3 times) to remove residual acetic acid. The precipitate was dried under reduced pressure to afford peptides 5 and 9, which were used in the next step without further purification.

Synthesis of cyclic peptide 6 and 7. A DMF solution (15 mL) of HATU (210 mg, 0.55 mmol) and DIPEA (270 μL, 1.5 mmol) was added to peptide 5 for 30 min at 25° C. to form peptide 6. Toluene was added, and the solvent was then removed with rotary evaporation and remaining solvent was removed in vacuo over 3 days. Remaining protecting groups were removed to form peptide 7 with a mixture of trifluoroacetic acid (TFA)/triisopropylsilane (TIS)/$H_2O$ in a ratio of 38:1:1 for 3 hours. Excess TFA was removed by rotary evaporation. The remaining peptide solution was triturated with cold diethyl ether and the precipitate was collected with vacuum filtration. The crude precipitate was then stored at −20° C. until purified.

Synthesis of cyclic peptides 10 and 11. To a DMF solution (30 mL) of peptide 9 (890 mg, 685 μmol) was added HATU (1.67 g, 8.0 mmol) and DIPEA (4.2 mL, 24 mmol) under $N_2$ at 25° C. After stirring for 17 hours, EtOAc (100 mL) was added and the mixture was washed successively with $H_2O$ (100 mL, 3 times) and brine (1 time). The combined organic extract was dried over $Na_2SO_4$ and evaporated to dryness under reduced pressure. The residue was subjected to column chromatography on silica gel using $CH_2Cl_2$/MeOH (19/1=>7/1 v/v), leaving cyclic peptide 10 as a pale-yellow foam (570 mg) which was used for the next step without further purification. MALDI-TOF-MS m/z calcd for $C_{63}H_{97}N_{11}O_{15}SNa$ ($[M+Na]^+$) 1302.68, found 1302.30. To a MeOH solution (20 mL) of cyclic peptide 10 (570 mg) was added 10% Pd/C (120 mg) at 0° C., and the mixture was stirred under atmospheric pressure of $H_2$ for 5 hours at 25° C. The reaction mixture was then filtered through a pad of Celite and eluted with MeOH. The filtrate was evaporated to dryness under reduced pressure. The residue was purified by RP-HPLC to allow isolation of cyclic peptide 11 as a white solid (101 mg, 0.848 mmol, overall yield 8%). $^1$H NMR (500 MHz, MeOH-$d_4$, 25° C., ppm): δ 6.57 (s, 1H), 4.58 (m, 1H), 4.50 (t, J=5.5 Hz, 1H), 4.30 (t, J=6.8 Hz, 1H), 4.20 (dd, J=9.9, 4.1 Hz, 1H), 3.89 (m, 1H), 3.60 (m, 1H), 3.53 (m, 1H), 3.25-3.15 (m, 5H), 3.10-2.95 (m, 8H), 2.60-2.40 (m, 14H), 2.17 (m, 1H), 2.10-2.00 (m, 6H), 2.00-1.85 (m, 6H), 1.85-1.65 (m, 4H), 1.65-1.30 (m, 51H); MALDI-TOF mass m/z calcd. For $C_{56}H_{91}N_{11}O_{15}S$ $[M]^-$: m/z=1189.64, found: 1190.30.

Fabrication of BDNF-mimetic monolayer. The BDNF mimetic peptide was immobilized onto the surface of glass coverslips or 6 μM silica beads (Spherotech). Surfaces were washed with 2% (v/v) micro-90 detergent (Sigma Aldrich) for 30 min at 60° C., then rinsed six times with distilled water. Surfaces were then rinsed with ethanol, and dried. Surfaces were plasma-etched (Harrick Plasma PDC-001-HP) with $O_2$ for 30 s, then immediately incubated in a 2% (v/v) solution of (3-aminopropyl)triethoxysilane (Sigma Aldrich) in ethanol for 15 min. They were then rinsed twice with ethanol and twice with water. Coverslips or beads were dried in the oven. BDNF peptide was attached to surfaces following an established protocol reported previously.[1] COOH-functionalized BDNF mimetic peptide was then prepared at 50 nmol/mL in a 1.25 mg/mL solution of 1-ethyl-3-(dimethyl-aminopropyl)carbodiimide (Arcos Organics) with 2% N,N-dimethyl formamide. Surfaces were incubated with this solution for 3.5 hours at 40° C. with perturbation. After incubation, samples were washed with 100% acetic anhydride (Fisher Chemical), 12 N hydrochloric acid (Fisher Chemical), and 0.2 M sodium bicarbonate in succession. After rinsing with copious amounts of water, samples were sonicated in 4 M urea for 10 min followed by 1 M NaCl for 10 min. Samples were rinsed with copious amounts of water and dried at 100° C. for 1 h.

Materials and Methods

PA Preparation

PAs were co-assembled at different percentages with $C_{16}$-$V_2A_2E_2$ filler PA ($E_2$) by dissolving the lyophilized powder in hexafluoroisopropanol (HFIP) and mixing for 15 min. Samples were frozen in liquid $N_2$, and HFIP was removed in vacuo. Samples were then re-dissolved using several microliters of 1N NaOH in distilled deionized water. These solutions were frozen in liquid $N_2$ and lyophilized to remove any residual HFIP. The co-assembled peptide amphiphile powder was reconstituted in 125 mM NaCl and 3 mM KCl solution. It was then adjusted to a pH of 7.4 using 1 μL additions of 1N NaOH. Samples were annealed at 80° C. for 30 min, then slowly cooled at 1° per minute to reach a final temperature of 27° C.

PA Gel Preparation

Gels were made using annealed PAs prepared with methods described herein 1. BDNF native protein or BDNF peptide were incorporated by mixing at 10 nM or 0.5 uM respectively, with $E_2$ Filler PA gel at 1 wt % while it was in its liquid state. Silicon isolators with adhesive (Invitrogen) were placed on PDL coated glass coverslips. 70 μL of PA liquid was pipetted into the circular silicon well and a Transwell insert was placed flush with the top of the well of the silicon insert. This step ensured a flat, even thickness for all gels. Gelling solution comprised of 125 mM NaCl, 3 mM KCl, and 25 mM $CaCl_2$ was pipetted into the Transwell insert and allowed to slowly soak down into the material from the top. The insert prevented the gel from swelling more than the thickness of the silicon isolator. All gels were incubated at 37° C. for 5 min before removing the Transwell insert.

Material Characterization

Cryogenic-Transmission Electron Microscopy. Samples were plunge-frozen using a Vitrobot Mark IV (FEI) vitrification robot. Samples at 1 w/v % were tenfold diluted to 0.1 w/v % immediately before 7.5 μL of sample solutions were transferred to plasma-cleaned 300-mesh copper grids with lacey carbon support (Electron Microscopy Science). Samples were blotted at room temperature with 95-100% humidity and plunge frozen into liquid ethane. Samples were transferred into a liquid nitrogen bath and placed into a Gatan 626 cryo-holder through a cryo-transfer stage. Cryo-TEM was performed using a liquid nitrogen-cooled JEOL 1230 TEM working at 100 kV accelerating voltage. Images were acquired using a Gatan 831 CCD camera.

2.2.2. Dynamic Light Scattering (DLS). Measurements were performed on a Malvern Zetasizer Nano ZSP light scattering spectrometer. Samples were prepared as previously described. During the sample measurement, the temperature was kept at 25° C. The sample was equilibrated for 30 seconds before each measurement was taken. The duration of each measurement was 10 seconds and the measurement angle was 173° backscatter. The attenuator was determined by the instrument automatically, as was the number of accumulations for each run. Each measurement run was repeated 3 times.

Small-angle X-ray scattering (SAXS). Experiments were performed at beamline 5-ID-D of the DuPont-Northwestern-Dow Collaborative Access Team (DND-CAT) Synchrotron Research Center at the Advanced Photon Source, Argonne National Laboratory. PA samples were prepared at 1 w/v % in 1.5 mm quartz capillaries (Charles Supper) and irradiated for 2 seconds. Data was collected with an X-ray energy at 17 keV (1=0.83 Å), and the SAXS CCD detector (MAR) was positioned 245 cm behind the samples to record the scattering intensity in the interval 0.001<q<0.20 Å−1. The wave vector q is defined as $=(4\pi/\lambda) \sin(\theta/2)$, where θ is the scattering angle. Azimuthal integration (Fit2D) was used to average 2D scattering images to produce 1D profiles of intensity versus q. A capillary containing only solvent was tested as well and this graph was subtracted from the corresponding data using IgorPro software. Using NCNR analysis macro in IgorPro, $E_2$ filler PA, 100% BDNF PA, 10% BDNF PA and 10% Linear BDNF PA were fitted to a lamellar head-to-tail form factor model, spherical model, and cylindrical core shell model respectively.

Scanning Electron Microscopy (SEM) PA gels or sample coverslips were fixed in 4% paraformaldehyde (PFA) for 20 minutes. They were rinsed with PBS and dehydrated by incubation in a series of ethanol solutions of increasing concentration. Ethanol was subsequently removed by critical point drying (Tousimis Samdri-795). Dehydrated samples were mounted on stubs using carbon glue and coated with 16 nm of osmium (Filgen, OPC-60A) to create a conductive sample surface. All SEM images were taken using a Hitachi SU8030 or LEO 1525 instrument operating at an accelerating voltage of 2 kv.

Rheological Measurements. PA materials were prepared using methods described above. An Anton Paar MCR302 Rheometer with a 25 mm cone plate was used for all rheological studies. 150 μL of PA liquid was placed on the sample stage and 30 μL of 150 mM $CaCl_2$ solution (final concentration 25 mM) was placed on the sample plunger positioned above the material. The instrument was set to 37° C. The plunger was lowered to the measuring position and a humidity collar was added to prevent sample evaporation. The sample was equilibrated for 30 minutes with a constant angular frequency of 10 [rad/s] and 0.1% strain. The angular frequency was then decreased incrementally from 100 rad/s to 1 rad/s over 21 points and the storage and loss modulus were reported. Lastly, the % strain was increased incrementally from 0.1 to 100% over 31 points and the storage and loss modulus were recorded.

In Vitro Studies

Animal Protocol. All animal housing and procedures were performed in accordance with the Public Health Service Policy on Humane Care and Use of Laboratory Animals. All procedures were approved by the Northwestern University Institutional Animal Care and Use Committee. Timed pregnant CD1 mice were supplied by Charles River Laboratories (Wilmington, MA).

2.3.2. Dissection of Embryonic Primary Cortical Neurons. Neurons were obtained from embryonic brains as described elsewhere.[2] Briefly, time-pregnant mouse was sacrificed by cervical dislocation and the embryos were extracted at embryonic day 16 (E16). Cerebral cortices were dissected from the mouse embryos and meninges were removed in a solution of Hank's Balanced Salt Solution (HBSS) with 1% pen-strep (Invitrogen) and then digested with trypsin (Invitrogen) and DNAse (Sigma-Aldrich) for 10 min at 37° C. The tissue was mechanically dissociated, centrifuged at 1000 g for 5 min, and resuspended in $CO_2$-equilibrated Neurobasal (NB) neuronal culture medium (Invitrogen) supplemented with 10% normal horse serum (NHS) (Invitrogen), 1% pen-strep (Invitrogen), 0.5 mM L-glutamine (Invitrogen), and 5.8 μL $NaHCO_3$/mL (Sigma-Aldrich). The cell suspension was pre-plated at 37° C. for 30 min. Afterwards, the supernatant was collected, passed through a cell strainer with 100 μm pore size and centrifuged at 1000 g for 5 min. The pellet was resuspended in NB neuronal culture medium (1% NHS, 1% pen-strep, 0.5 mM L-glutamine, 22 μM glutamic acid (Sigma-Aldrich), 2% B27 (Gibco), and 5.8 μL $NaHCO_3$/mL (Sigma-Aldrich), and plated at different densities (depending on the type of experiment, see below) directly on tissue culture plates coated with poly-D-lysine (Sigma-Aldrich). After 24 hs, the medium was replaced with serum-free neuronal culture medium (1% pen-strep, 0.5 mM L-glutamine, 2% B27, 5.8 μL $NaHCO_3$/mL). Under these conditions, we obtained a neuron-enriched culture with a composition of approximately 10% glial cells.

BDNF PA Treatments and Cell Culture Procedures. Treatments were prepared by dissolving PA (including $E_2$ Filler, $E_2$ Filler+$E_4$PEG, $E_2$ Filler+Linear BDNF, $E_2$ Filler+BDNF PAs) and BDNF peptide at different concentrations (0.5, 1.0 or 5.0 μM), in media without serum or B27 supplement or starvation media. Unless otherwise noted, BDNF PA, Linear BDNF PA, or $E_4$PEG PAs were co-assembled at 10 mol % with $E_2$ filler PA (total concentration of PA was 5.0, 10.0, or 50.0 μM respectively). For the co-assembly ratio study, BDNF PA was co-assembled at 10, 20, 50, 70, 90, and 100 mol %. Human/Murine/Rat BDNF protein (Peprotech) was resuspended at different concentrations (0.25, 0.5 and 1 nM) in starvation media.

For morphometric analysis and cell viability assays, cells were cultured in 24 or 48 well plates at a density of 25,000 or 40,000 cells/well respectively, for three days before being treated. Cells were then treated for 24 hours, 3 days or 7 DIV. Samples were fixed in 4% PFA for 15 min (20 min for gels) at room temperature (RT) for immunofluorescence studies.

For western blot, cells were cultured in 6 well plates at a density of approximately 900,000 cells/well for 14 DIV before being treated. Treatments were added for 2, 4, 6, 8, 12 or 24 h in vitro before protein was harvested. For TrkB inhibitor studies, cells were cultured for 14 DIV and then treated with a TrkB specific inhibitor, K-252a (Sigma Aldrich), for 1 hour prior to being treated with the different conditions mentioned above. Protein was extracted after six hours of treatment.

Biological Assays

Western Blot. Protein was extracted from primary neuronal cultures with Halt Protease and Phosphatase Inhibitor Cocktail (Thermo Scientific) and a BCA assay (Thermo Scientific) was performed to determine protein content of each sample. Cell protein was loaded into and separated using a 4-20% SDS-PAGE gel (Bio-Rad). It was then electrotransferred from the gel to a nitrocellulose membrane (Bio-Rad). The membranes were blocked with 5% milk solution (Bio-Rad) for 30 minutes followed by an overnight incubation with primary antibodies at 4° C. The following primary antibodies were used: rabbit anti-pTrkB (1:1000, Cell Signaling), rabbit anti-TrkB (1:1000, Cell Signaling), rabbit anti-Actin (1:2000, Sigma Aldrich), mouse anti-Actin (1:2000, Sigma Aldrich), rabbit anti-pPLCγ (1:1000, Cell Signaling), rabbit anti-PLCγ (1:1000, Cell Signaling), rabbit anti-pAKT (1:2000, Cell Signaling), mouse anti-AKT (1:2000, Cell Signaling), rabbit anti-pERK1+ERK2 (1:1000, Abcam), rabbit anti-ERK 1/2 (1:1000, Cell Signaling), rabbit anti-PSD95 (1:1000, Abcam), rabbit anti-MAP-2 (1:2000, BioLegend), and mouse anti-Tuj-1 (1:1000, BioLegend). Membranes were then incubated with their corresponding secondary HRP-conjugated antibodies (1:1000; ThermoFisher). Protein signals were detected using Radiance Bioluminescent ECL substrate (Azure Biosystems). Densitometry analysis, standardized to total receptor content or Actin as a control for protein loading, was performed using ImageJ software.[3] For quantification, triplicate samples were analyzed and at least two different experiments were conducted.

Immunofluorescence. For immunofluorescence, fixed samples (4% PFA for 15 min at RT) were incubated with primary antibodies overnight and Alexa 488 or Alexa 555 secondary antibodies (1:2000, Invitrogen) were used for 2 h at room temperature. The following primary antibodies were used: mouse anti-Tuj-1 (neuronal marker 1:4000, BioLegend), rabbit anti-Tuj-1 (neuronal marker, 1:4000, BioLegend) rabbit anti-MAP2 (marker for mature neurons 1:2000, BioLegend), mouse anti-SMI312 (axonal filament marker 1:1000, BioLegend), rabbit anti-Synaptophysin (marker for synaptic vesicles, 1:1000, Abcam) and DAPI (nuclear stain, 1:2000, Invitrogen). If not already in a glass bottom plate (MatTek), the preparations were mounted with Immu-Mount (Thermo Scientific) for imaging.

Imaging and Morphometric Analysis. Throughout the experiments, a digital camera (Nikon) mounted on a tissue culture microscope was used to take bright field images of cells. Nikon A1R confocal laser-scanning microscope with GaAsP detectors was used to visualize and image fluorescent preparations. Images were processed using an ImageJ (National Institutes of Health) plugin. Confocal images were reconstructed by NIS Elements Advanced Research Microscope Imaging software (version 4.20) or Imaris program (version 8.1, Bitplane Scientific software) for 3D interactive data viewing with normal or shadow projections of cells screened under Nikon A1R confocal laser-scanning microscope with GaAsP detectors.

For morphometric analysis, NeuronJ was used to trace and measure neuronal extensions.[4] For quantification of number of primary neurites and neurite length, a minimum of 60 randomly selected cells were analyzed with a minimum of 2 independent batches of culture for each condition. The images were arranged in Adobe Photoshop (v.7.0), with adjustments for contrast, brightness and color balance to obtain optimal visual reproduction of data.

Flow Cytometry and Cell Viability. Cells were carefully washed three times with 1×PBS. Each well was incubated with 200 μL trypsin until cells detached (did not exceed 10 min of incubation). Cells were then resuspended in 600 μl of media to neutralize the trypsin and were centrifuged for 15 mins at 1.2 rpm. Supernatant was removed, and the pellet was resuspended in approximately 40 μl of media before Flow Cytometry (BD LSRFortessa) was performed. DAPI (Sigma, 5 μg/mL) was added 1-3 min before measurements were taken to determine the absolute number of dead cells (excitation wavelength of 405 nm). Cell populations were gated based on cell size (FSC), granularity of the cytoplasm (SSC), multiple cells (FSC-W), UV fluorescence (DAPI filter). Percentage of positive cells was calculated from alive cells (DAPI negative). All the samples were measured in triplicates. Results were analyzed using FlowJo software.

Cell culture on Immobilized Peptide and Viability Assay. For immobilized peptide studies, cells were cultured on blank, BDNF peptide, or APTES coated glass coverslips for 5 days in vitro (DIV). Media was removed, and cells were rinsed once with HBSS. A calcein-AM/ethidium homodimer-1 live/dead assay (Invitrogen) was used to assess cell viability. Calcien-AM/ethidium homodimer-1 solution in HBSS was added to each well for 20 min at RT. The solution was removed, and samples were rinsed 1 time with HBSS before coverslips were mounted for imaging.

Electrophysiology—Multi Electrode Array (MEA) Plates. For 2D electrophysiology studies, 12 well MEA plates with 64 electrodes per well were coated with PEI and laminin according to Axion Biosystems protocols.[5] Embryonic primary neurons were seeded at a density of 60,000 cells/well and cultured during 14 DIV. On day 14, cells were treated with BDNF protein, BDNF PA, BDNF Peptide, or starvation media. Every 5 days, half of the media was removed from each well and replaced with fresh media containing additional treatment. Spontaneous network and synchronized activity was recorded using Axion Biosystems Maestro 768 channel amplifier and Axion Integrated Studios (AxIS) v2.4 software. The amplifier recorded from all channels simultaneously using a gain of 1200× and a sampling rate of 12.5 kHz/channel. After passing the signal through a Butterworth band-pass filter (300-5000 Hz) on-line spike detection (threshold=6× the root-mean-square of noise on each channel) was done with the AxIS adaptive spike detector. All recordings were conducted at 37° C. with appropriate 5% $CO_2$/95% $O_2$. Spontaneous network activity was recorded for 5 min each day starting at 10 DIV. Active electrodes were defined as having >5 spikes/min and only wells with over 10 active electrodes during the baseline-recording period were used in the analysis. Synchronized activity was defined as spike and burst activity that occurred on 25% of the electrodes or more in a well within 100 ms of each other. The mean firing rate (Hz), network burst duration (sec), and number of spikes per network burst were used as a measure of neuronal activity as this demonstrates maturity of neuronal functional properties. All data reflects well-wide averages, where the reported value of n represents the number of wells per condition.

Infiltration Study. Gels were prepared as described in 2.1.2. Gels were then rinsed with media one time before cells were seeded on top at a density of approximately 42,000 cells/well. Cells were cultured for one week in vitro. Half of the gels were analyzed by patch clamp analysis (see section 3.4.9. Other gels were fixed with 4% PFA to perform infiltration studies. Cell were stained for MAP2, TUJ-1 and DAPI using immunocytochemistry methods described previously. Confocal microscopy was used to make z-stack reconstructions of each gel. The MultiMeasure function in the ROI manager of ImageJ was used to measure the depth of pixels for each channel which was then plotted as intensity vs depth in the gel. The average intensity of MAP2 was measured by averaging the mean intensities obtained from maximum intensity projections of z-stacks images of gels.

Patch Clamp. Whole-cell current-clamp recordings were made from visually identified primary cultured neurons using inverted Olympus IX51 microscope equipped with a 40× objective. Recording pipettes were made of glass capillaries using a horizontal Sutter P-1000 puller yielding a 3-5 MΩ resistance pipette when filled with standard intracellular solution containing (in mM): 120 K-$MeSO_4$, 10 KCl, 10 HEPES, 10 $Na_2$-phosphocreatine, 4 Mg-ATP, 0.4 $Na_3$-GTP, pH 7.3; 285-290 mOsm. Gels with neurons were continuously perfused with standard oxygenated aCSF bath solution (in mM): 125 NaCl, 26 $NaHCO_3$, 2.5 KCl, 1.25 $NaH_2PO_4$, 1 $MgSO_4$, 25 glucose, 2 $CaCl_2$, pH 7.4 at 32-34° C. Whole-cell current-clamp data was acquired using an Multiclamp 200B amplifier (Molecular Devices, USA) and digitized at 10 kHz (filtered at 3 kHz) with the neurons held at −65 mV. Resting membrane potential was measured immediately after breaking into the cell. Input resistance was calculated as the slope of the voltage-current curve using 500 ms current steps from −50 pA to 30 pA at 10 pA steps. There were no differences in resting membrane potentials or input resistance between the three groups. AP amplitudes, thresholds, half-widths and fAHP measures were taken from ramp current injection steps. AP threshold was calculated where the first derivative of the up phase of the trace equals 5 mV/ms. Neurons meeting our quality criteria were used: series resistance <30 MΩ, membrane resistance >100 MΩ, resting potential <−40 mV, and AP amplitude >65 mV from holding. Data was analyzed using MATLAB protocols designed specifically for these experiments.

Statistical Analysis

All error bars indicate the standard error of the mean. Statistical analysis was performed using Graphpad Prism v.6 software. Analysis of variance (ANOVA) with a Bonferroni post hoc test was used for all multiple group experiments. P values <0.05 were deemed significant.

Results

Design and Characterization of BDNF Mimetic PAs

The bioactive portion of an exemplary BDNF peptide used in experiments conducted during development of embodiments herein comprises of three amino acids (lysine, lysine, arginine) cyclized using a D-Proline to ensure the correct steric conformation for receptor binding (FIG. 1a). The BDNF peptide developed by the Hughes lab also contained a non-bioactive alanine which they replaced with a lysine without significant effects on BDNF mimicry (Ref 32; herein incorporated by reference in its entirety). For the design of the BDNF PA, the lysine was used to link the BDNF peptide to a hexa-polyethyleneglycol (PEG6) spacer to increase the distance of the BDNF epitope from the PA nanofiber surface and enhance signal bioavailability (FIG. 1b) (Ref 33; herein incorporated by reference in its entirety). The PA backbone was designed with four glutamic acids (e.g., the charged portion) followed sequentially by two valine residues and two alanine residues (e.g., the structural portion) ($E_4V_2A_2$), and an alkyl tail of 16 carbons ($C_{16}$) (Ref 34; herein incorporated by reference in its entirety). The four glutamic acids enhance solubility of the PA molecule while $V_2A_2$ and $C_{16}$ created the nanostructure via β-sheet formation and hydrophobic collapse, respectively. A non-cyclized BDNF PA (Linear BDNF PA) was synthesized as a control to probe the specificity of peptide conformation on receptor binding (FIG. 1c).

Figure 6:
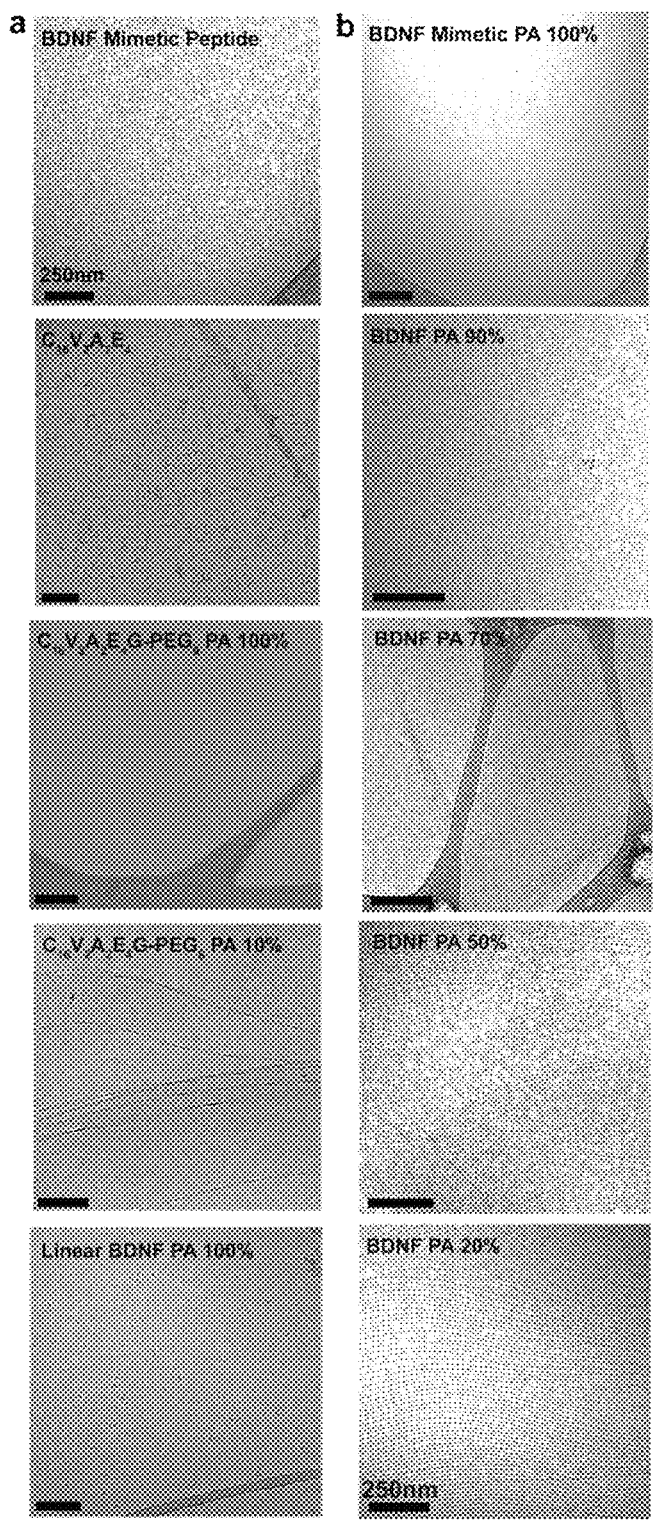
FIG. 6. Cryo-TEM of synthesized materials and different co-assembly ratios. (a) BDNF Peptide, PA backbones; $E_4$ Filler, $E_4$PEG Filler, $E_4$PEG PA co-assembled with $E_2$ Filler at 10 mol %, and Linear BDNF PA at 100%. (b) Co-assembled ratios of BDNF PA with $E_2$ Filler PA 100% to 20%.
Figure 7:
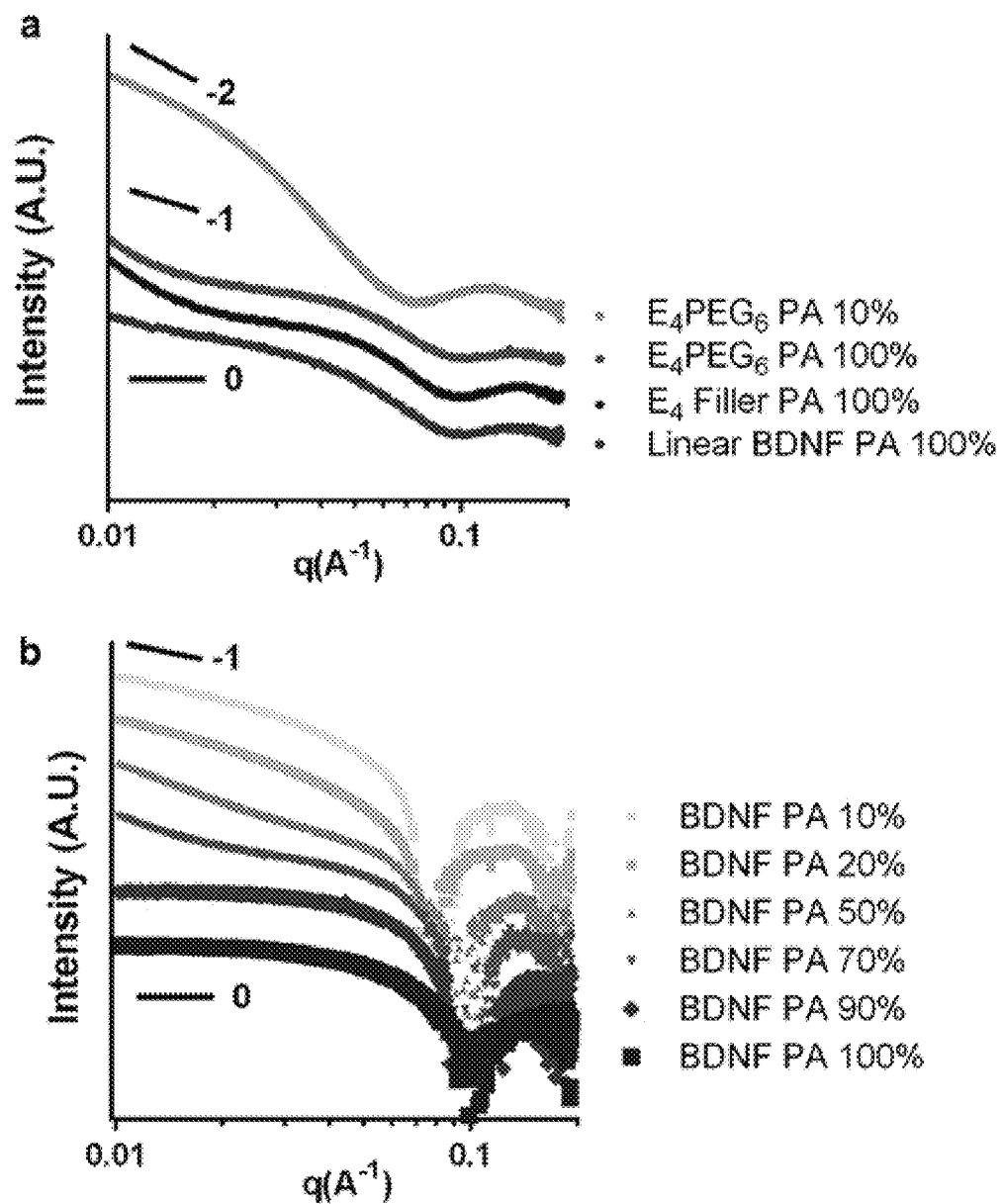
FIG. 7. Small Angle X-Ray Scattering data of various PA conditions. (a) BDNF Peptide, PA backbones; $E_4$ Filler, $E_4$PEG Filler, $E_4$PEG PA co-assembled with $E_2$ Filler at 10 mol %, and Linear BDNF PA at 100%. (b) Co-assembly ratios of BDNF PA with $E_2$ Filler PA 100-0 mol %.

Cryogenic transmission electron microscopy (Cryo-TEM) demonstrated that the BDNF PA and the Linear BDNF PA alone (100 mol %) were unable to form nanofibers likely due to the large steric demands of the BDNF epitope (FIG. 1e). Dynamic light scattering (DLS) confirmed that the BDNF PA forms micelles with a diameter distribution centered on 12 nm (FIG. 1f). To optimize fiber formation, different co-assembly ratios (10, 20, 50, 70 and 90 mol %) of the BDNF PA with a non-bioactive $C_{16}V_2A_2E_2$ PA (E2 Filler PA) were analyzed. The E2 filler peptide forms robust nanofibers (FIG. 1c). It was also found that the BDNF PA backbone components, $C_{16}V_2A_2E_4$ (E4 Filler PA) or $C_{16}V_2A_2E_4$PEG-6 (E4PEG PA), were unable to form fibers (FIG. 6). It was observed that as the co-assembly ratio of the BDNF PA to E2 Filler PA was increased, the propensity to form fibers decreased significantly, indicating the enhancement of fiber formation by the E2 filler PA in (FIGS. 1H-I & 6). To corroborate these findings, the co-assembled PA solutions were analyzed by small angle x-ray scattering (SAXS), which provided a more precise comparison of nanostructural features (FIGS. 1J & 7A). The SAXS curve of the E2 Filler PA showed a slope of −2 in the Guinier region indicating ribbon-like fibers and fit a lamellar head-to-tail form factor model (FIG. 1J). BDNF PA co-assemblies (10-70 mol %) exhibited a slope of −1, indicating cylindrical nanofibers and fit a cylindrical core shell model (FIG. 7B). Conversely, 100 mol % BDNF PA solutions exhibited a slope of 0 in the Guinier region corresponding to spherical nanostructures (FIGS. 1J & 7B) which confirms the micelles observed using DLS (FIG. 1E).

Cellular Response to BDNF PAs

Experiments were conducted during development of embodiments herein to evaluate the mimicry of an exemplary BDNF PA by analyzing its effect on embryonic primary mouse cortical neurons in vitro. 10 mol % of the BDNF PA, Linear BDNF PA, or $E_4$PEG PA were co-assembled with 90 mol % E2 Filler PA and then thermally annealed at 1 wt % to induce fiber formation. These co-assemblies are referred to as BDNF PA, Linear BDNF PA or E2+$E_4$PEG PA respectively. PA treatments were dissolved in media and added to cells after 14 days in vitro (DIV). Scanning electron microscopy (SEM) and fluorescent confocal microscopy confirmed that the PA fibers in media interacted with neural cells (FIGS. 2A & 8A-C).

Figure 2:
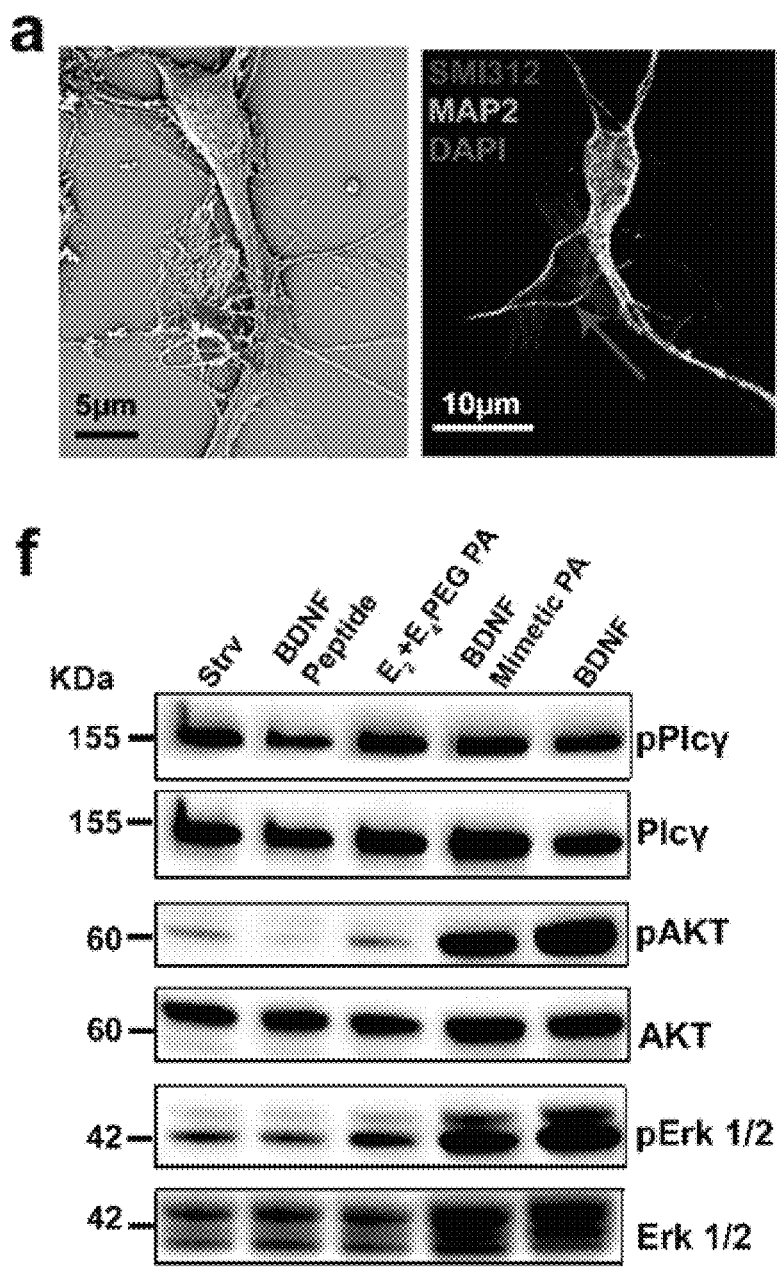
FIG. 2. TrKB receptor activation and mediated downstream pathway analysis of primary cortical neurons treated with BDNF PA. (a) SEM micrograph (left) and confocal micrograph (right) showing a cortical neuron treated with PA nanofibers (arrow). Cells were stained for SMI312 (axonal marker), MAP2 (dendritic marker), and DAPI (nuclei). (b) Western blot of phosphorylated TrKB (p-TrKB), and total TrKB receptor in neural cells treated with BDNF PA and BDNF protein over 24 h in vitro. (c) Densitometry analysis of p-TrkB of conditions shown in (b). Intensity values normalized to total TrKB. (d) Western blot of p-TrkB, and total TrKB receptor in neural cells treated with starvation media (Strv), BDNF Peptide, different PA conditions ($E_2$ Filler PA, $E_2$+$E_4$PEG, Linear BDNF and BDNF PA) and BDNF protein for 6 h in vitro. (e) Densitometry analysis of p-TrkB of conditions shown in (d). Intensity values normalized to TrkB. (f) Western blot showing phosphorylated and total activation of BDNF downstream pathway effectors: PlCyγ, AKT and ERK 1/2 in neural cells treated with Strv, BDNF peptide, $E_2$+$E_4$ PEG PA, BDNF PA and BDNF protein for 6 h in vitro. (g) Densitometry analysis of phosphorylated proteins normalized to total protein shown in (f). *$P<0.05$, $P<0.01$, $P<0.001$, and ****$P<0.0001$, LSD test (b-g) (n=3).
Figure 2:
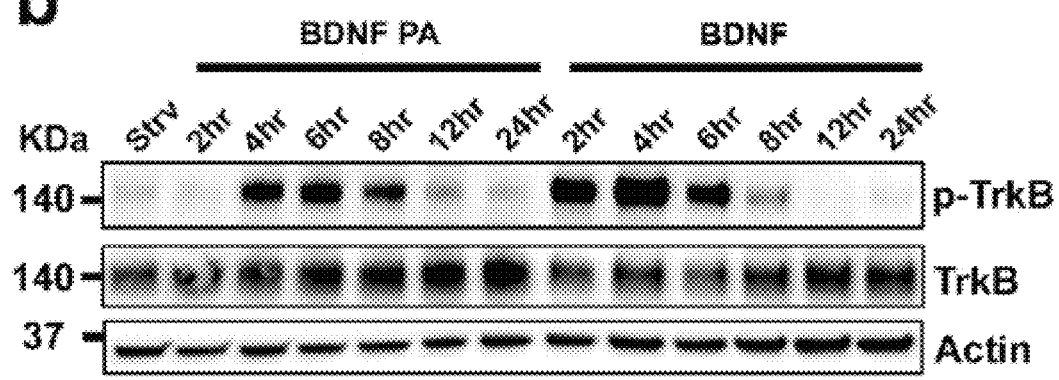
Figure 2:
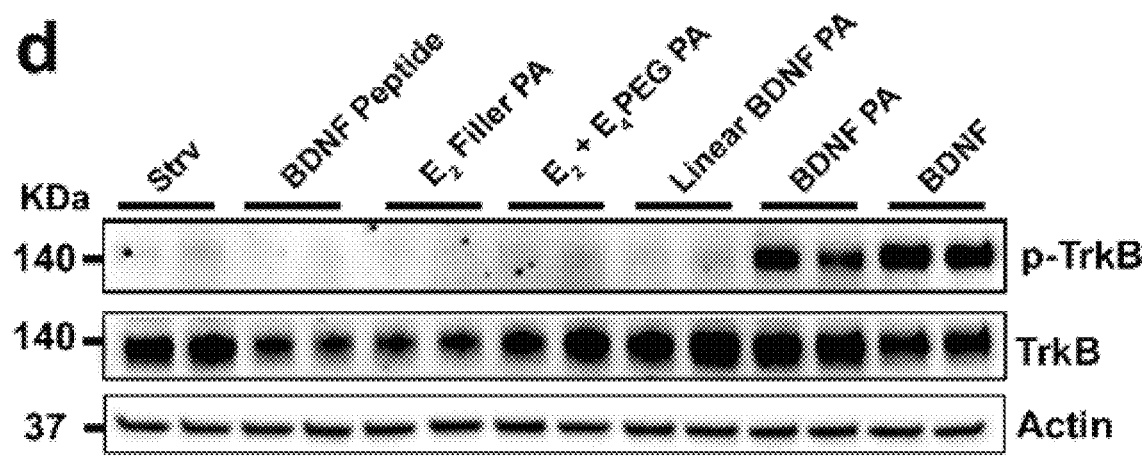
Figure 2:
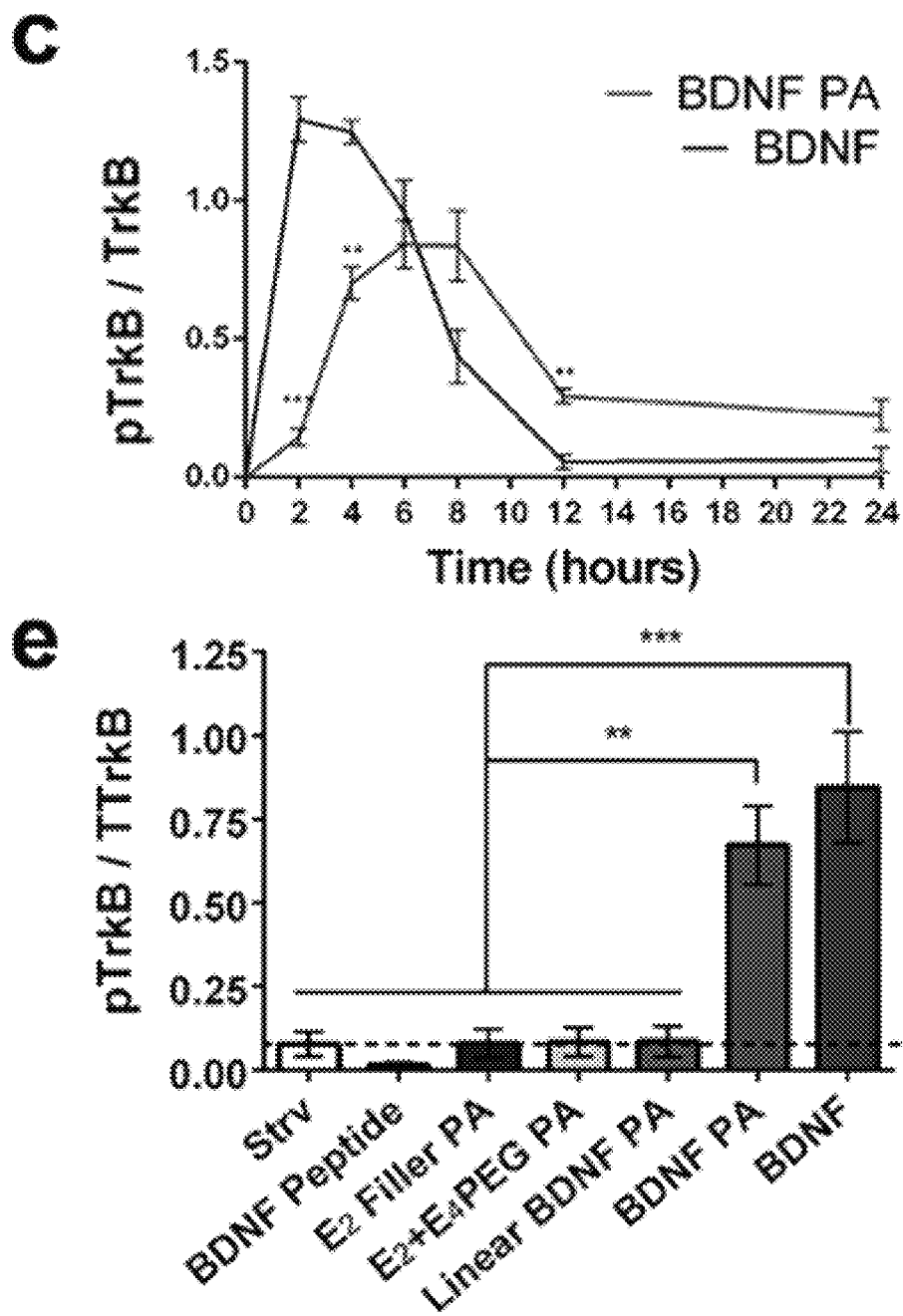
Figure 2:
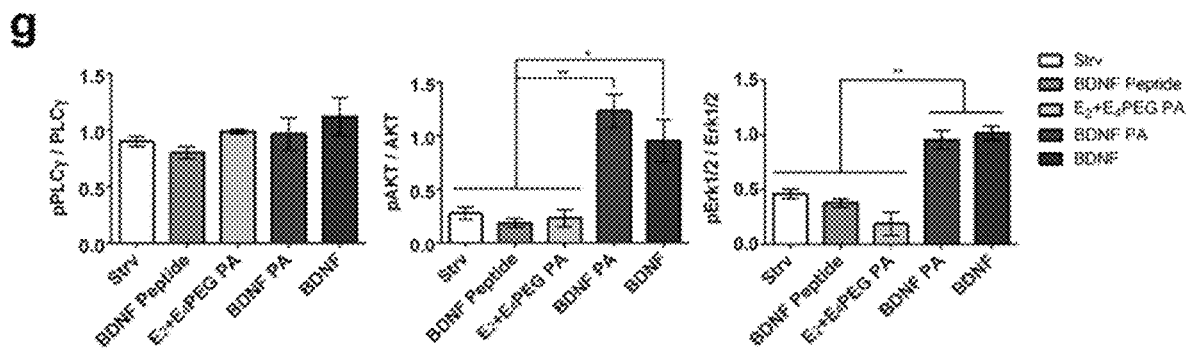
Figure 8:
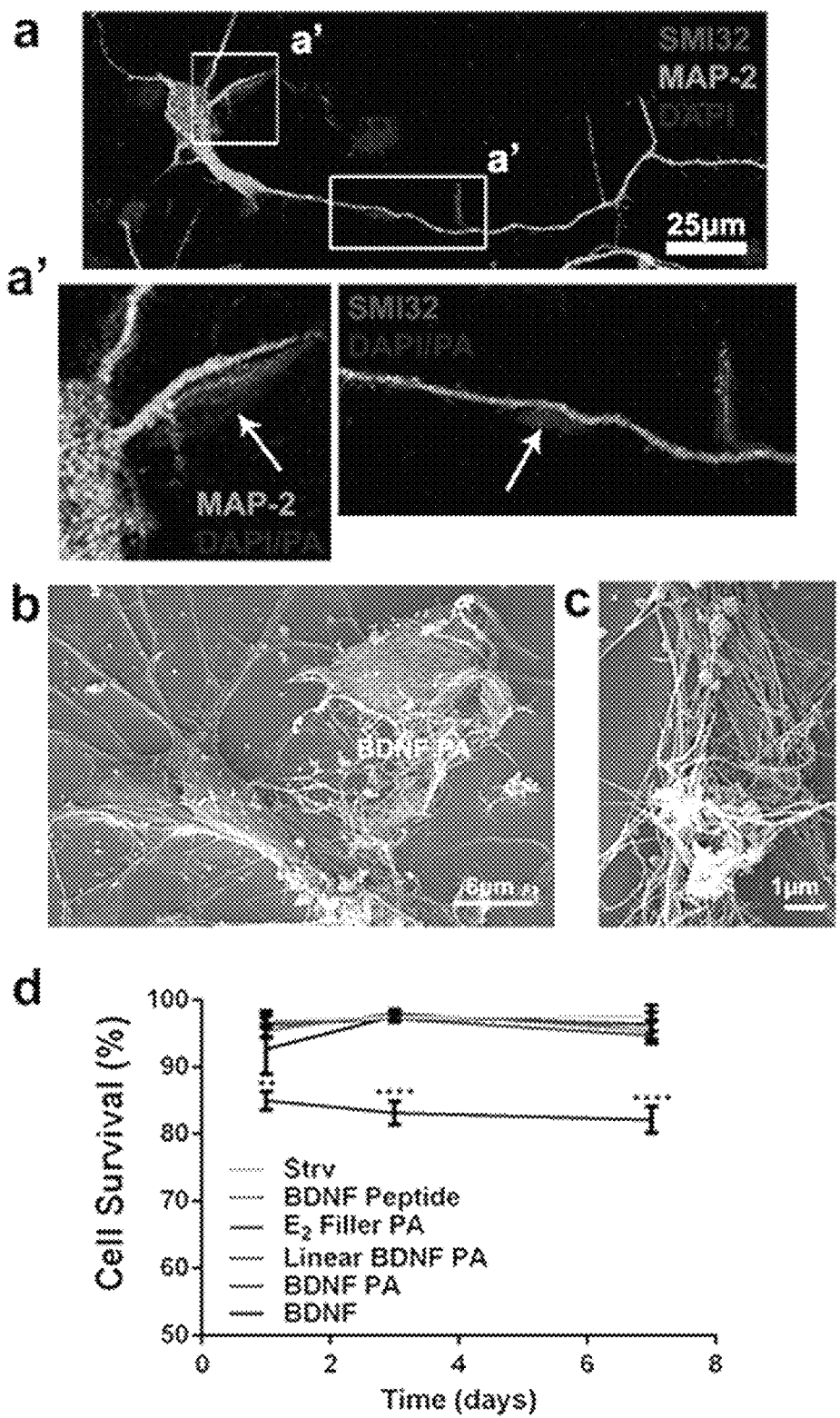
FIG. 8. PA fiber-cell interaction and cell viability assay of primary cortical neurons. (a) Confocal micrograph showing a cortical neuron treated with PA nanofibers (in blue). Staining for SMI312 (axonal marker), MAP2 (dendritic marker), and DAPI (nuclei). (a') Inset of (a) showing PA fibers interacting with the axon and dendrites of a neuron after being treated for 72 h in vitro. (b) SEM micrograph of BDNF PA interacting with primary cortical neurons at 72 h in vitro. (c) BDNF PA fiber mesh. (d) Percentage of neuronal cell survival treated with various conditions for 24 h, 3 and 7 DIV. *$P<0.05$, $P<0.01$, *$P<0.001$, and ****$P<0.0001$, LSD test (d) (n=3).
Figure 9:
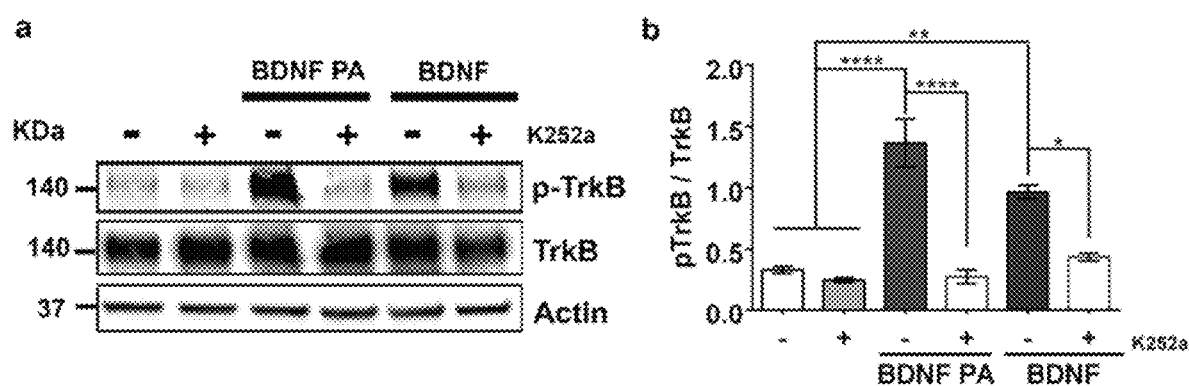
FIG. 9. K252a inhibitor study. (a) Western blot of phosphorylated TrKB (p-TrKB) and total TrkB receptor in neural cells treated with (−) starvation media and (+) K252a, in the presence of BDNF PA or BDNF native protein at 6 h. Cells were treated with K252a 2 h prior to treatment. (b) Densitometry analysis of p-TrkB of the conditions shown in (a). (Intensity values normalized to TrkB). *$P<0.05$, $P<0.01$, *$P<0.001$, and ****$P<0.0001$, LSD test (n=3).

To determine the ability of the BDNF PA to activate the TrkB receptor, which native BDNF protein binds to with high affinity (Refs. 6-8; herein incorporated by reference in their entireties), the receptor activation kinetics were analyzed using western blot analysis at different time points. The BDNF PA was added to the media (with an epitope concentration of 0.5 μM) for 2, 4, 6, 8, 12 and 24 h and compared to the addition of BDNF protein at a dose of 0.25 nM 35, 36 (8 ng/mL) at the same timepoints (FIG. 2B). Neuronal cells treated with BDNF protein showed an initial peak in phosphorylated TrkB (p-TrkB) between 2 and 4 h, which then begins to decrease with cells no longer showing p-TrkB after 12 h (FIG. 2C). On the other hand, cells treated with BDNF PA showed a peak in p-TrkB between 4 and 6 h. It is contemplated that this delay in the initial activation is due to faster diffusion of the BDNF protein in comparison with the BDNF PA nanofibers, which require additional time to contact the cells. Experiments conducted during development of embodiments herein also demonstrated that the BDNF PA and BDNF protein induced similar levels of p-TrkB 6 h post-treatment. To exclude the possibility of any cytotoxic effect of the PAs, a cell viability assay was performed on primary cortical neurons (3 DIV) for 1, 3, and 7-day timepoints (FIG. 8D). The cell survival remained above 80% for all conditions, which is indicative of a healthy primary culture (Ref 37; herein incorporated by reference in its entirety). To define the molecular mechanisms involved in the activity-dependent regulation of sustained TrkB signaling, cortical neurons were pre-treated with the pharmacological inhibitor K252a (Ref 38; herein incorporated by reference in its entirety), for 2 h prior to treatment with BDNF PA or BDNF protein. Western blot analysis showed that both BDNF PA and BDNF protein-induced TrkB phosphorylation was completely blocked by K252a 6 h post-treatment (FIG. 9). The results indicate that the BDNF PA not only activates the TrkB receptor but does so through a similar mechanism as the BDNF protein.

Figure 10:
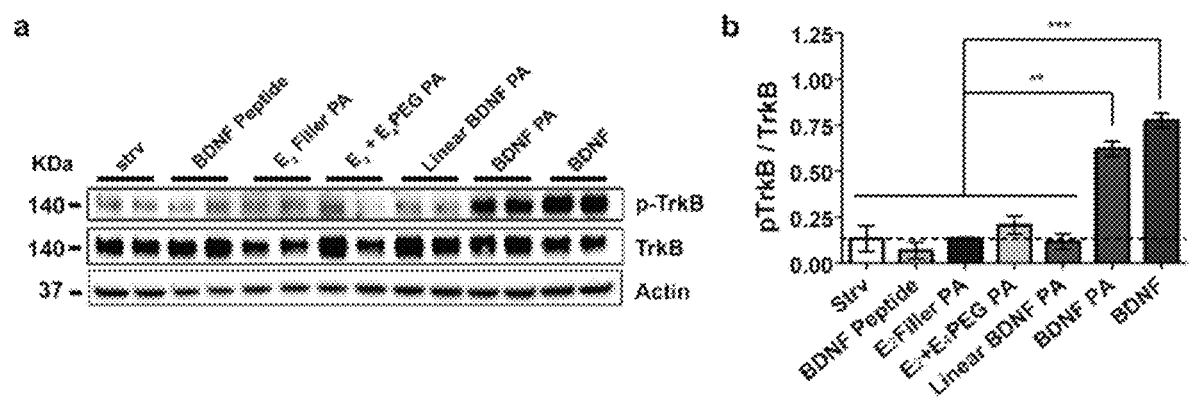
FIG. 10. TrkB receptor activation study at 4 hours. (a) Western blot of p-TrkB and total TrkB receptor in neural cells treated with BDNF peptide, $E_4$PEG PA co-assembled at 10 mol % with $E_2$ Filler PA, Linear BDNF PA, BDNF PA, and BDNF native protein during 4 h in vitro. (b) Densitometry analysis of p-TrkB of the conditions shown in (a). (Intensity values normalized to TrkB). *$P<0.05$, $P<0.01$, *$P<0.001$, and ****$P<0.0001$, LSD test (n=3).
Figure 11:
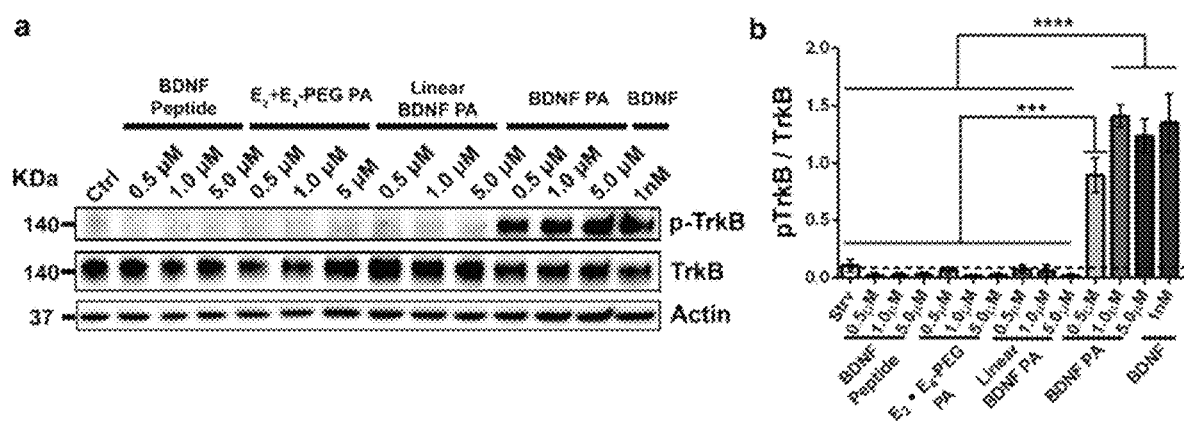
FIG. 11. TrkB receptor activation concentration dependence study. (a) Western blot of p-TrkB and total TrkB receptor in neural cells treated with 0.5, 1.0 and 5.0 μM of BDNF peptide, $E_4$PEG PA co-assembled at 10 mol % with $E_2$ Filler PA, Linear BDNF PA, BDNF PA, and BDNF native protein during 6 h in vitro. (b) Densitometry analysis of p-TrkB of the conditions shown in (a). (Intensity values normalized to TrkB). *$P<0.05$, $P<0.01$, *$P<0.001$, and ****$P<0.0001$, LSD test (n=3).

Experiments were conducted during development of embodiments herein to examine the nature of the TrkB receptor activation in the exemplary PA systems herein. All the components of the BDNF PA (BDNF Peptide, E2 Filler PA, and E2+E4PEG PA) as well as the Linear BDNF PA were studied in parallel. At 4 and 6 h timepoints, none of these control conditions were able to induce TrkB phosphorylation (FIGS. 2D & 10). The lack of TrkB phosphorylation in the presence of the Linear BDNF PA indicates that the cyclic representation of the BDNF mimetic epitope is crucial in receptor-ligand binding and therefore activation. Consistent with previous work (Ref 24; herein incorporated by reference in its entirety), the BDNF peptide alone did not show activation of the TrkB receptor, indicating that the PA nanofiber system plays a role in the presentation of the BDNF epitope to the cell. Neuronal cells treated with increasing concentrations of BDNF PA (0.5, 1.0, and 5.0 µM) showed no dose-dependent activation of TrkB (FIG. 11), indicating that the 0.5 µM dose is sufficient to activate the total amount of TrkB receptor present in the cell. Furthermore, none of the control conditions induced TrkB activation at higher concentrations (1.0 and 5 µM). These results indicate the necessity of specific BDNF signal conformation and presentation in its receptor binding ability.

Figure 12:
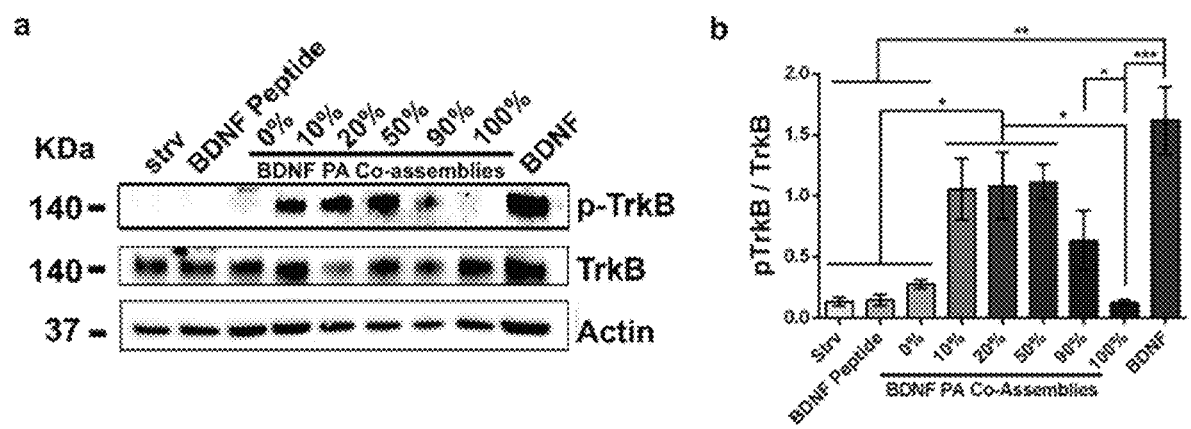
FIG. 12. TrkB receptor activation study with different co-assembly ratios of BDNF PA to $E_2$ Filler PA. (a) Western blot of phosphorylated TrkB (p-TrkB) and total TrkB receptor in neural cells treated with starvation media, BDNF Peptide, and BDNF PA co-assembled with $E_2$ Filler PA at 0, 10, 20, 50, 90, 100 mol %. (b) Densitometry analysis of p-TrkB of the conditions shown in (a). (Intensity values normalized to TrkB). *P<0.05, P<0.01 and *P<0.001, LSD test (n=3).
Figure 13:
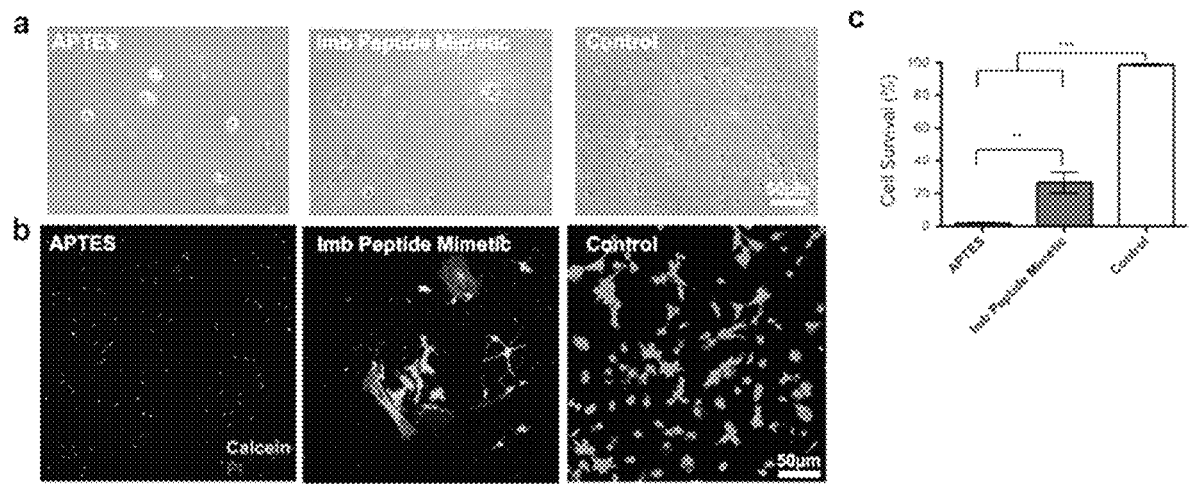
FIG. 13. Viability assay of cells cultured on surfaces coated with the immobilized BDNF mimetic peptide. (a) Bright field images of cells cultured on surfaces coated with, APTES, the immobilized BDNF mimetic peptide, or control PDL. (b) Confocal micrographs of neuronal cells stained with calcein (live marker) and propidium iodide (Dead marker) cultured on the coatings referred in (a). (c) Quantification of cell survival under conditions shown in (b). (values normalized to total cells).
Figure 14:
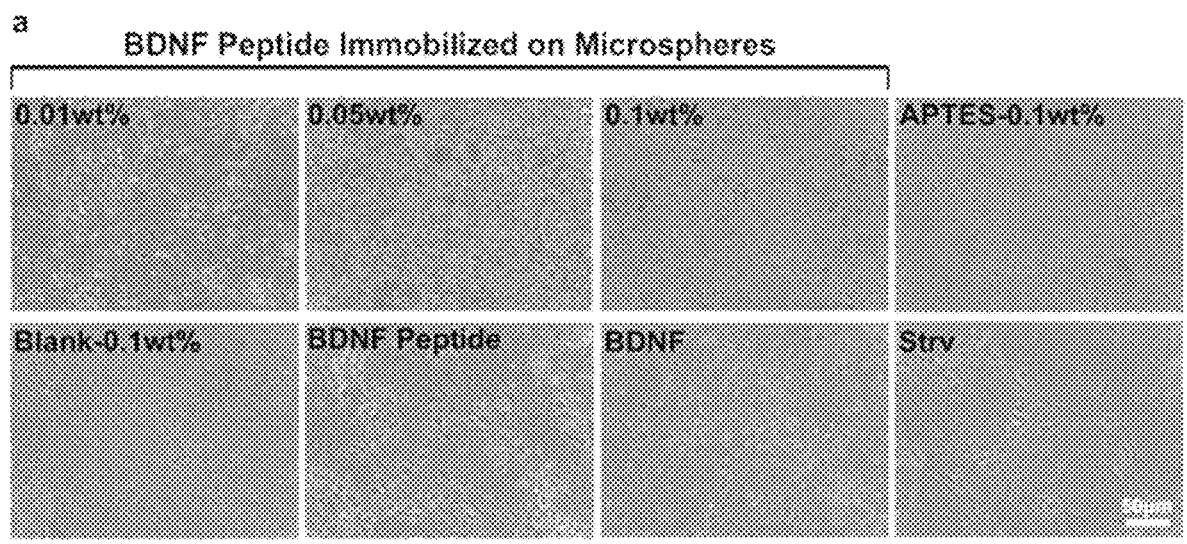
FIG. 14. BDNF peptide immobilized on silica microsphere surfaces to probe TrkB receptor activation. (a) Bright field images of primary cortical neurons (14 DIV) treated with increasing concentrations of silica microparticles functionalized with BDNF peptide, APTES coated microparticles, Blank particles, BDNF peptide, BDNF native protein and starvation conditions for 6 h. (b) Western blot of p-TrkB and total TrkB receptor in neural cells treated using the conditions described in (a). (c) Densitometry analysis of p-TrkB of the conditions shown in (a). (Intensity values normalized to TrkB). *P<0.05, P<0.01 and *P<0.001, LSD test (n=3).
Figure 14:
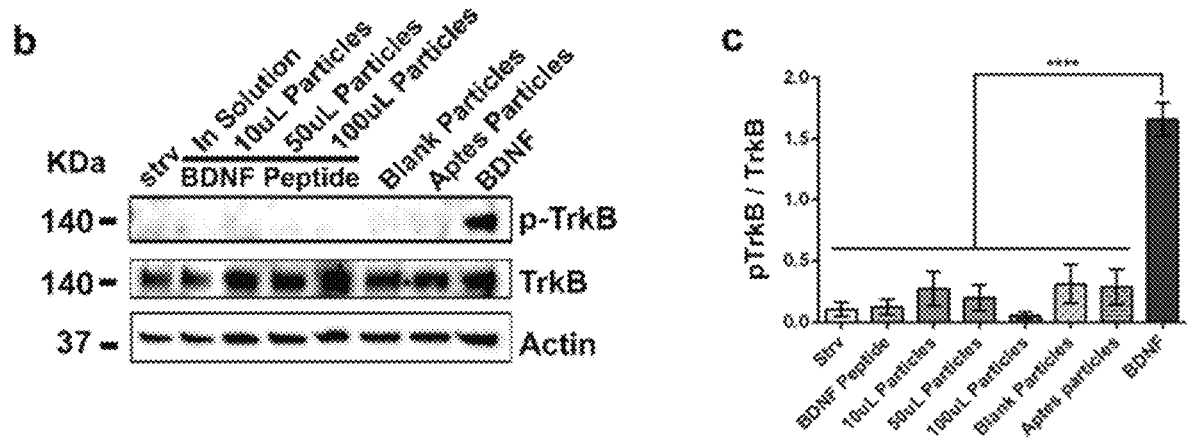

To understand the importance of the PA fiber signal presentation, neuronal cells were treated with different co-assembly ratios with E2 Filler PA (10, 20, 50, and 90 mol %) for 6 h. For 10-50 mol % BDNF PA, we observed an increase in activation of TrkB receptor in comparison with the control conditions (FIG. 12). Conversely, higher ratios of the BDNF mimetic PA (90-100 mol %), which do not form fibers, were unable to activate the receptor to the same degree. In order to validate that the BDNF peptide presentation on the nanofiber plays a role in TrkB phosphorylation, BDNF peptide was immobilized on alternative surfaces. Initially, aminopropyl triethoxysilane (APTES)-treated glass coverslips were functionalized with BDNF peptide using 1-ethyl-3-(dimethyl-aminopropyl)carbodiimide (EDC) chemistry (Ref 39; herein incorporated by reference in its entirety). Neuronal cells cultured on BDNF and poly-D-lysine (PDL) treated glass coverslips showed dramatic differences in cell survival after 5 DIV. On BDNF coverslips, cell survival was reduced significantly (29%) compared to the PDL control condition (98%). Neural cells on APTES-treated surfaces did not survive. The BDNF peptide was covalently attached to 6 µm silica microspheres to treat neuronal cultures in solution using the same method as with the BDNF mimetic PA. Neuronal cells treated with BDNF peptide silica particles did not show any activation of TrkB in primary neuronal cultures after 6 h in vitro (FIGS. 13 & 14). Taken together, the co-assembly and microsphere results indicate that the display of BDNF signal on a PA nanofiber is essential to engage and activate the TrkB receptor.

BDNF PA-TrKB Signaling Activates MAPK, PI3K and PLCγ

BDNF-TrkB signaling is involved in transcription, translation, and trafficking of proteins during various phases of synaptic development and has been implicated in several forms of synaptic plasticity (Refs. 9, 40-43; herein incorporated by reference in their entireties). These functions are carried out by a combination of the three signaling cascades triggered when BDNF binds to TrkB: the mitogen-activated protein kinase (MAPK), the phospholipase-C gamma (PLCγ), and the phosphatidylinositol 3-kinase (PI3K) pathways. Activation of the MAPK and PI3K pathways was detected by western blot analysis using antibodies against phosphorylated Erk (pErk 1/2) and phosphorylated AKT (pAKT), respectively. The BDNF PA and native BDNF protein showed a marked increase in activation of the MAPK and PI3K pathways in comparison with the control conditions after 6 h of treatment (FIG. 2F). These pathways play crucial roles in dendritic formation, survival, and axonal growth.44-46 The PLCγ-pathway, which is one of the pathways associated with synaptic plasticity (Refs. 47-49), was highly activated in all conditions, indicating that this activation is also associated to other stimuli in the culture environment. The western blot analysis confirms the ability of the BDNF PA to induce the activation of MAPK and PI3K downstream pathways associated with the TrkB receptor which are important for survival, growth, and synaptic plasticity (Refs. 50-51; herein incorporated by reference in their entireties).

Neural Plasticity and Maturation Mediated by the BDNF PA

Figure 3:
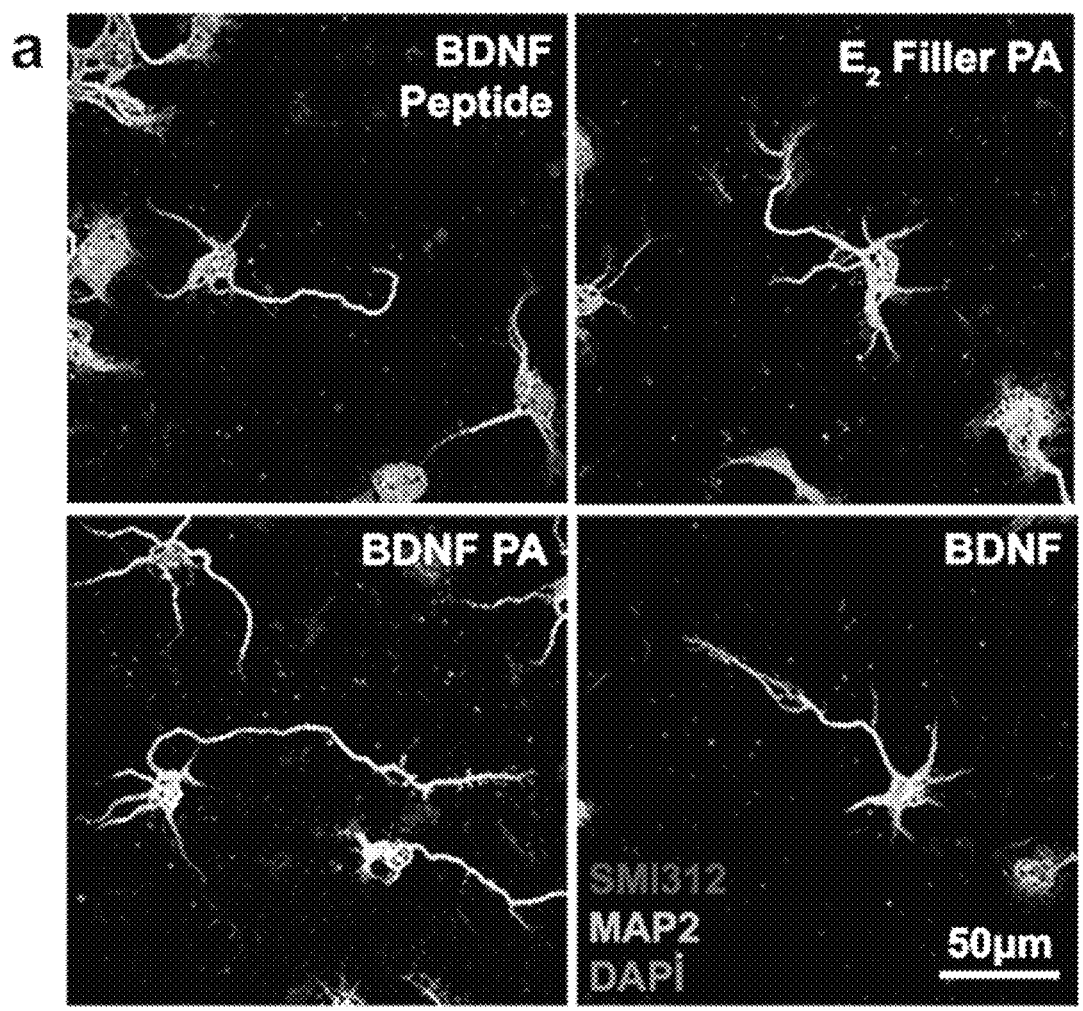
FIG. 3. Morphometric analysis and cell maturation. (a) Confocal images of neuronal cells treated with BDNF Peptide, $E_2$ Filler PA, BDNF PA and BDNF protein for 24 h in vitro. Cells were stained with SMI312 (axonal marker), MAP2 (dendritic marker) and DAPI (nuclei). (b) Morphometric analysis for neural cells treated with starvation media (Strv), BDNF peptide, $E_2$ Filler PA, BDNF PA and BDNF protein for 24 h. (c) Confocal microscopy images of neuronal cells treated with starvation media (Strv), BDNF peptide, BDNF PA and BDNF protein during 2 weeks in vitro. Cells were stained for MAP2 (dendritic marker), Tuj-1 (neuronal marker) and DAPI (nuclei). (d) Western blot of PSD95 (post-synaptic marker), MAP2 (maturation marker) and Tuj-1 (neuronal marker) of neuronal cells treated with Strv, BDNF peptide, BDNF PA and BDNF protein during 2 weeks in vitro. (e) Densitometry analysis of MAP2 maturation marker and PSD95 postsynaptic marker of the conditions shown in (d). Intensity values normalized to actin. *$P<0.05$, $P<0.01$ and $P<0.001$, and ****$P<0.0001$, LSD test (b) (n=60), (e) (n=3).
Figure 3:
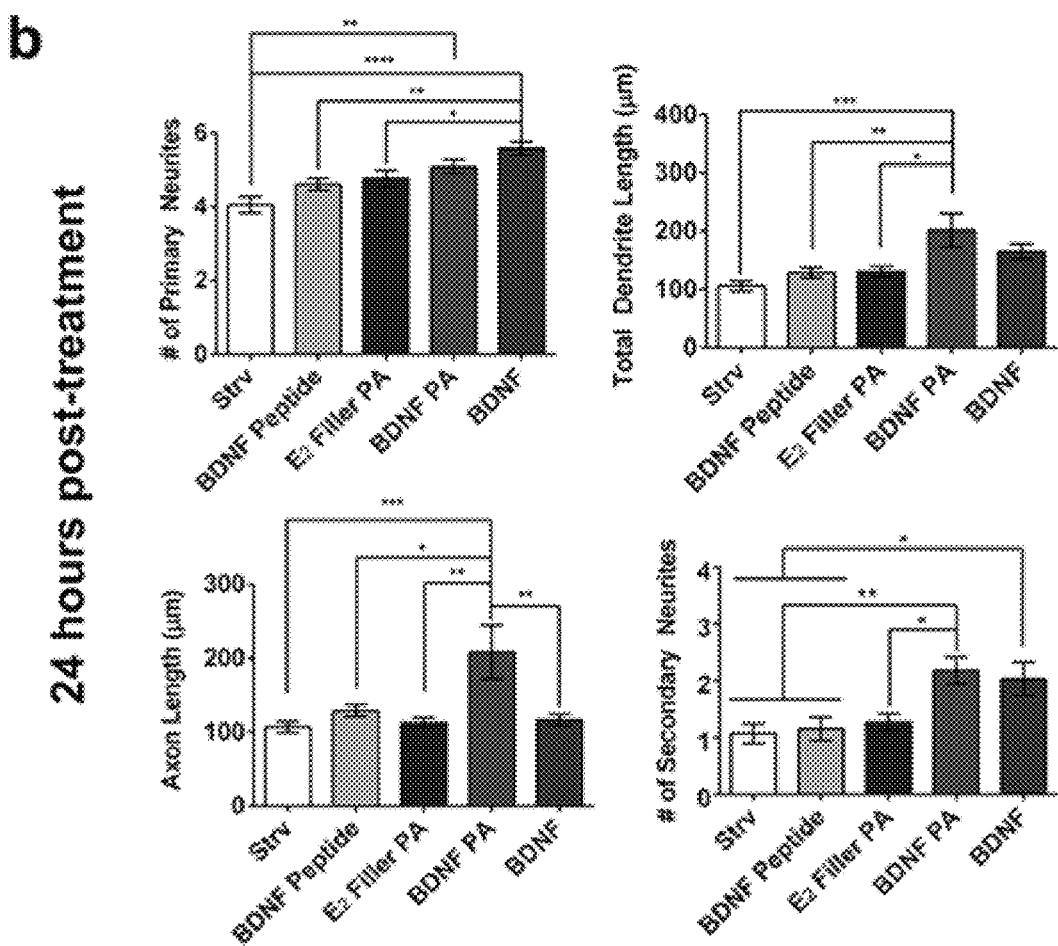
Figure 3:
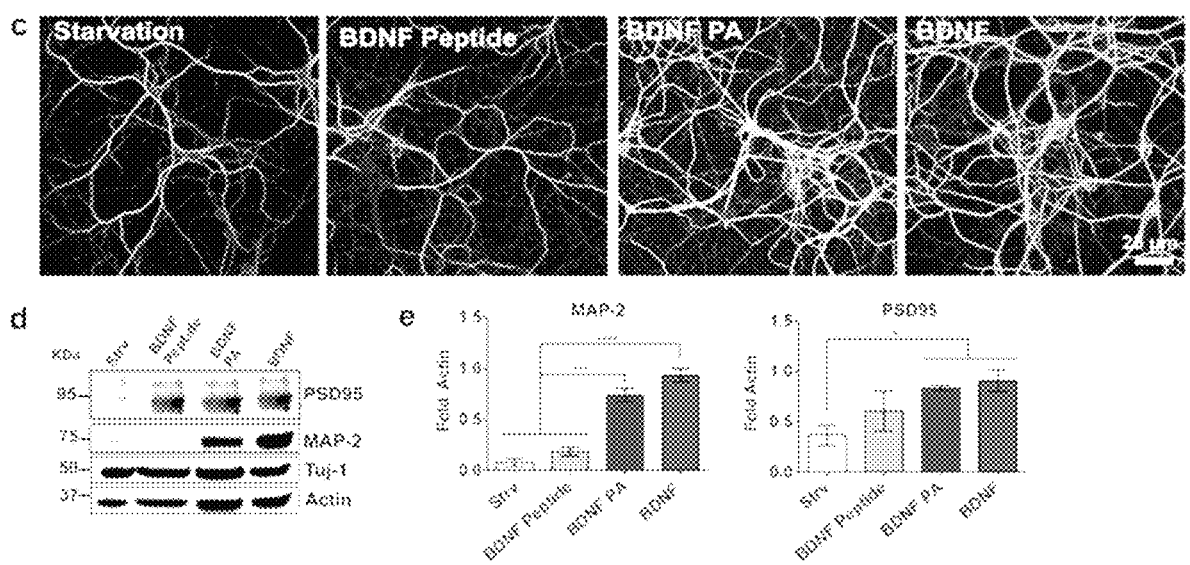
Figure 15A:
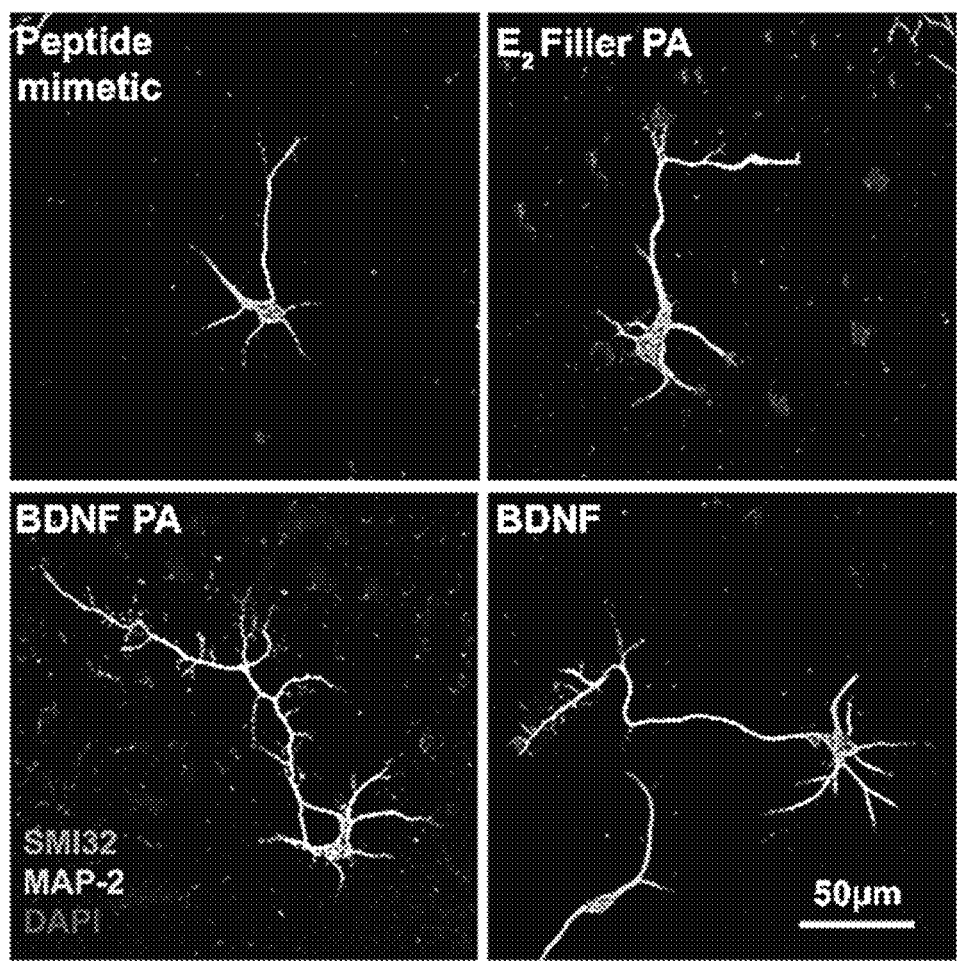
FIG. 15. Morphometric analysis of primary cortical neurons after 72 h treatment with BDNF PA. (a) Confocal images of neuronal cells treated BDNF Peptide, $E_2$ Filler PA, BDNF PA and BDNF for 72 h in vitro. Cells were stained with SMI312 (axonal marker), MAP2 (dendritic marker) and DAPI (nuclei). (b) Morphometric analysis of number of primary neurites, total dendrite length, average axon length, and number of secondary neurites for neuronal cells treated with starvation media (strv), BDNF peptide, $E_2$ Filler PA, BDNF PA and BDNF for 72 h. *P<0.05, P<0.01, *P<0.001, and ****P<0.0001, LSD test (b) (n=60).
Figure 15B:
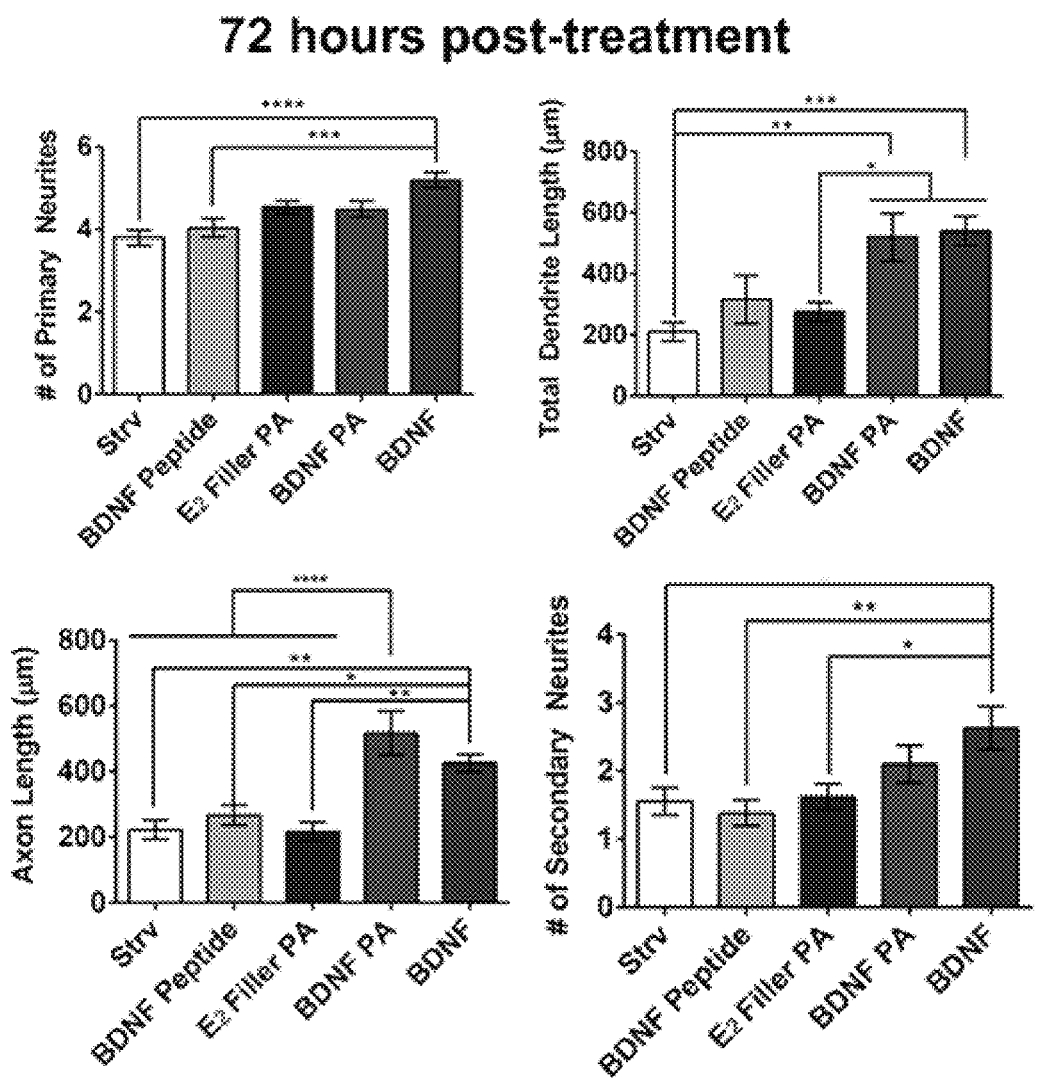

Experiments were conducted during development of embodiments herein to examine whether activation of the receptor, and consequently downstream pathways, is associated with changes in neuronal morphology. To investigate this, primary mouse cortical neurons (3 DIV) were cultured in the presence of the various treatment conditions (starvation media, BDNF peptide, E2 Filler PA, the BDNF PA or the BDNF protein) for 24 and 72 h. The neuritic complexity was analyzed by immunocytochemistry with microtubule associated protein 2 (MAP2) and SMI312, which are dendritic and axonal markers, respectively. BDNF facilitates neurite branching (Ref 52; herein incorporated by reference in its entirety), so experiments were conducted to determine if the BDNF PA induces a similar effect. At 24 h, cells treated with the BDNF PA showed a significant increase in the total dendrite and axon length in comparison with the native BDNF protein and control conditions. In addition, the BDNF PA exhibited a positive tendency in the number of primary neurites, and a significant increase in the number of secondary neurites compared to the control conditions. However, there were no statistical differences in neurite number between cells treated with the BDNF PA and native BDNF protein (FIG. 3*a-b*). After 72 h in vitro, neurons treated with BDNF PA or BDNF protein had similar axonal and dendritic length compared to the control conditions (FIG. 15).

To assess the effect of BDNF PA on neuronal maturation, the expression of mature neuronal markers was examined at long time points. Neuronal cells (14 DIV) cultured during 16 DIV in the presence of the BDNF PA and native BDNF protein showed a significant increase of MAP2, a marker associated to neuronal maturation Ref 53; herein incorporated by reference in its entirety), observed by immunocytochemistry and western blot. Moreover, post-synaptic density 95 (PSD95), which plays an important role in post-synaptic plasticity (Ref 54; herein incorporated by reference in its entirety), showed an increase in all the BDNF conditions including the BDNF peptide. Therefore, BDNF PA-TrKB signaling enhances the maturation and the delivery of key molecules at post-synaptic areas of the cells.

Functional Analysis Through Electrophysiology

Figure 4:
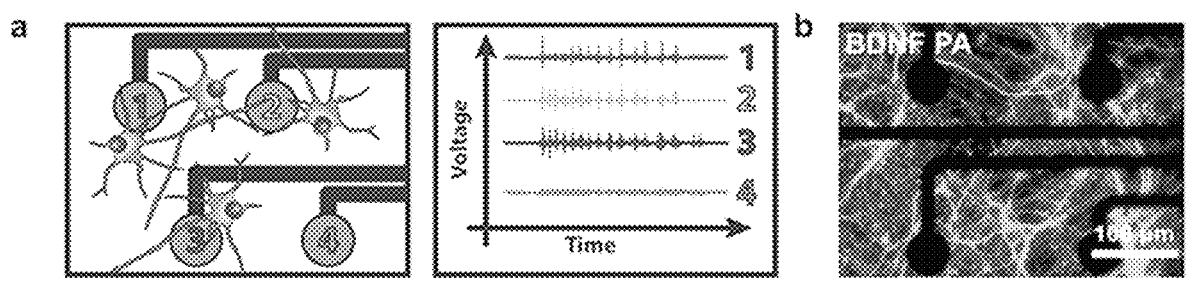
FIG. 4. Electrophysiological studies of neuronal cultures treated with BDNF PA. (a) Schematic of neurons plated on microelectrode array (MEA) plate (left) showing increased voltage from electrodes in contact with mature neurons (right). (b) Neurons cultured on MEA plate treated with BDNF PA for 30 DIV. Cells stained with MAP2 (maturation marker) and DAPI (nuclei). (c) Raster plots showing electrical activity of culture at 14 and 30 DIV for wells treated with BDNF PA and BDNF protein. (d-f) Electrophysiology data showing (d) mean firing rate, (e) network burst duration, and (0 number of spikes per network burst for cells treated with Strv, BDNF peptide, BDNF PA and BDNF protein during 2 weeks in vitro. *$P<0.05$, $P<0.01$ and *$P<0.001$, and ****$P<0.0001$ respect to starvation media and #$P <0.05$ respect to BDNF peptide, LSD test (n=8 for BDNF PA and BDNF protein, and n=4 for Strv and BDNF peptide).
Figure 4:
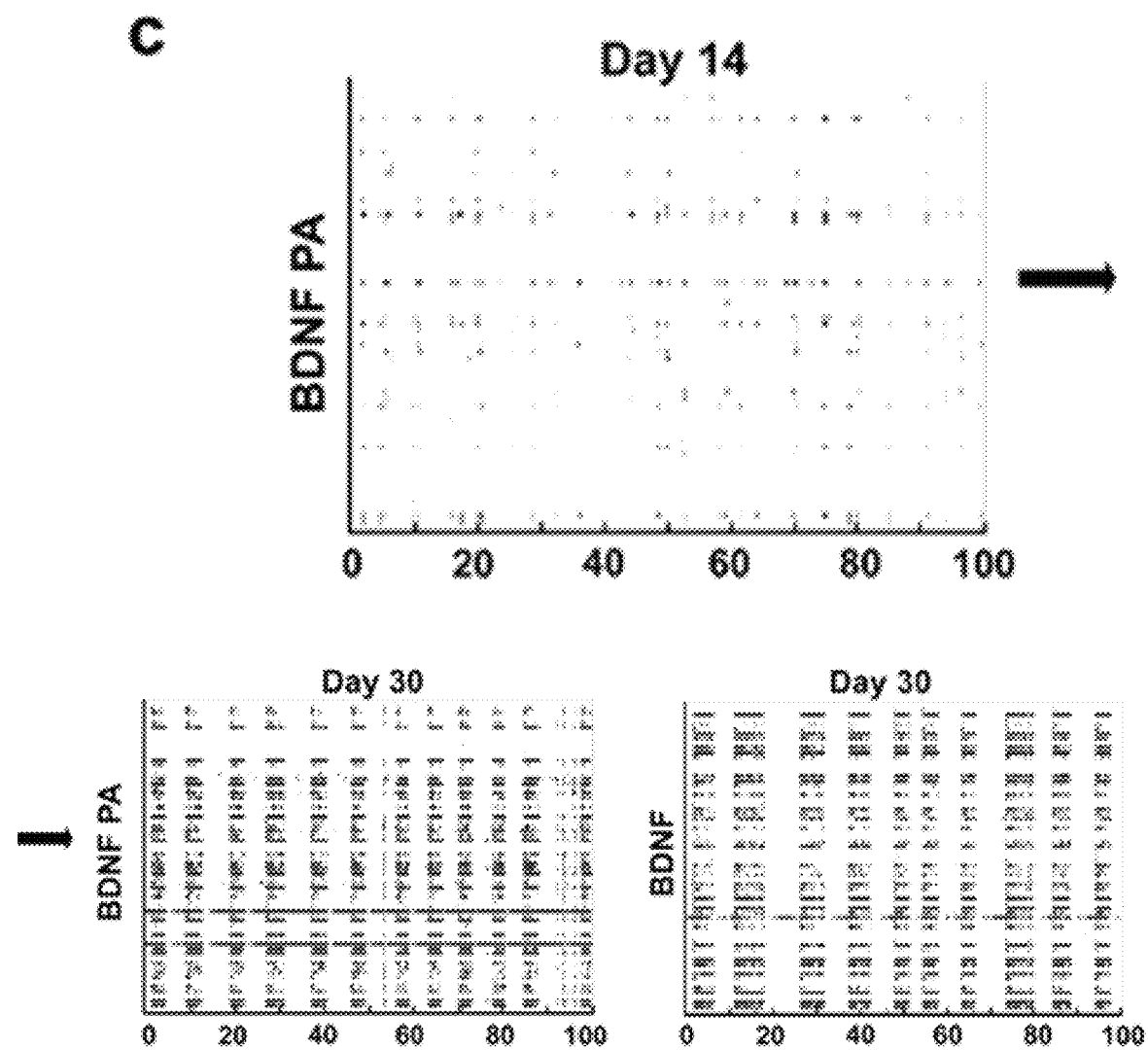
Figure 4:
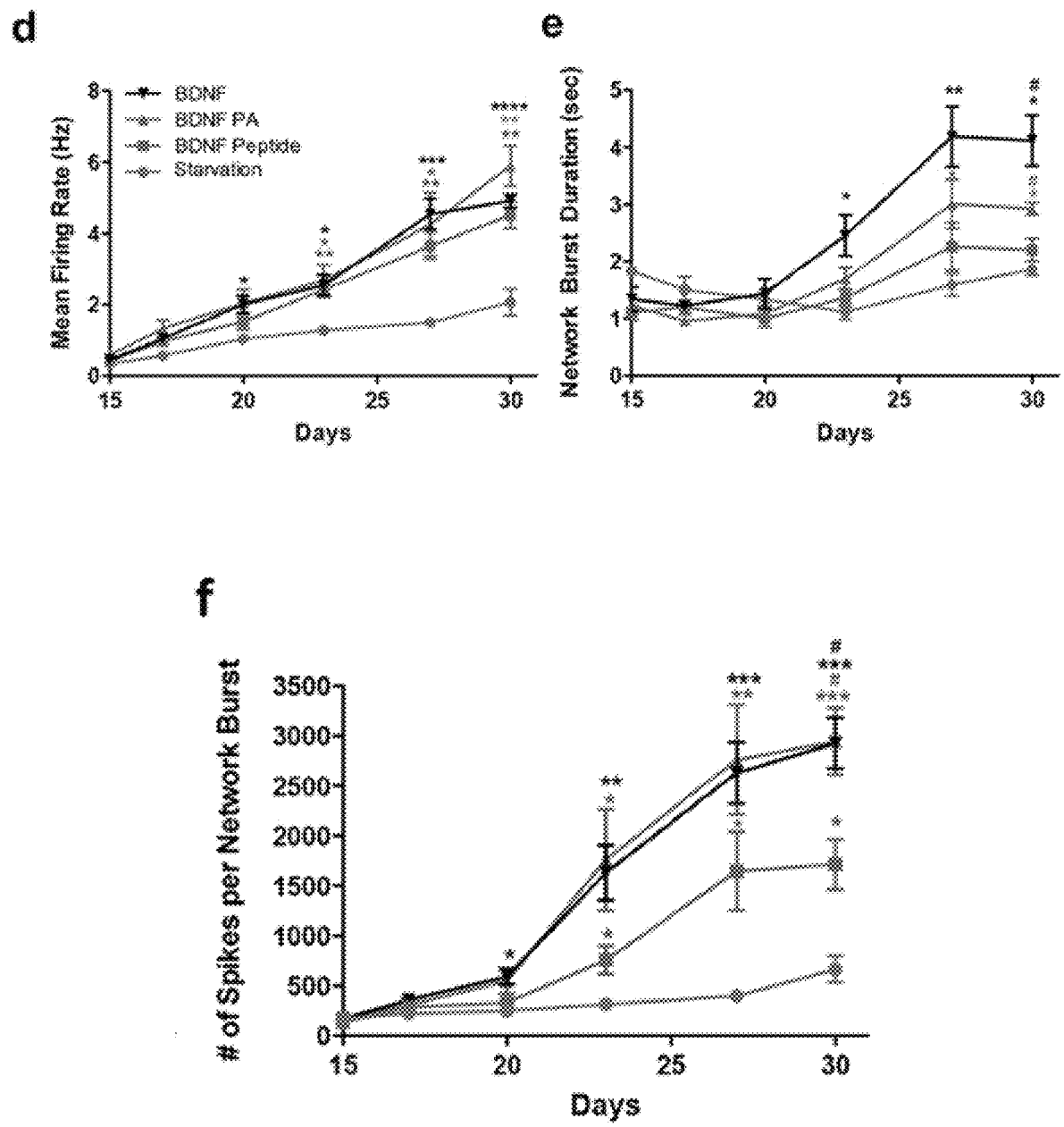
Figure 16:
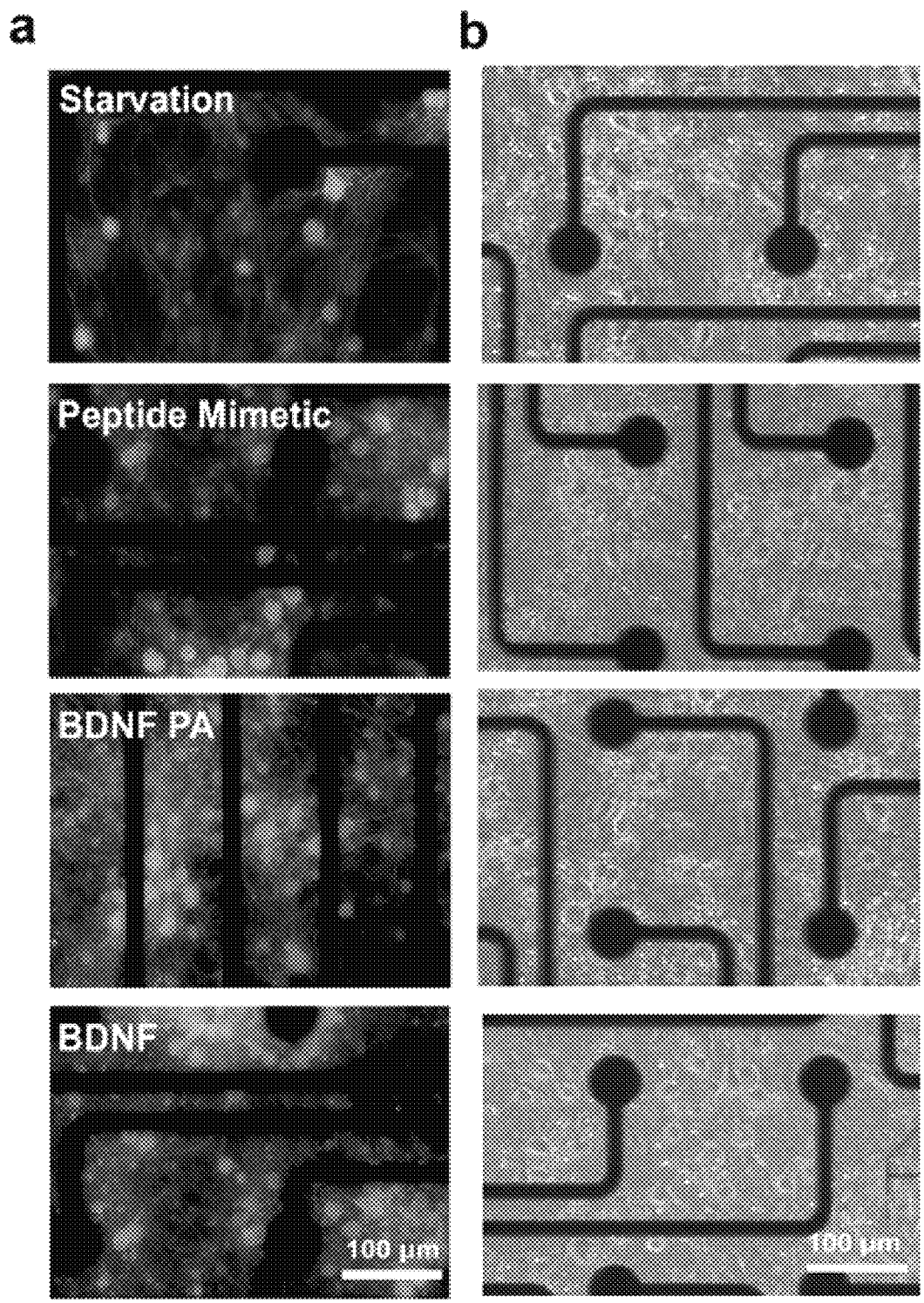
FIG. 16. Electrophysiology studies of neuronal cultures treated with different conditions. (a) Fluorescent micrographs of neurons cultured on an MEA plate treated with starvation media, BDNF Peptide, BDNF PA, or BDNF protein for 30 DIV. Cells stained with MAP2 (maturation marker) and DAPI (nuclei). (b) Bright field images of conditions referred-to in (a). (c and d) Raster plots showing electrical activity of culture at 14 and 30 DIV (d) for wells treated with conditions in (a).
Figure 16:
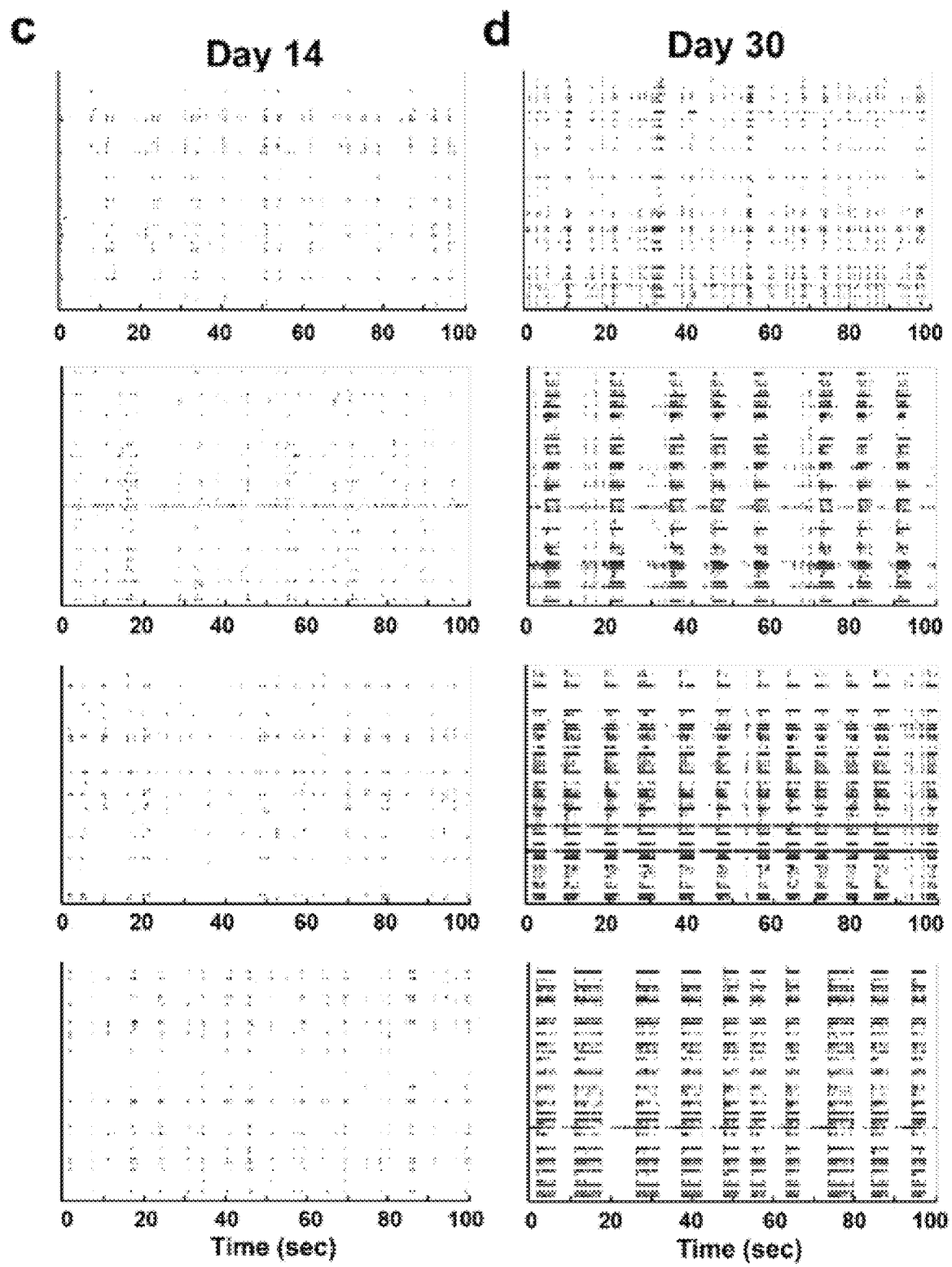
Figure 17A:
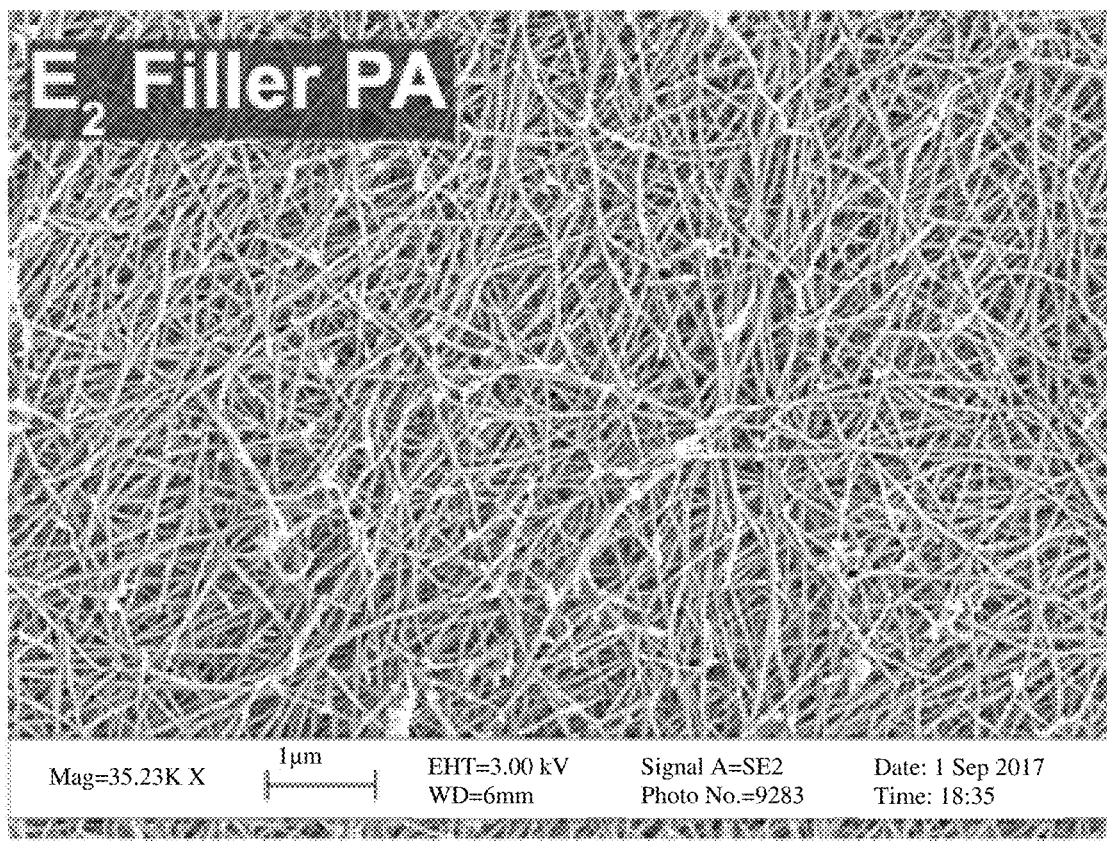
FIG. 17. SEM micrographs of PA gels. SEM images of $E_2$ Filler PA 100 mol %, $E_4$PEG PA, Linear BDNF PA, and the BDNF PA co-assembled with the $E_2$ Filler PA at 10 mol %.
Figure 17B:
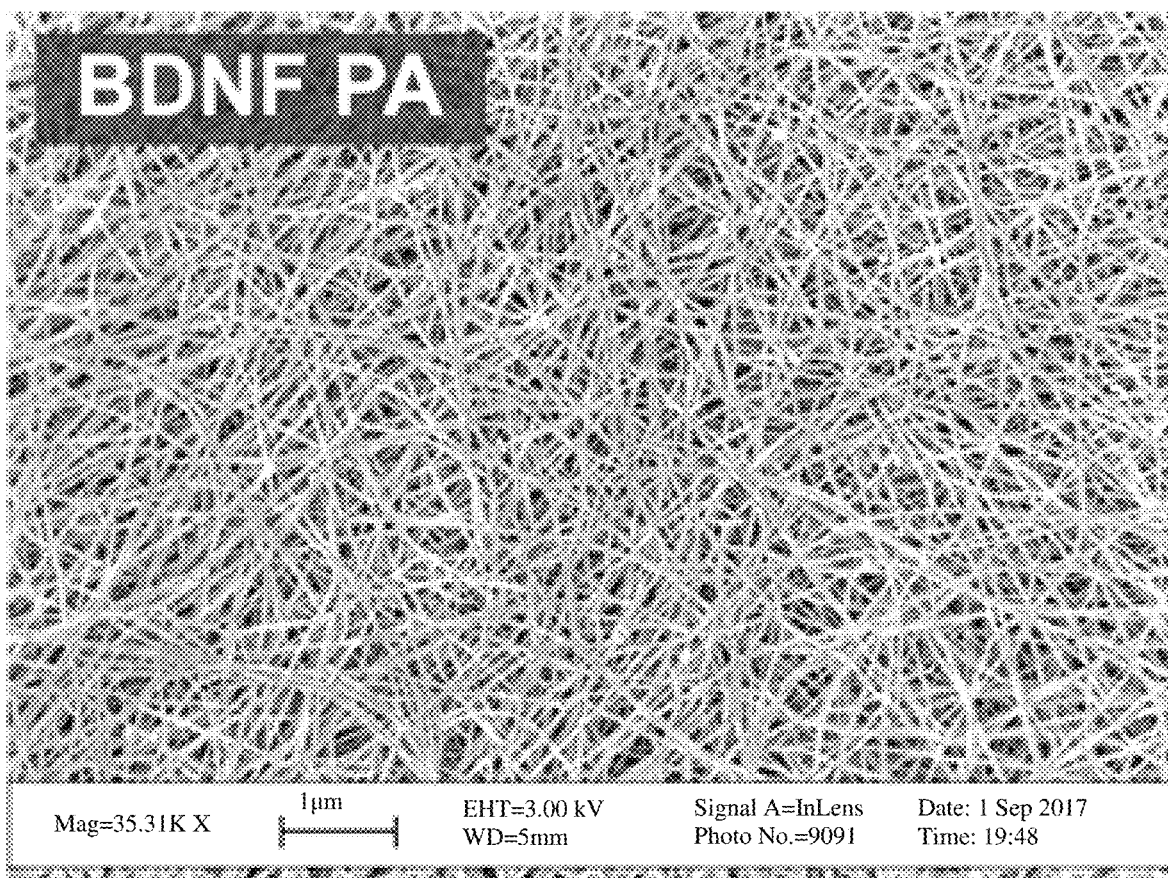
Figure 17C:
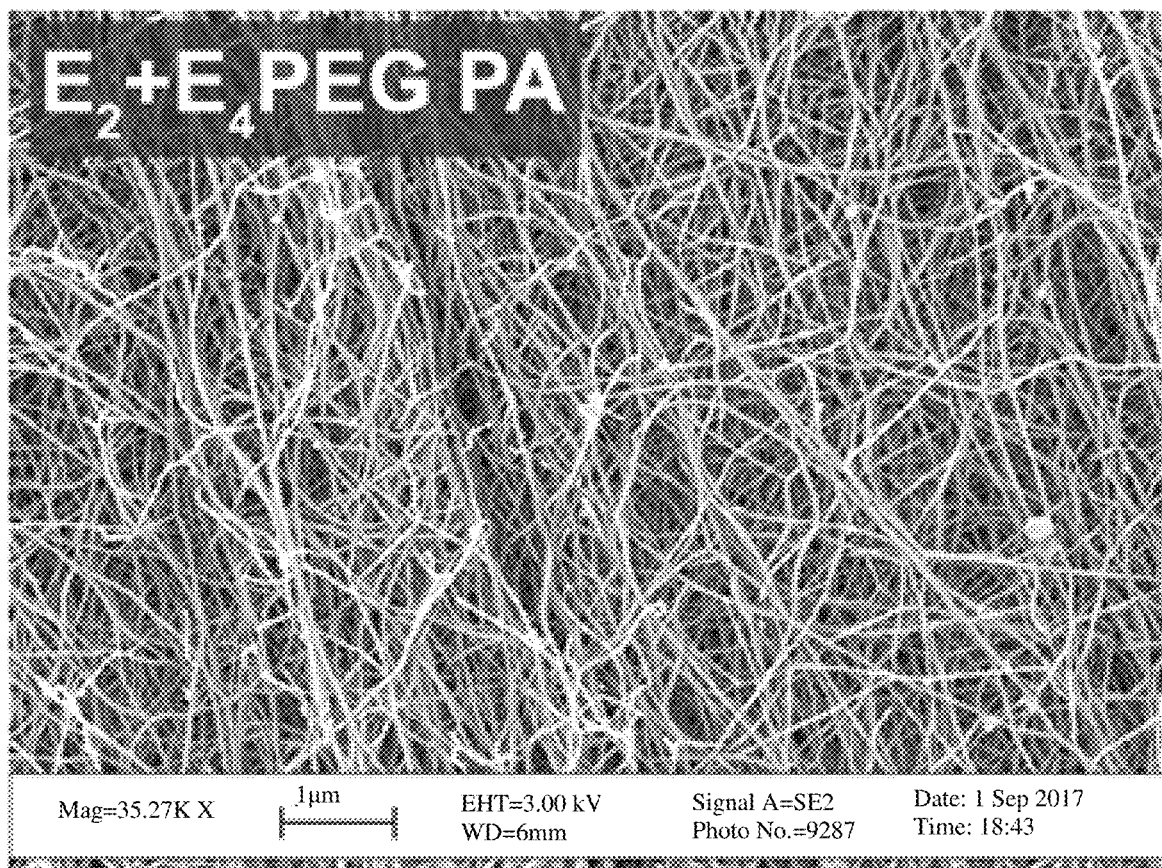
Figure 17D:
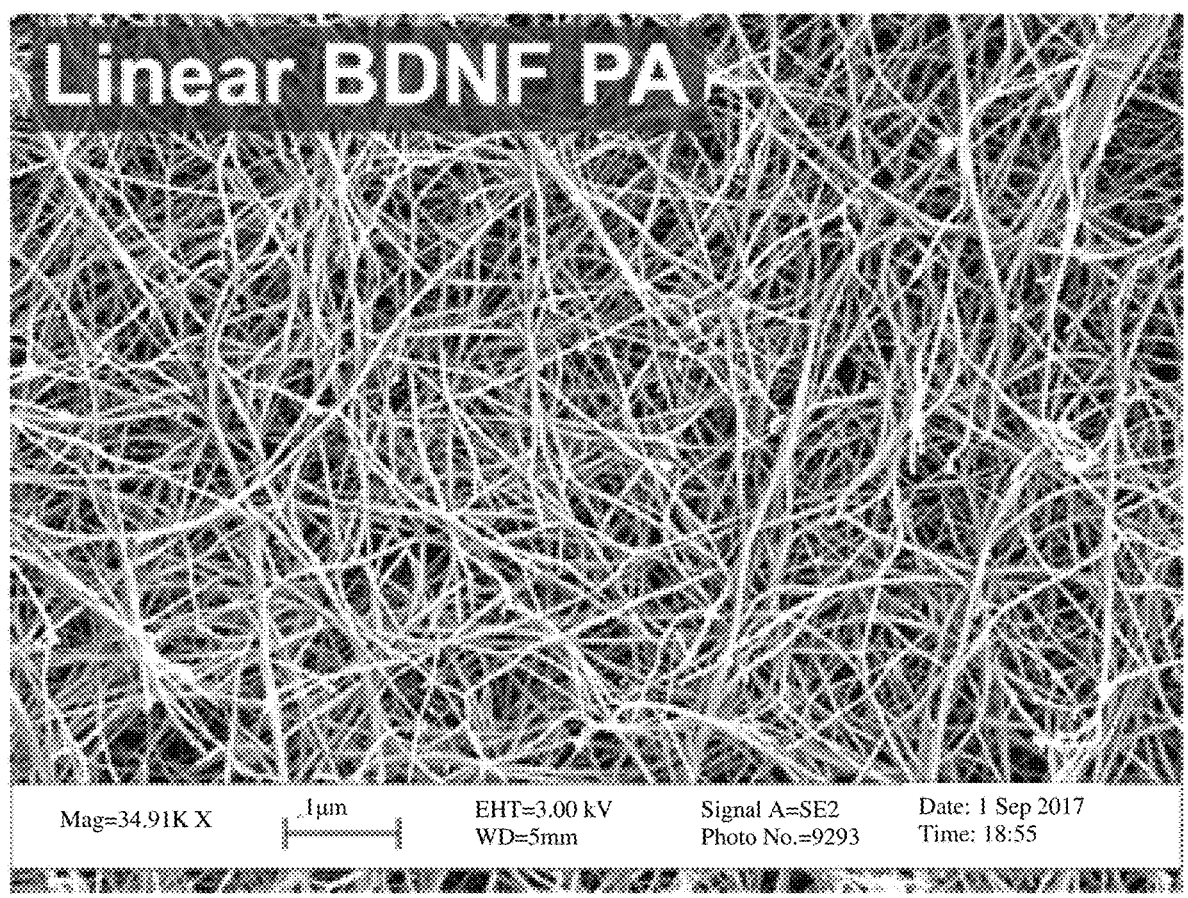
Figure 18:
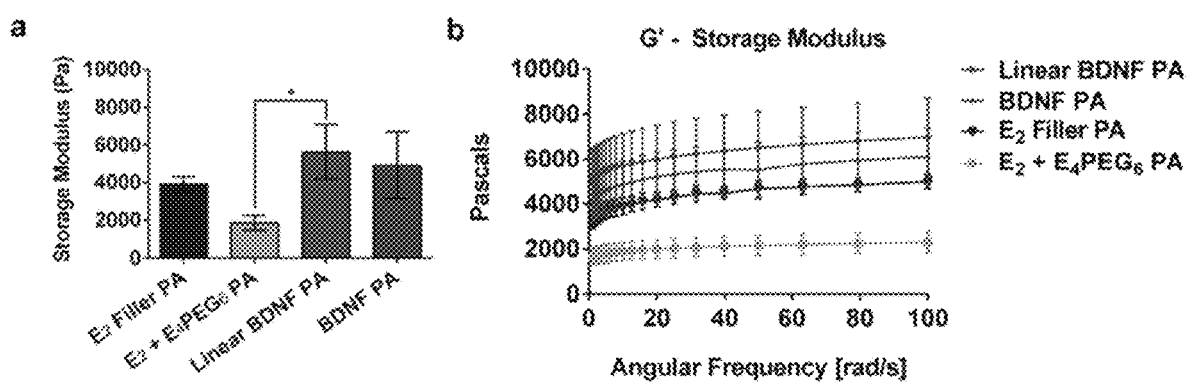
FIG. 18. Rheological studies of PA gels. (a) Storage modulus of $E_2$ Filler PA 100 mol %, $E_4$PEG PA, Linear BDNF PA, and the BDNF PA co-assembled with the $E_2$ Filler PA at 10 mol %. (b) Frequency sweep showing the storage modulus, G', for angular frequencies ranging from 0-100 rad/s, of the conditions referred in (a). (c) Strain sweep showing the storage modulus, G', and loss modulus, G", at shear strain ranging from 0-100 of conditions referred in (a). *P<0.05, LSD test (n=3).
Figure 18:
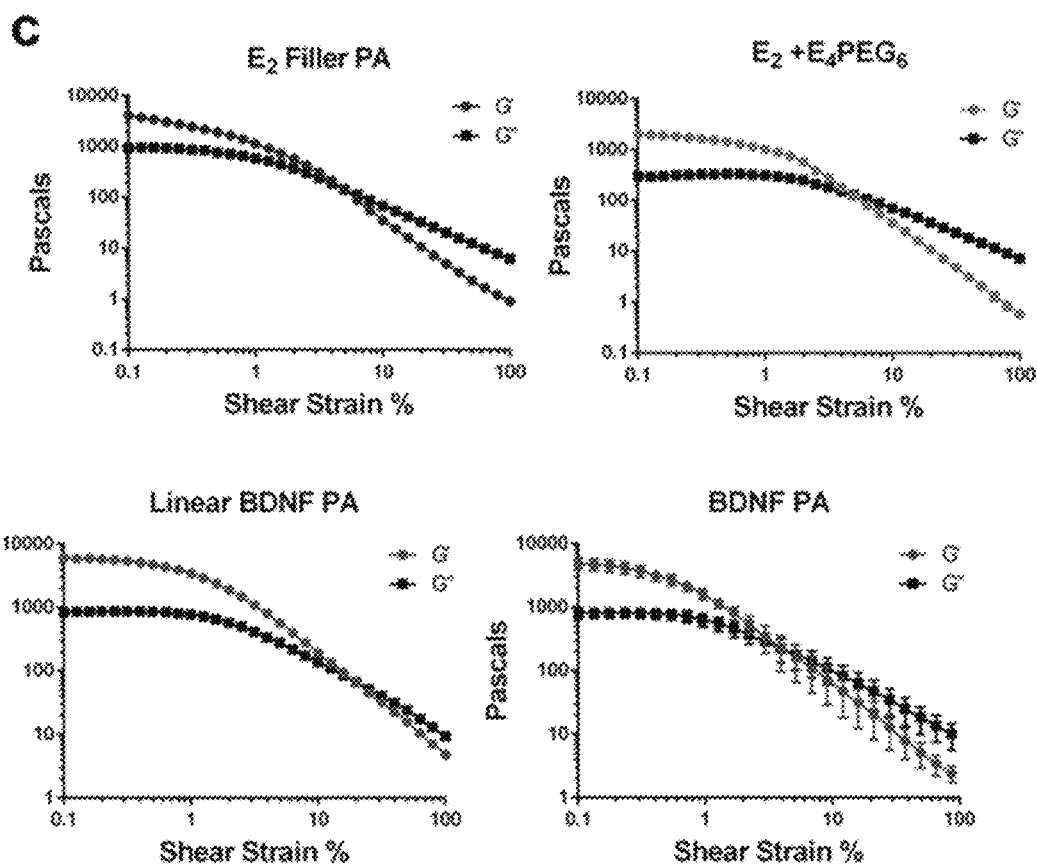

To determine if enhanced expression of neuronal maturation markers is correlated with electrophysiological maturation, experiments were conducted during development of embodiments herein to assess electrical activity of primary mouse cortical neurons. The multi-electrode array (MEA) platform was used to assess the spontaneous and synchronized activity of neuronal cultures over time, as illustrated in the spike raster plots on day 14 and day 30 from a BDNF PA treated well (FIGS. 4C & 16). Cells cultured with BDNF PA and BDNF conditions for 30 days in vitro showed increased spontaneous firing frequency relative to the control condition (FIGS. 4D & 16). Over time, cells treated with the BDNF PA or BDNF native protein were able to fire longer network bursts with significantly more spikes per network burst than those in the control media (FIGS. 4E-F & 16). These results demonstrate that the treatment of neuronal cells with the BDNF PA alters the developmental timeline of neuronal network excitability in primary neuronal cultures.

Increased Maturation, Infiltration and Electrical Activity of Neurons on Three-Dimensional BDNF PA Scaffolds Experiments were conducted during development of embodiments herein to investigate whether neurons could survive, infiltrate and functionally mature to conduct information by generating action potentials on three-dimensional (3D) PA scaffolds. Six gel conditions were tested, including the BDNF PA, E2 Filler PA, BDNF protein encapsulated within E2 Filler PA (BDNF+E2 Filler), BDNF peptide encapsulated within the E2 Filler PA (Peptide+E2 Filler), Linear BDNF PA, and E4PEG PA. All PAs had a similar nanofiber morphology and storage moduli relative to the E2 Filler PA as seen by rheological measurements and scanning electron microscopy respectively (FIGS. 5A-B & 17-18). Furthermore, all the PAs have storage moduli ranging from 1.86 to 5.62 kPa, which is similar to the mechanical properties of neural tissue (Ref 55; herein incorporated by reference in its entirety).

Figure 5:
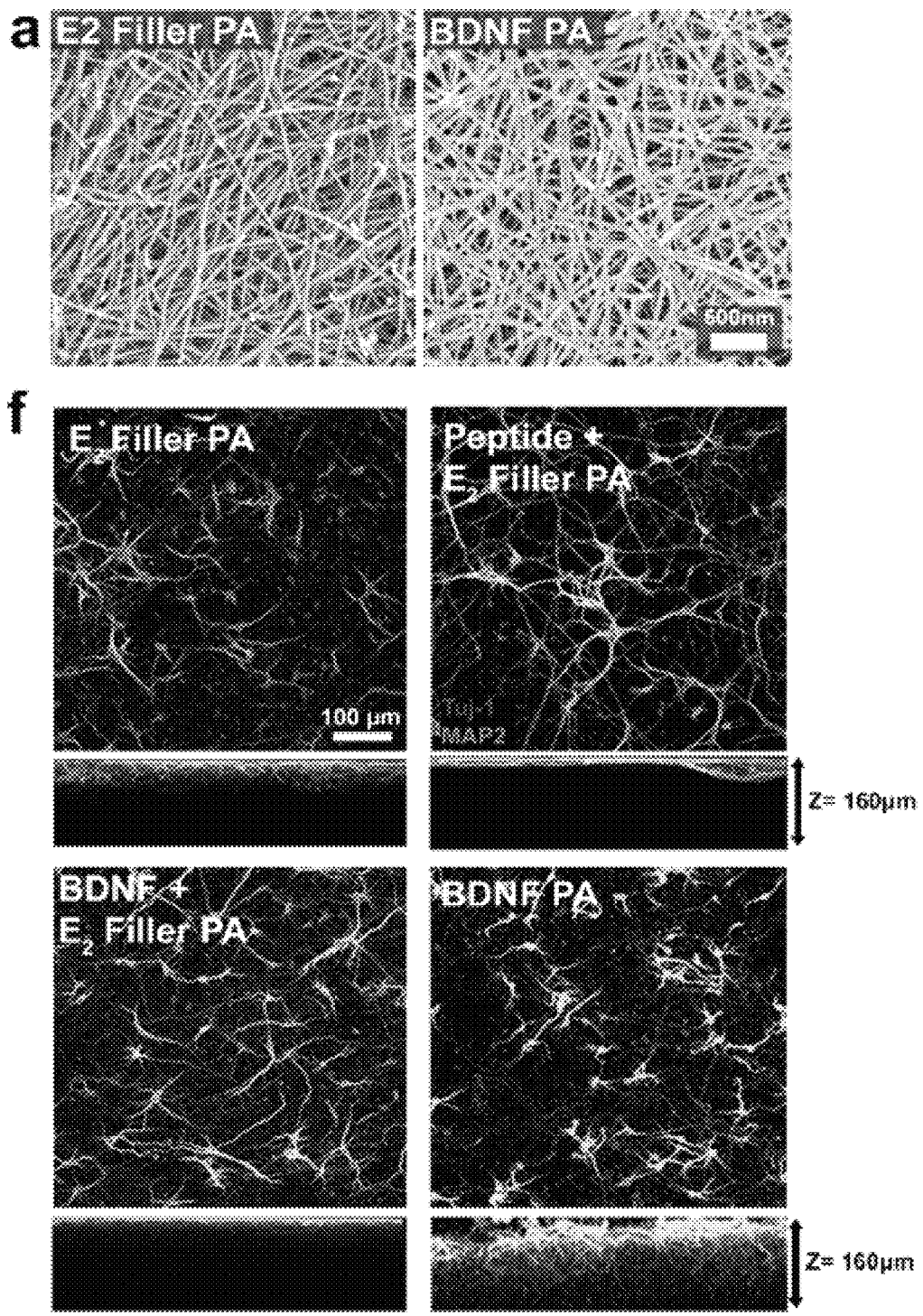
FIG. 5. Infiltration and maturation of cortical neurons in BDNF PA scaffolds. (a) SEM showing nanofibers in $E_2$ Filler PA and BDNF PA gels. (b) Storage moduli of $E_2$ filler PA and BDNF PA. (c-e) SEM (left) and confocal (right) images showing cortical neurons seeded on top of 3D PA scaffolds for 1 week in vitro. (f) Confocal images showing top and side (z-stack=160 μm) view sections of cells cultured on PA gel scaffolds for 1 week in vitro. Images show cells stained with MAP2 (dendritic marker), and Tuj-1 (neuronal marker). (g) Depth-coded z-stack reconstructions showing cell infiltration after 1 week in vitro. (h) Quantification of cell infiltration depth in $E_2$ Filler PA, BDNF+$E_2$ Filler PA, BDNF peptide+$E_2$ Filler PA, and BDNF PA gels. (i,j) Representative images of current-clamp recordings from neurons in BDNF+$E_2$ Filler PA, BDNF PA and $E_2$ Filler PA gels, 1 week in vitro. $P<0.01$ and **$P<0.0001$. LSD test (b and h) and ANOVA followed by posthoc analysis was used for current clamp recordings (j).
Figure 5:
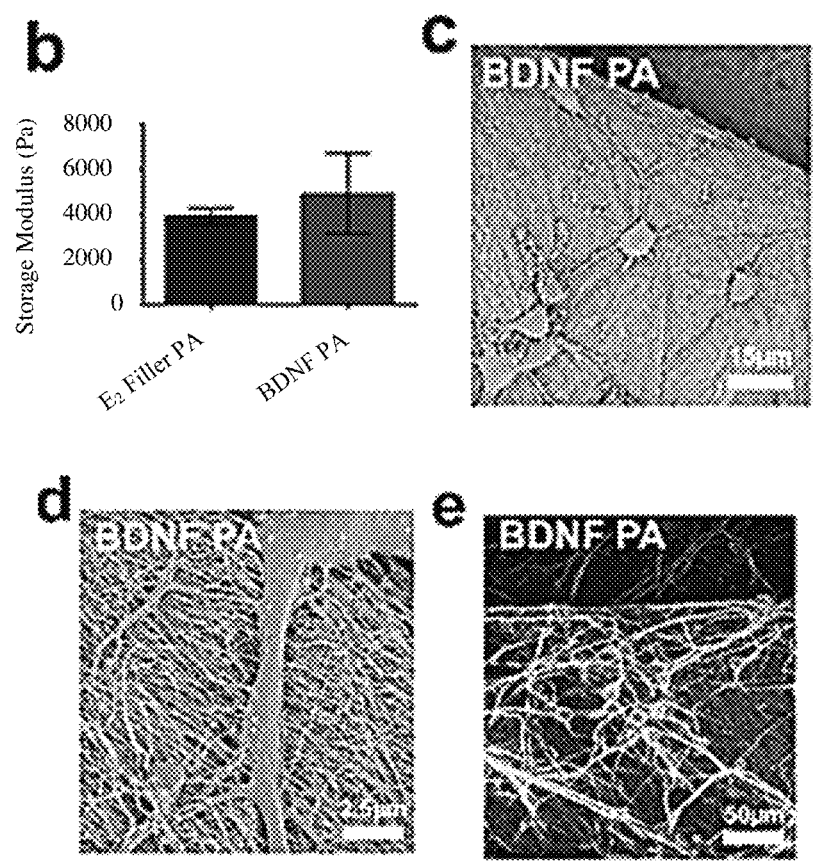
Figure 5G:
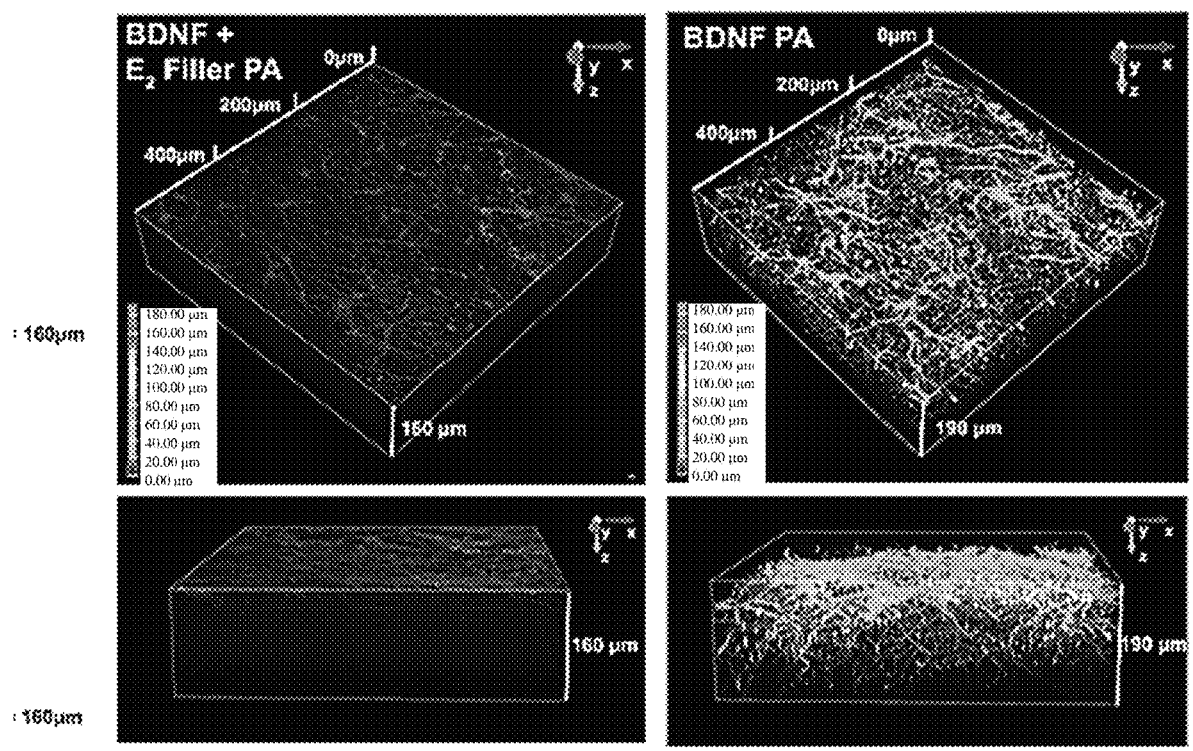
Figure 5:
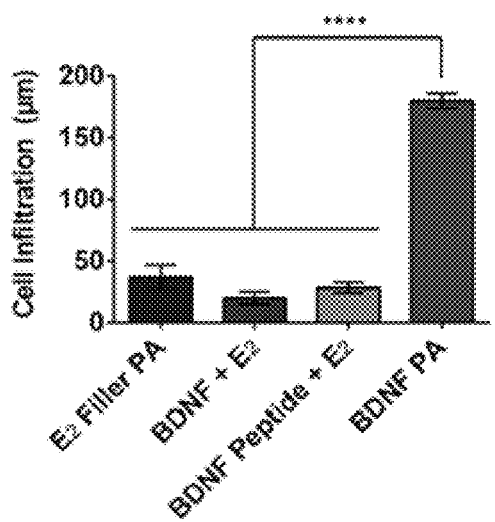
Figure 5:
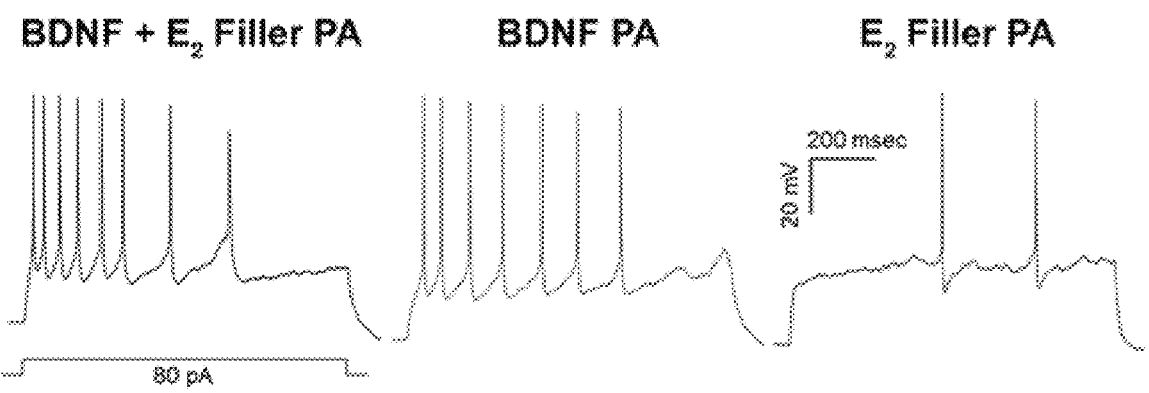
Figure 5:
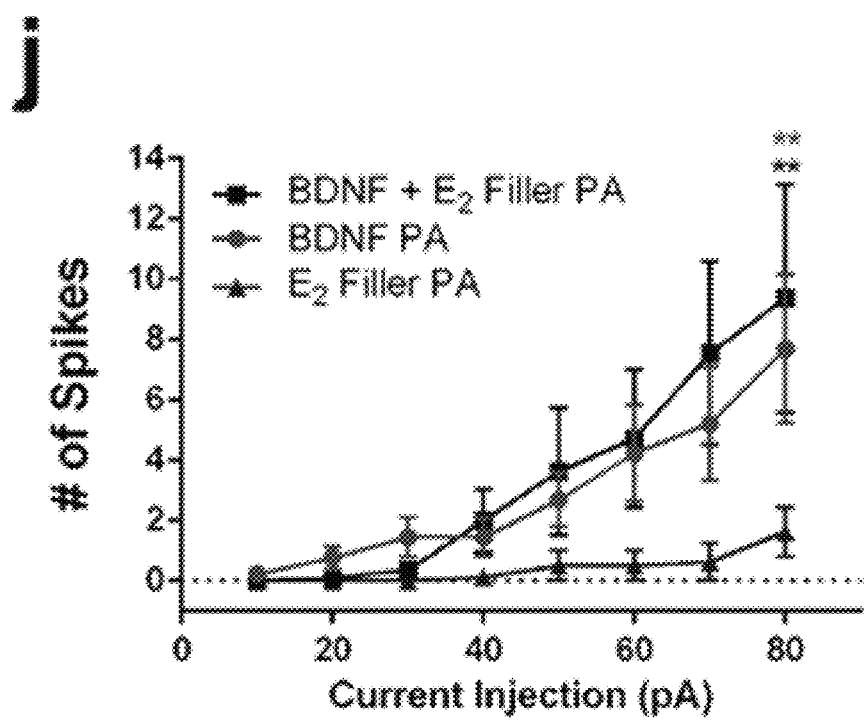
Figure 19:
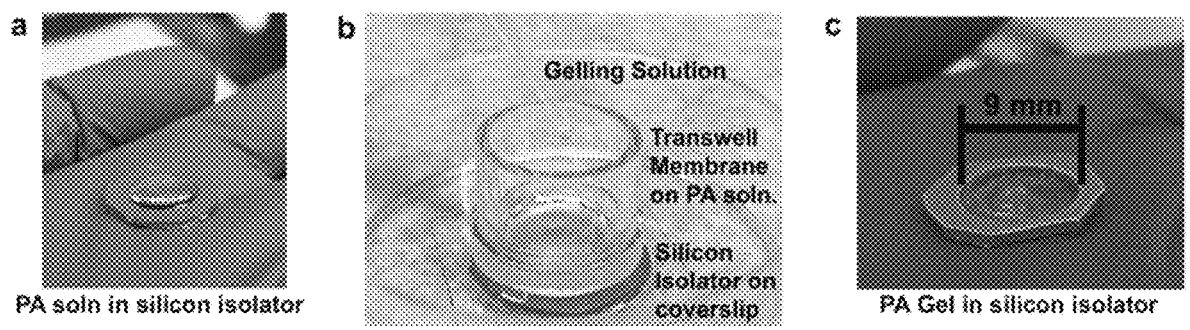
FIG. 19. PA Gel formation process. (a) PA gel solution is placed on glass coverslip within silicon isolator. (b) Transwell membrane is placed on top of PA solution and gelling solution is added through membrane. (c) PA gel molded to silicon isolator.
Figure 20A:
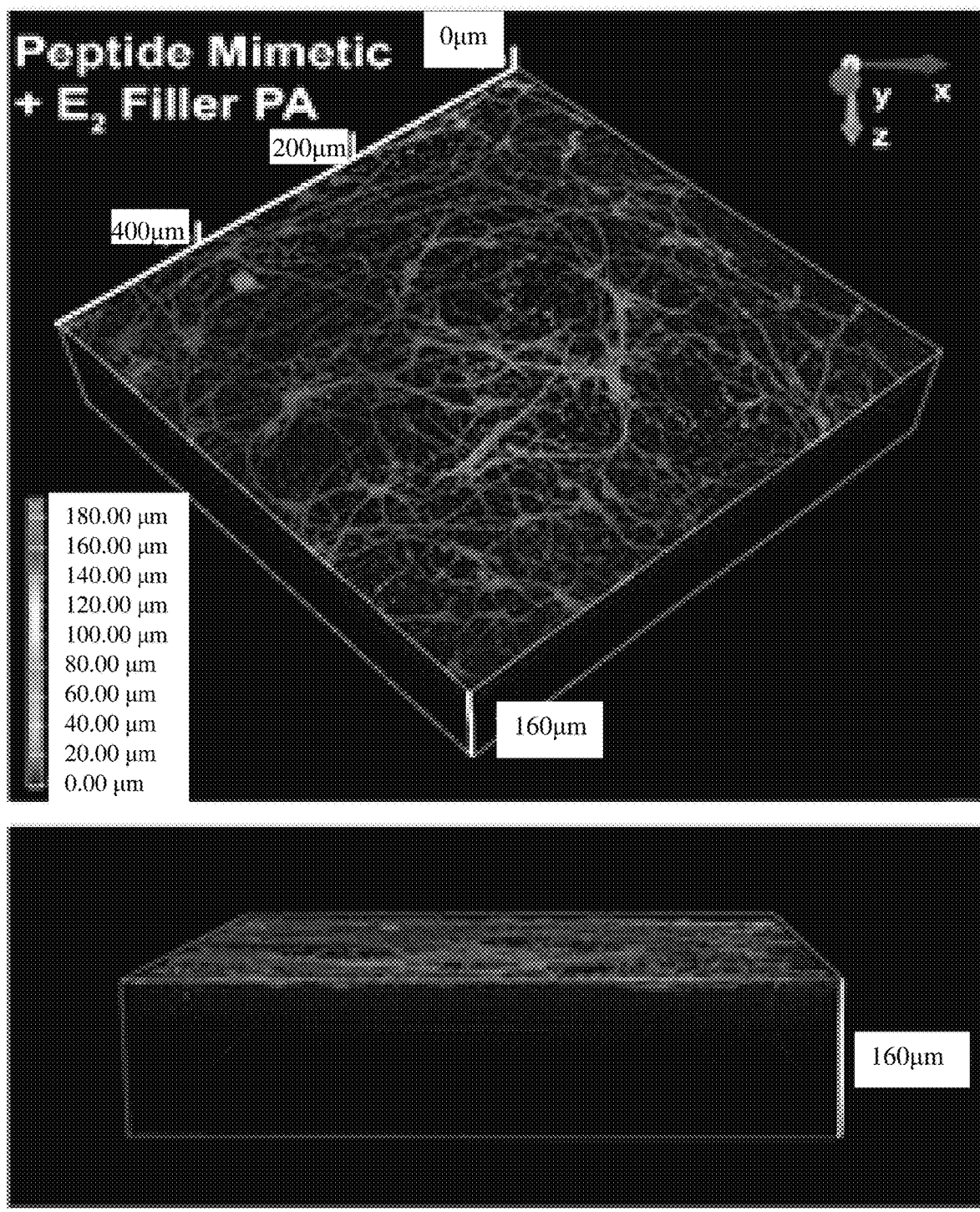
FIG. 20. Cell infiltration of primary cortical neurons on PA gels. (a-d) Depth-coded z-stack reconstructions showing cell infiltration on $E_2$ Filler PA, $E_2$ Filler PA gel+BDNF peptide, $E_4$PEG co-assembled at 10 mol % with $E_2$ Filler PA, and Linear BDNF PA after 1 week in vitro. (e-f) Pixel depth analysis of Tuj-1 (e) and MAP2 (0 in the conditions referred in (a). (g) Normalized average intensity of MAP-2 in $E_2$ Filler PAs, BDNF+$E_2$ Filler PA and BDNF PA.
Figure 20B:
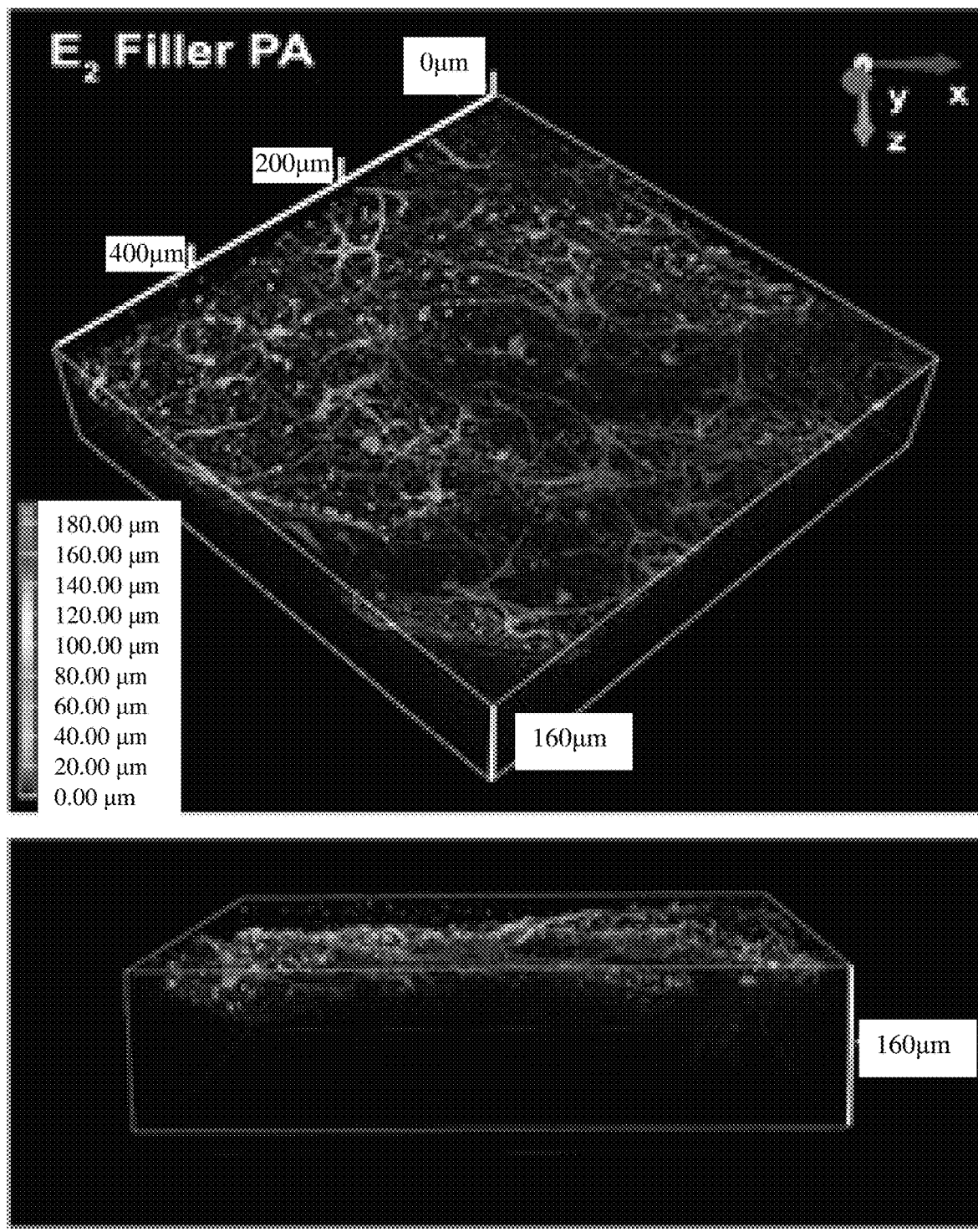
Figure 20C:
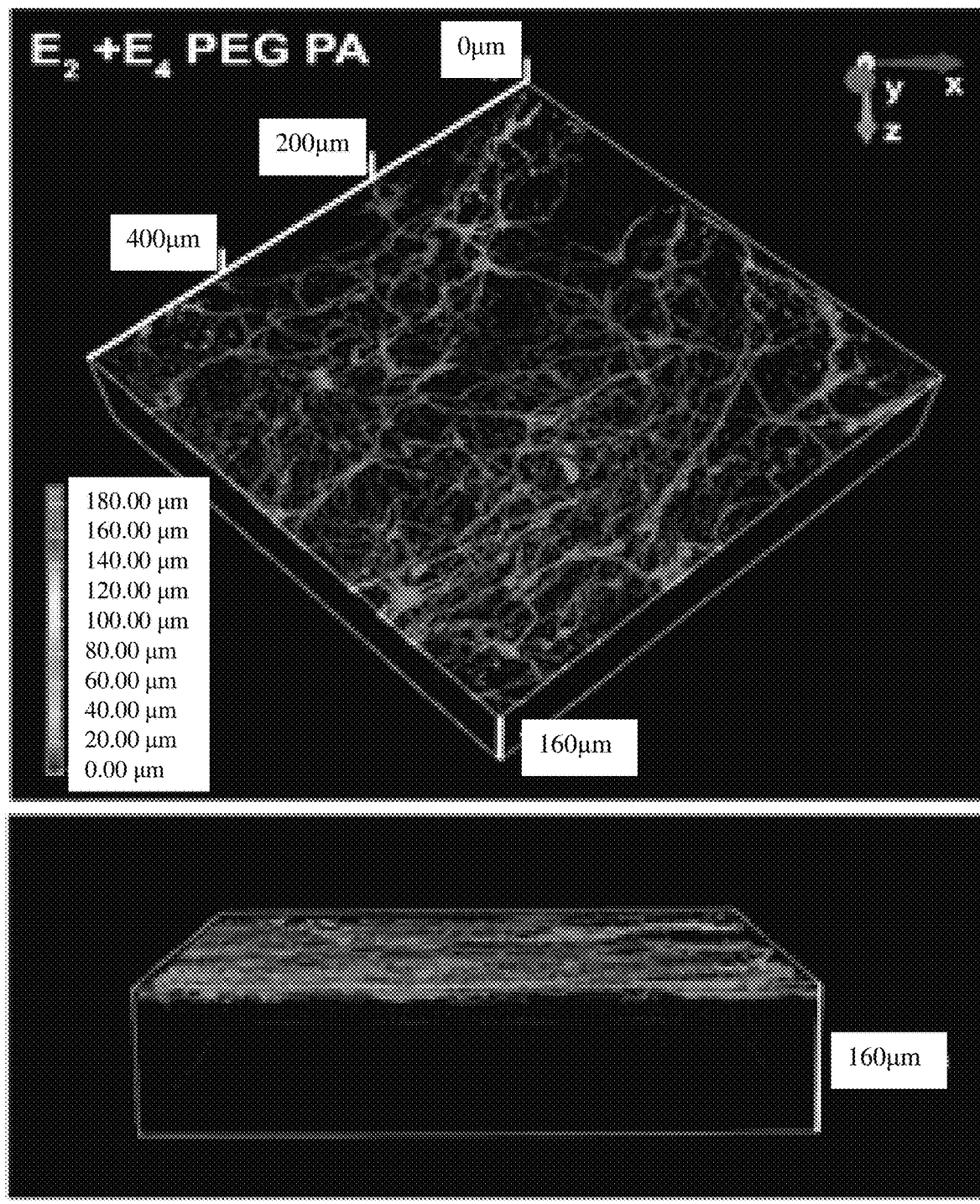
Figure 20D:
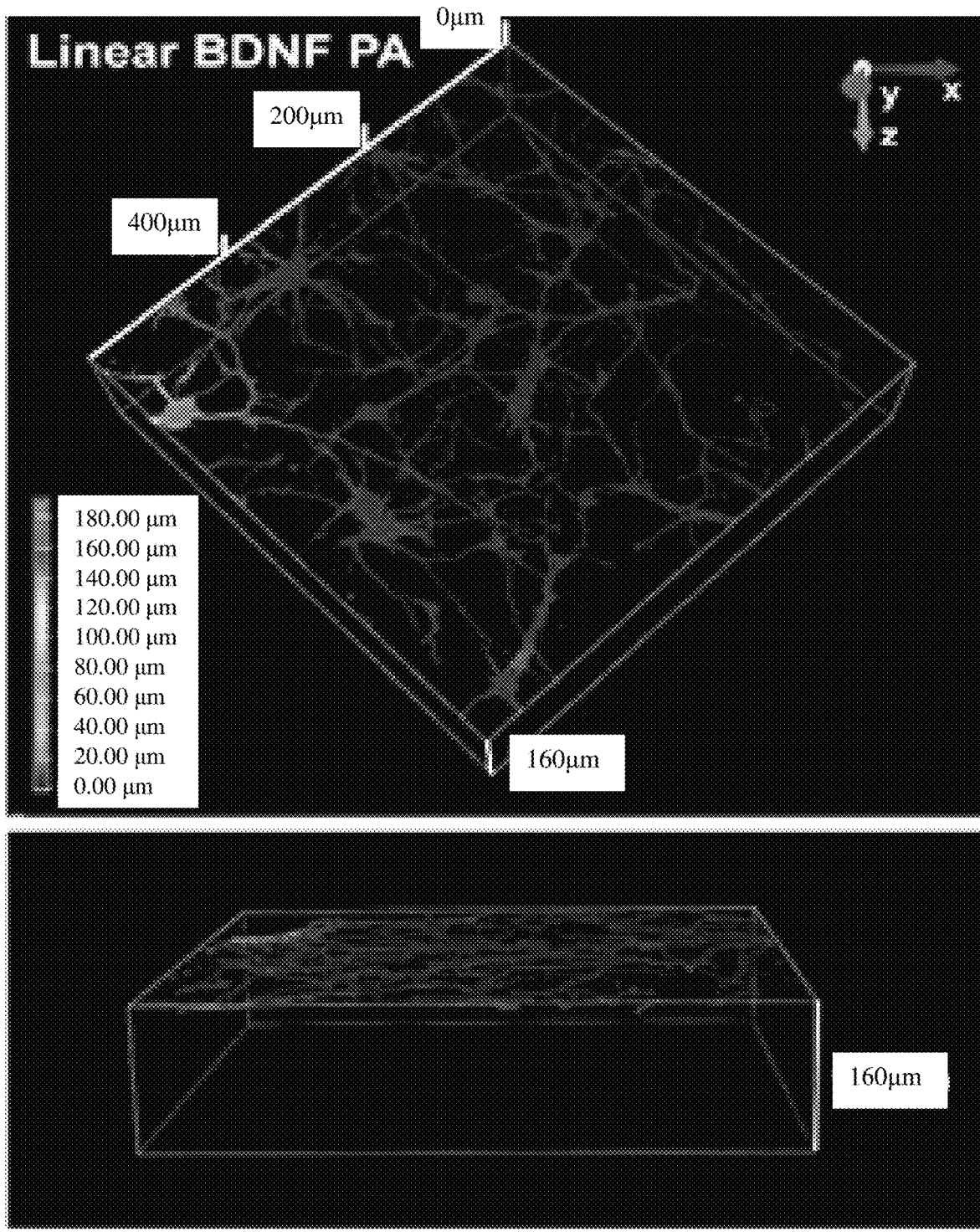
Figure 20:
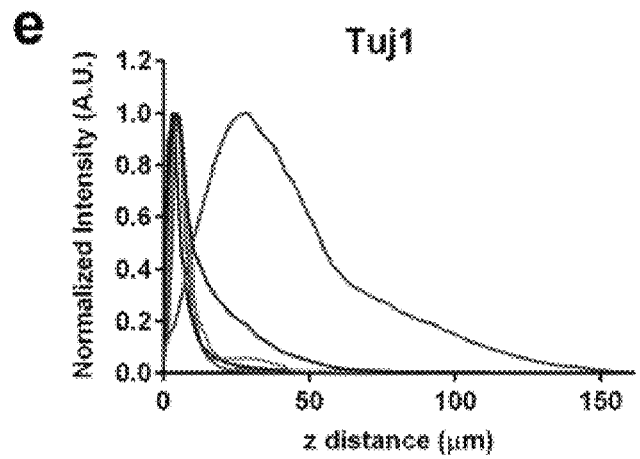
Figure 20:
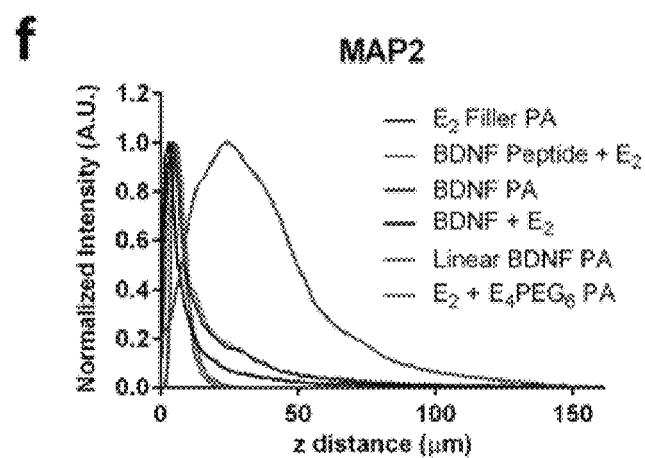
Figure 20:
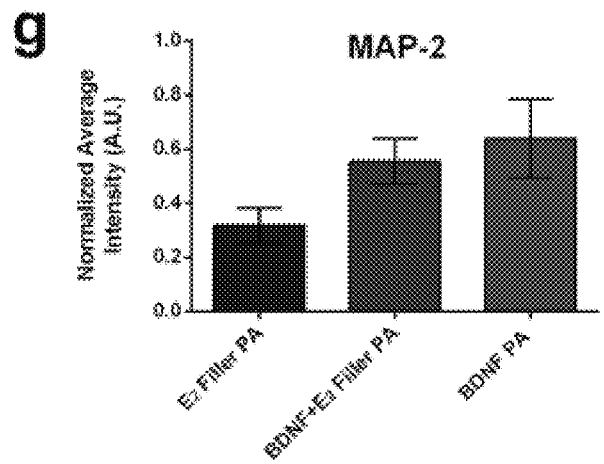

Gels were made using a commercial mold to maintain a uniform shape, size and degree of swelling (FIG. 19). Neurons were seeded on top of the gels for one week, and they exhibited neurite extensions and network formation in all conditions. Neuronal culture on BNDF PA gels and on BDNF+E2 Filler PAs exhibited a similarly mature phenotype characterized by MAP2 (FIG. 5F). The normalized average of MAP2 intensity was found to be almost twice as high on the BDNF PA (0.64±0.15) and BDNF+E2 Filler PA (0.55±0.08) gels than the E2 Filler PA gel (0.32±0.06) (FIG. 20G). Moreover, the distance that neurites infiltrated from the top of the scaffold was nearly four-and-a-half times higher in the BDNF PA (179.7±6.0 μm) compared with all the other conditions (BDNF+E2 Filler PA: 20.1±5.0 μm, Peptide+E2 Filler PA: 28.34±4.5 μm, and E2 Filler PA: 36.9±9.9 μm) (FIGS. 5G-H & 20). BDNF-TrkB phosphorylation induces neuronal migration and chemotaxis in cortical neurons and plays a significant role in axon guidance and growth during development and when applied after injury (Refs. 56-59; herein incorporated by reference in their entireties). The ability of the BDNF PA to induce neuronal migration, as well as dendritic and axonal infiltration is another indication of the PA's mimicry.

Experiments were conducted during development of embodiments herein to investigate whether the neurons infiltrated on the BDNF PA gels functionally mature to conduct information by generating action potentials. Cortical neurons were cultured for up to one week on BDNF PA gels and patch-clamp recordings were performed in whole-cell current-clamp mode. A higher number of action potentials were observed in neurons cultured on BDNF PA and BDNF+E2 filler PA gels relative to cells on the E2 Filler PA, indicative of a more excitable and therefore more mature cell phenotype (FIG. 5J). The electrophysiological recording and immunostaining together indicate that neurons inside the BDNF PA gels form a connected network of mature neurons, capable of propagating electrical information.

Example 2

Experiments were conducted during development of embodiments herein to provide behavioral scoring results from an in vivo study in which BDNF PA was used in a mouse model of spinal cord injury. In these experiments, increased functional hind limb recovery was observed in animals treated with BDNF PA over the control injections.

The spinal cord injury procedures used follow a standardized protocol to ensure a reproducible injury. Mice were anesthetized and their back is opened to reveal the vertebral column. The vertebral bone at T11 was surgically removed to reveal the spinal cord tissue. The mice were then transferred the impactor machine which is used to inflict a compression injury on the exposed spinal cord. The spinal cord was held in place using stereotactic clamps. The instrument inflicts a force of 70-80 kDynes and dwells in the place of the impact for 60 seconds to simulate a crush injury accident. This injury is quite severe. After each impact was performed, the instrument supplies a graph corresponding to the real force and trajectory of the impactor. This graph is used to compare and ensure that all animals receive an injury of the same nature. After the injury is inflicted, the animals were closed and allowed to rest for 24 hours.

The next day, the animals were re-opened and prepared for the "treatment" surgery. Before beginning the procedure, all animals underwent a behavioral assessment and mice with hind limb movement were discarded from the study. When the animal is re-opened, there was typically a dark, bruised area apparent where the crush injury took place the previous day. This is where the treatment was injected. A Hamilton syringe attached to a glass-pulled needle with a diameter of ~300 μm was used to puncture the bruised dermis of the tissue and the treatment was injected into the underlying tissue cavity. Treatment types include; saline, and the $C_{16}V_2A_2E_2$ ($E_2$) non-bioactive PA gel as negative controls, as well as the BDNF PA co-assembled at 20 mol % with the $E_2$ non-bioactive PA gel.

Figure 21:
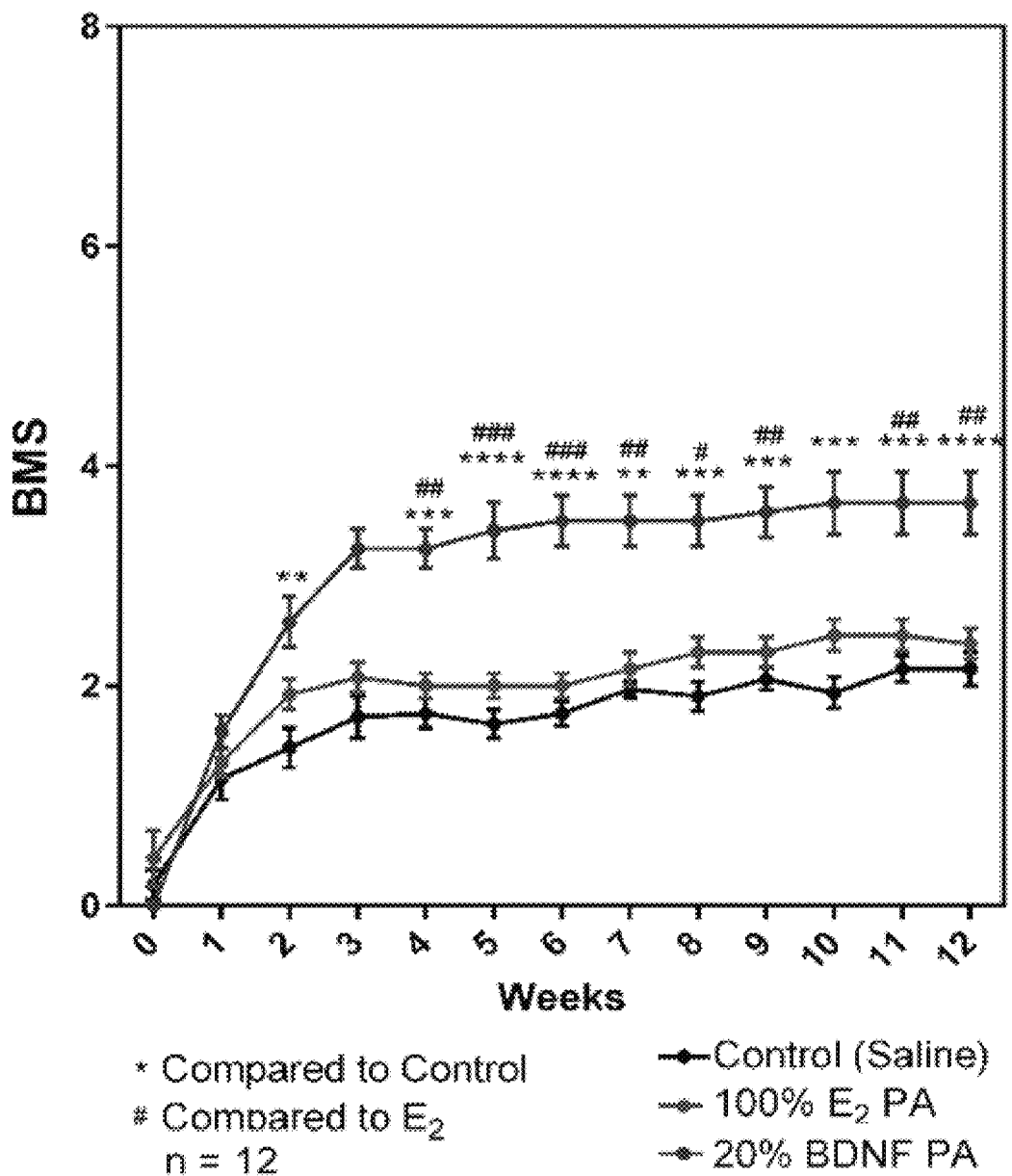
FIG. 21. Basso Mouse Scale scoring results from in vivo study where 12 mice were injected with BDNF PA material and assessed for hind limb functionality over 12 weeks following induced spinal cord injury.

After injection, the animals were closed and returned to cages to recover. Over the next 12 weeks, blinded hind limb behavioral scoring was performed to assess any functional changes (FIG. 21). A standardized "Basso Mouse Scale" was used (Basso et al. J Neurotrauma. 2006 May; 23(5):635-59.; herein incorporated by reference in its entirety). Two blinded researchers were either side of a runway where the mouse was guided to move in a straight line. As the mouse walks, each researcher grades the limb movement. Any discrepancies in evaluation were re-evaluated by a third researcher. The score for the two limbs was averaged and marked as the score for that animal.

Over a time course of 12 weeks, it was observed that the animals that were injected with the BDNF mimetic PA had a significant improvement in hindlimb function over those treated with the $E_2$ PA or saline solution alone. Within the first three weeks following the initial injury, the animals treated with the BDNF PA exhibited an increased rate of hindlimb improvement. These first weeks following the injury are critical and it is where most of the regeneration takes place. Although the increase in function began to plateau after these first three weeks, the final average limb behavioral scores were 3.7, 2.4, and 2.2 respectively for the BDNF PA, $E_2$ PA and saline solution. A score of a 2 is "Extensive ankle movement" according to the BMS guidelines and a score of a 4 is "occasional plantar stepping" for reference.

Example 3

Figure 22:
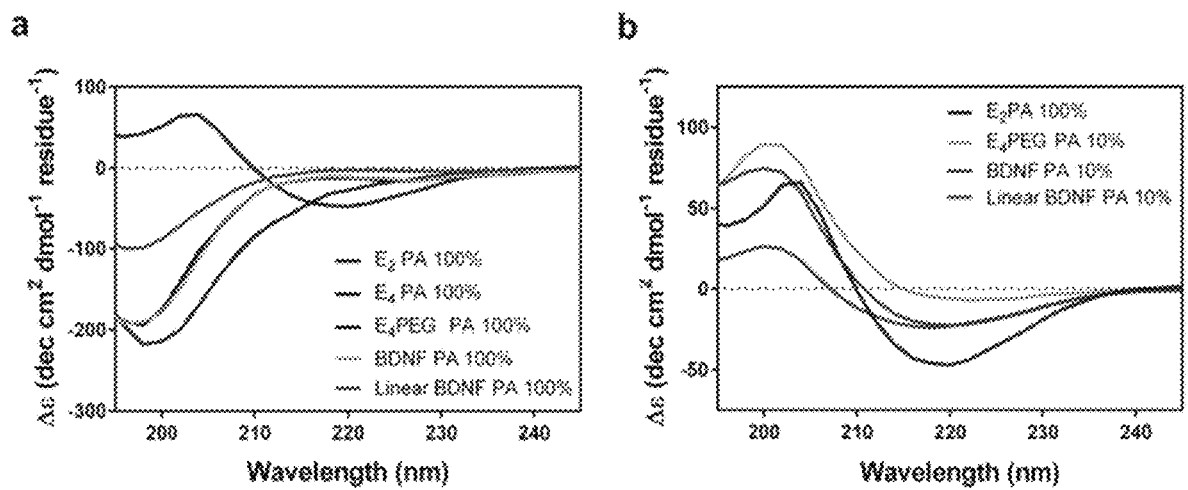
FIG. 22. Circular Dichroism (CD), High Tension (HT), and Fourier-Transform Infrared (FTIR) spectra of all PA conditions. (a, c) CD and HT curves of $E_2$ PA, $E_4$ PA, $E_4$PEG PA, Linear BDNF PA, and BDNF PA at 100 mol % and (b, d) CD and HT curves of $E_4$PEG, Linear BDNF and BDNF PAs co-assembled with $E_2$ PA at 10 mol %. (e, f) FTIR spectra for conditions referred in (a, b). Dashed line denotes position of β-sheet peak.
Figure 22:
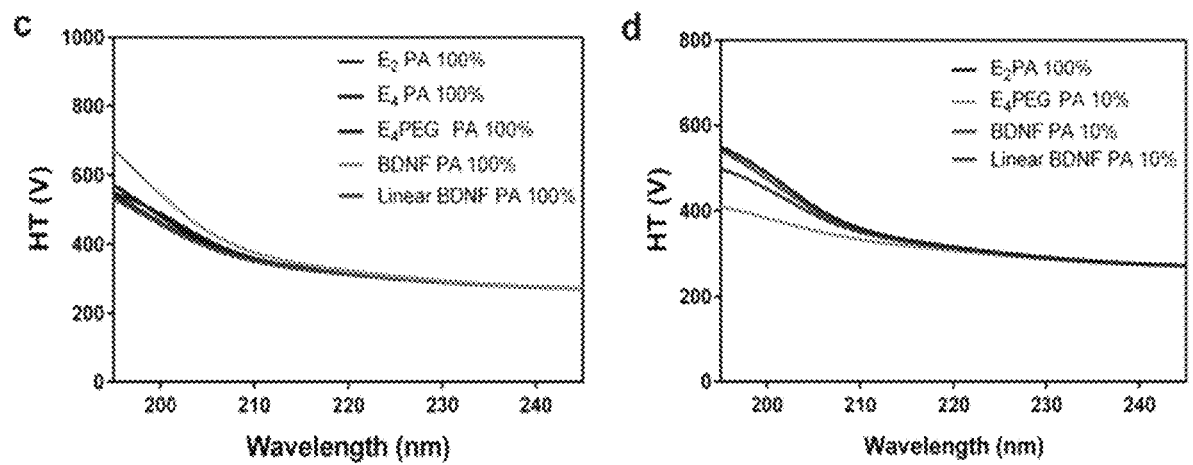
Figure 22:
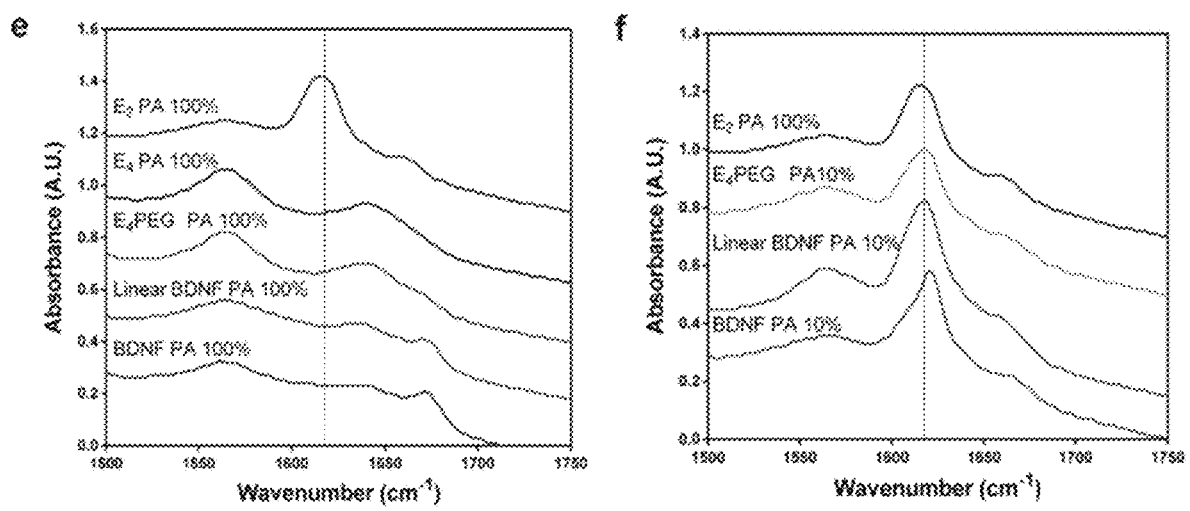

Circular Dichroism (CD), High Tension (HT), and Fourier-Transform Infrared (FTIR) spectroscopy were utilized to further characterize the PA materials described herein (FIG. 22).

Example 4

Figure 23:
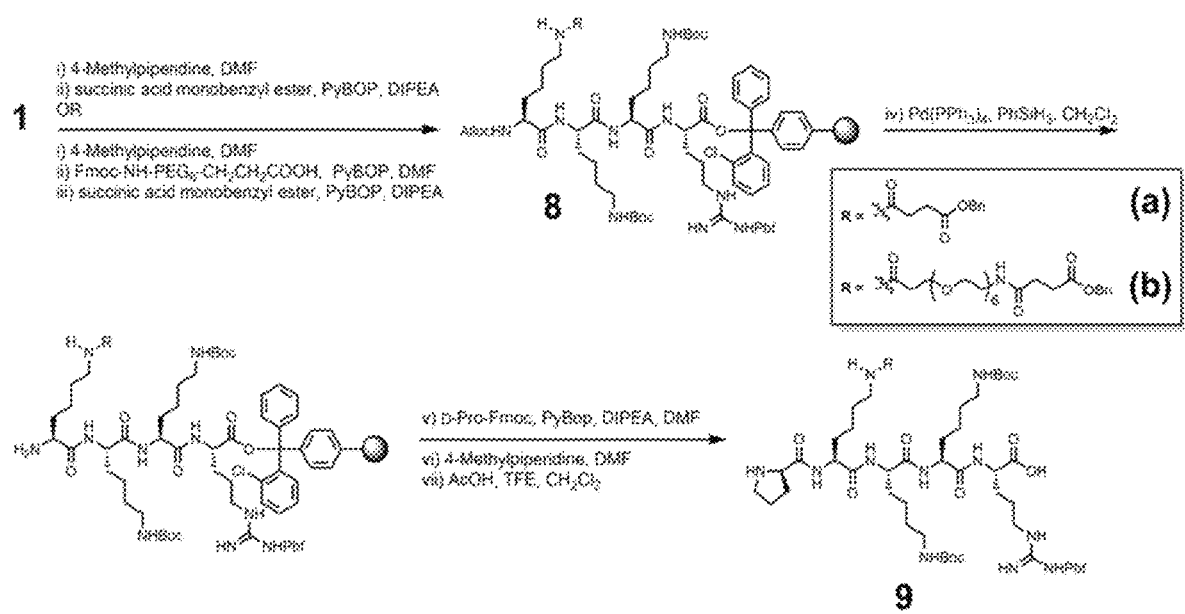
FIG. 23. Synthesis of Immobilized BDNF Peptide and PEG$_6$-BDNF Peptide.
Figure 23:
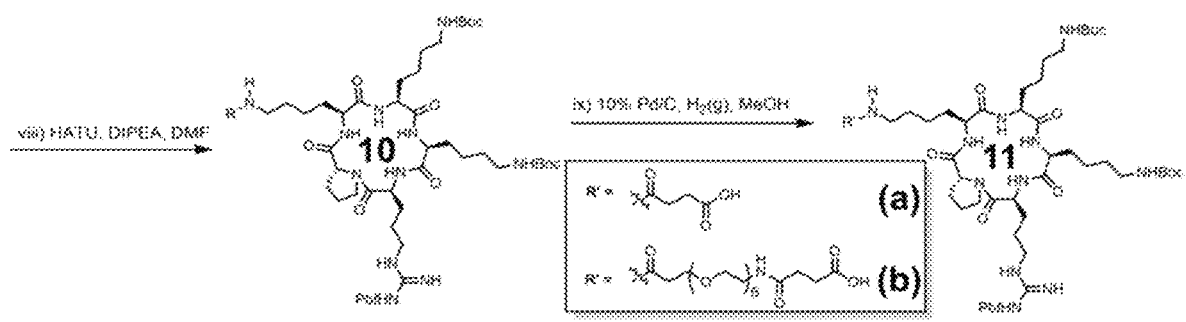
Figure 23:
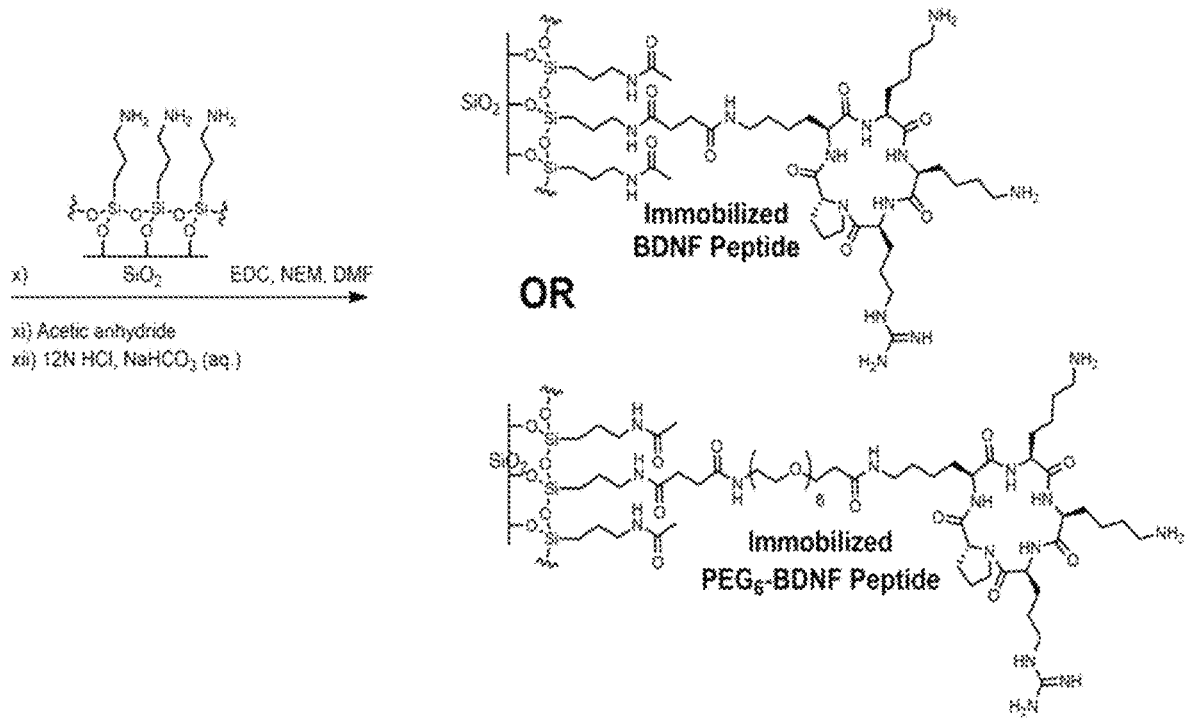
Figure 24:
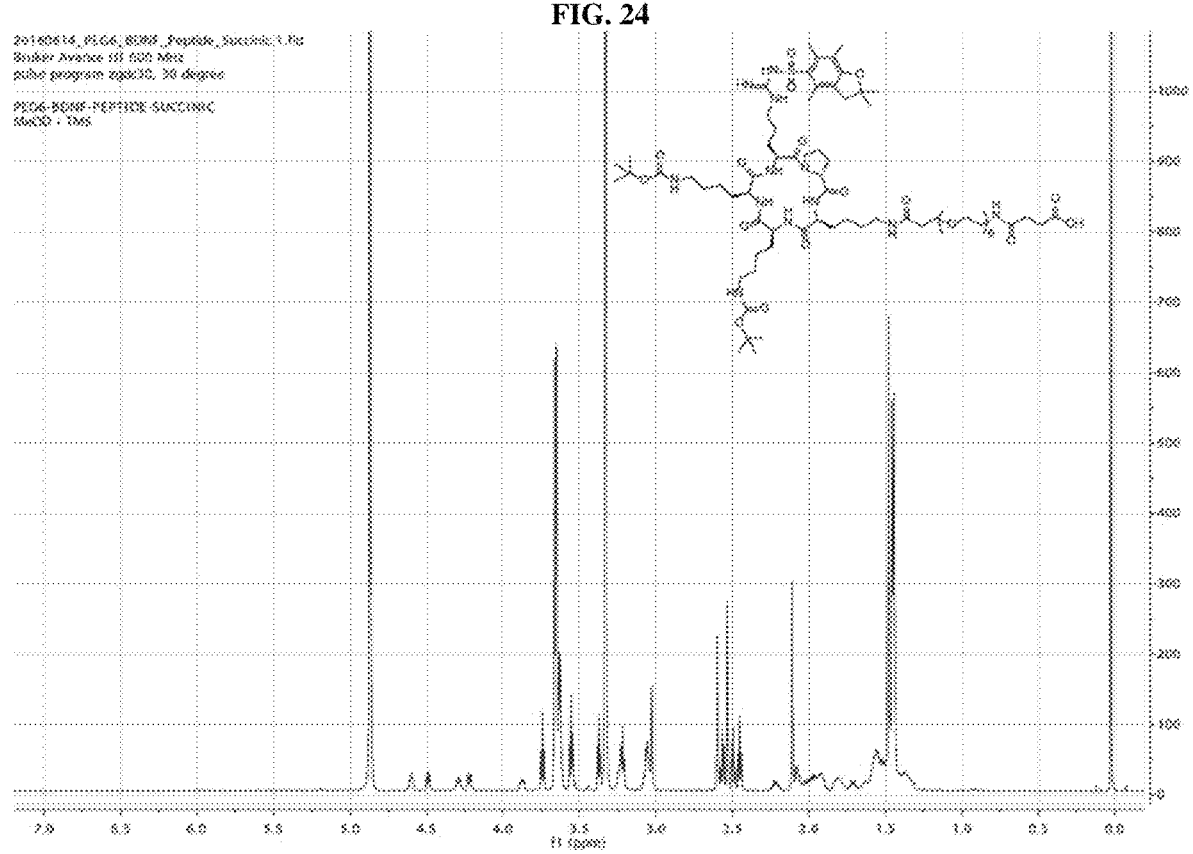
FIG. 24. $^1$H NMR spectrum of the PEG$_6$-BDNF Peptide for Immobilization 11b in MeOH-d$_4$ at 25° C.
Figure 25:
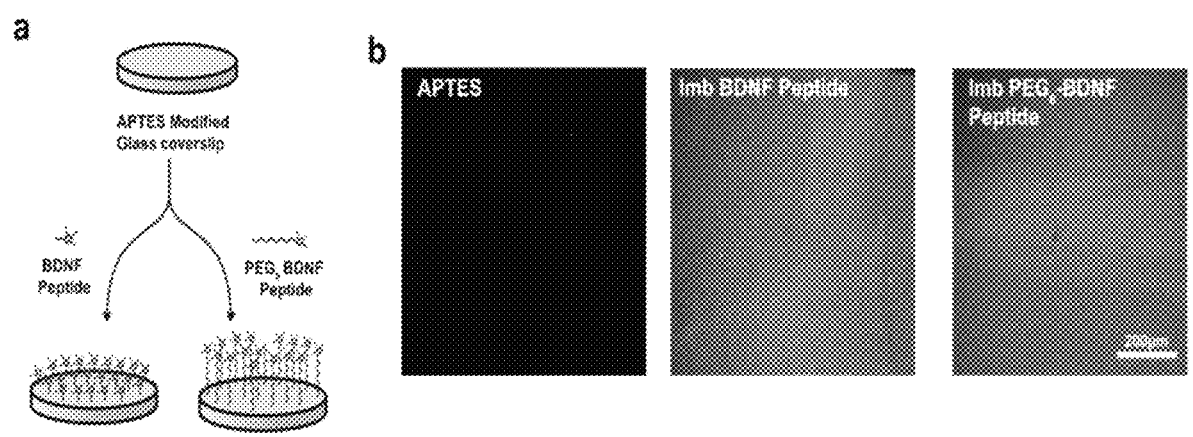
FIG. 25A-E. Viability assay of cells cultured on surfaces coated with the immobilized BDNF peptide. (a) Schematic showing BDNF Peptide and PEG$_6$-BDNF Peptide functionalized glass coverslips. (b) Confocal micrographs of glass coverslips coated with APTES, immobilized BDNF and PEG$_6$-BDNF peptides. FITC conjugated BDNF Peptide and PEG$_6$-BDNF Peptide are shown in green. (c) Bright field images of cells cultured on surfaces coated with APTES, the immobilized BDNF peptide, the immobilized PEG$_6$-BDNF peptide, and control poly-d-lysine (PDL) for 5 days in vitro. (d) Confocal micrographs of neuronal cells stained with calcein (live marker, green) and propidium iodide (dead marker, red) cultured on the coatings referred in (c). (e) Quantification of cell survival under conditions shown in (d). (values normalized to total number of cells).
Figure 25:
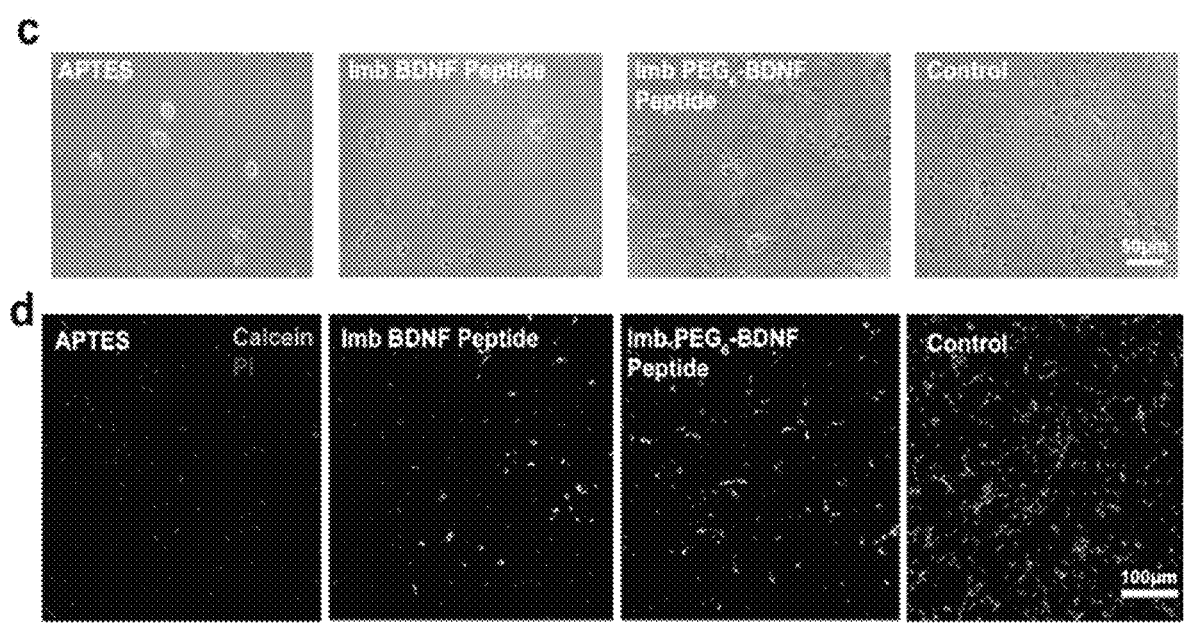
Figure 25:
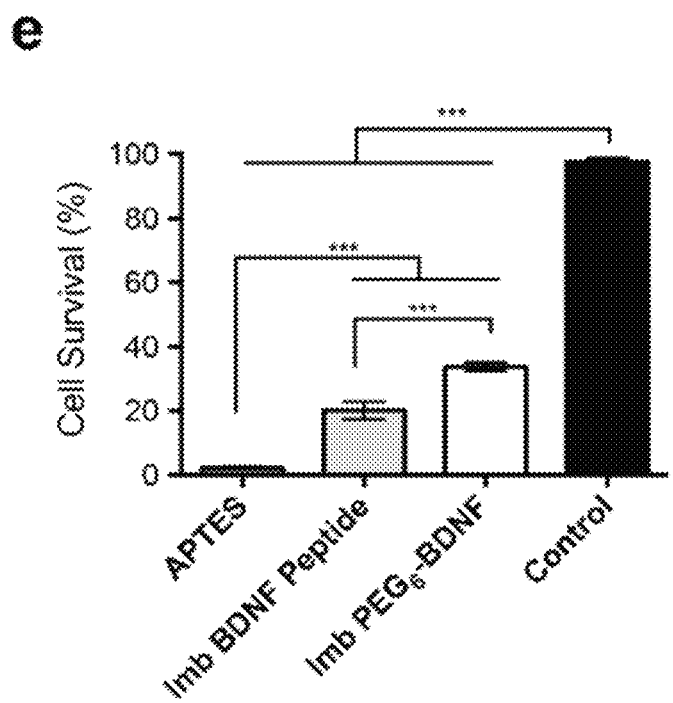
Figure 26:
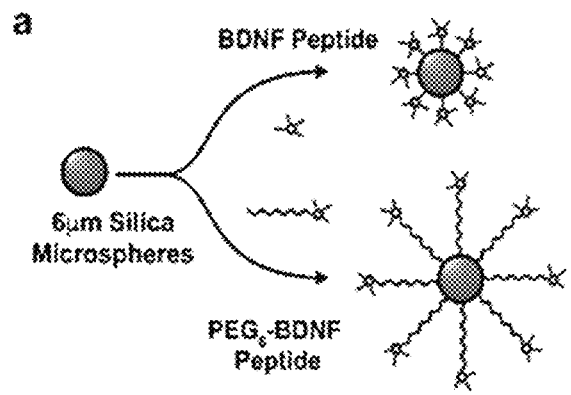
FIG. 26A-E. BDNF peptide immobilized on silica microsphere surfaces to probe TrkB receptor activation. (a) Schematic of BDNF mimetic and PEG$_6$-BDNF peptides attached to silica microspheres. (b) Confocal micrographs of silica microspheres coated with APTES, immobilized BDNF and PEG$_6$-BDNF peptides. Blank microspheres were used as control. (Left: Brightfield images of microspheres, Right: Fluorescent images of FITC conjugated peptide). (c) Bright field images of primary cortical neurons treated with silica microparticles functionalized with BDNF peptide, PEG$_6$-BDNF peptide, and APTES coated microparticles for 6 h. Blank particles, BDNF native protein, PEG$_6$-BDNF peptide in solution and starvation media were used as controls. (d) Western blot of p-TrkB and total TrkB receptor in neuronal cells treated using the conditions shown in (c). (e) Densitometry analysis of p-TrkB of the conditions shown in (d). (Intensity values normalized to TrkB).
Figure 26:
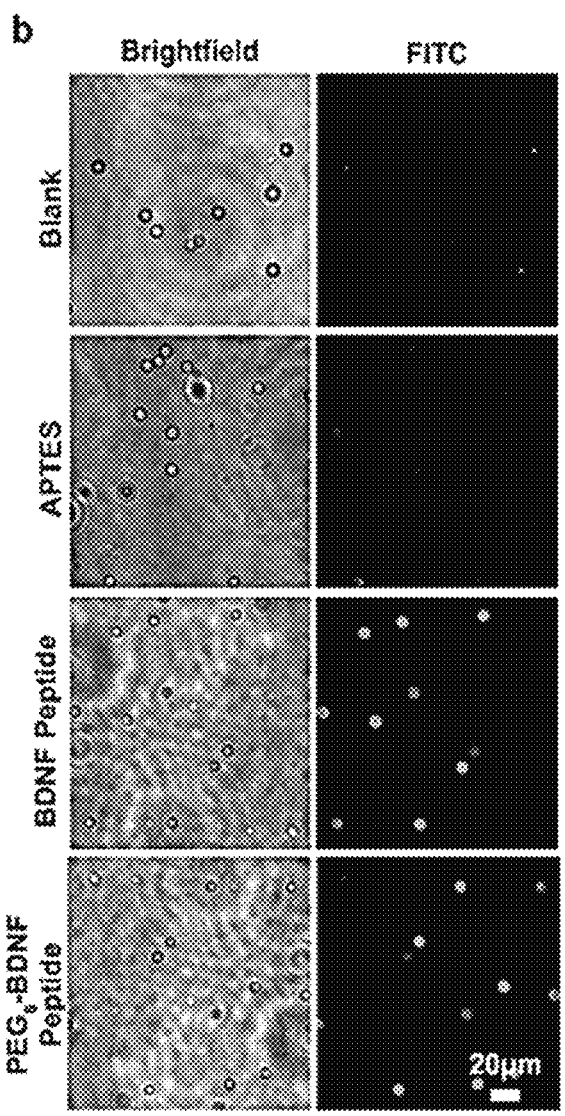
Figure 26:
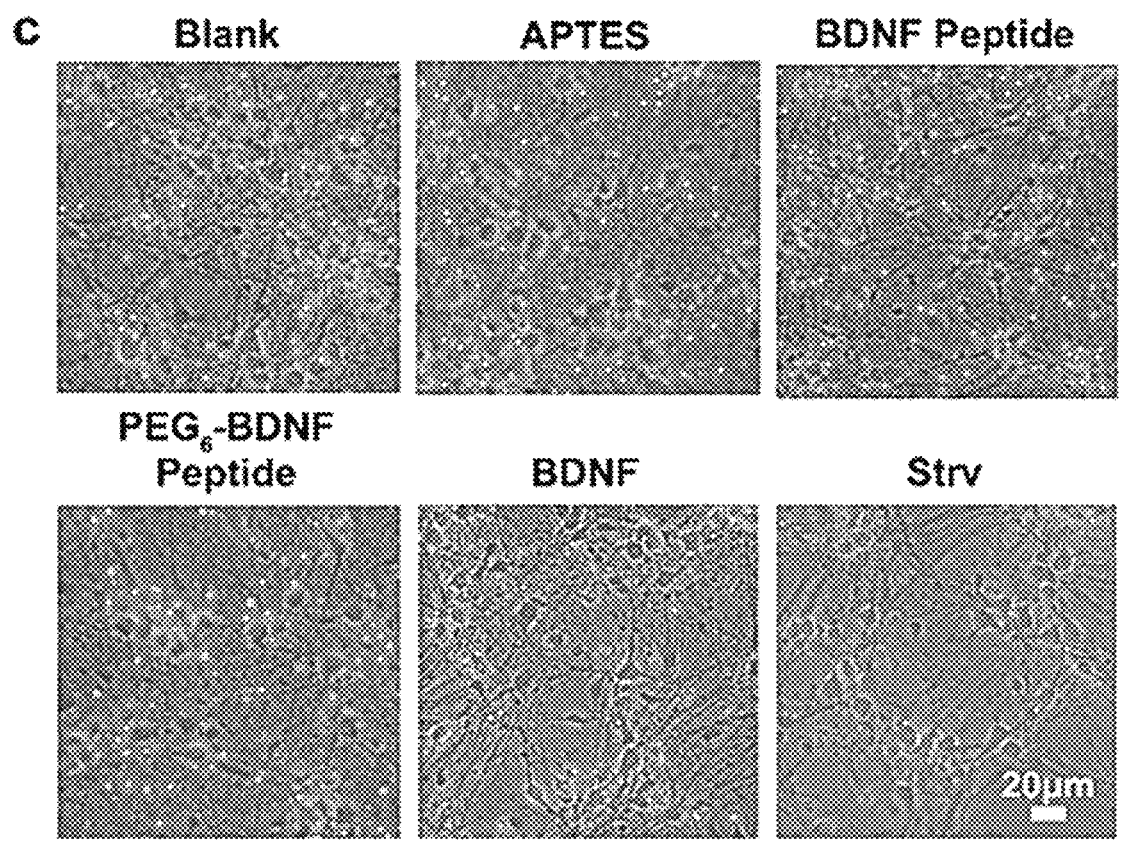
Figure 26:
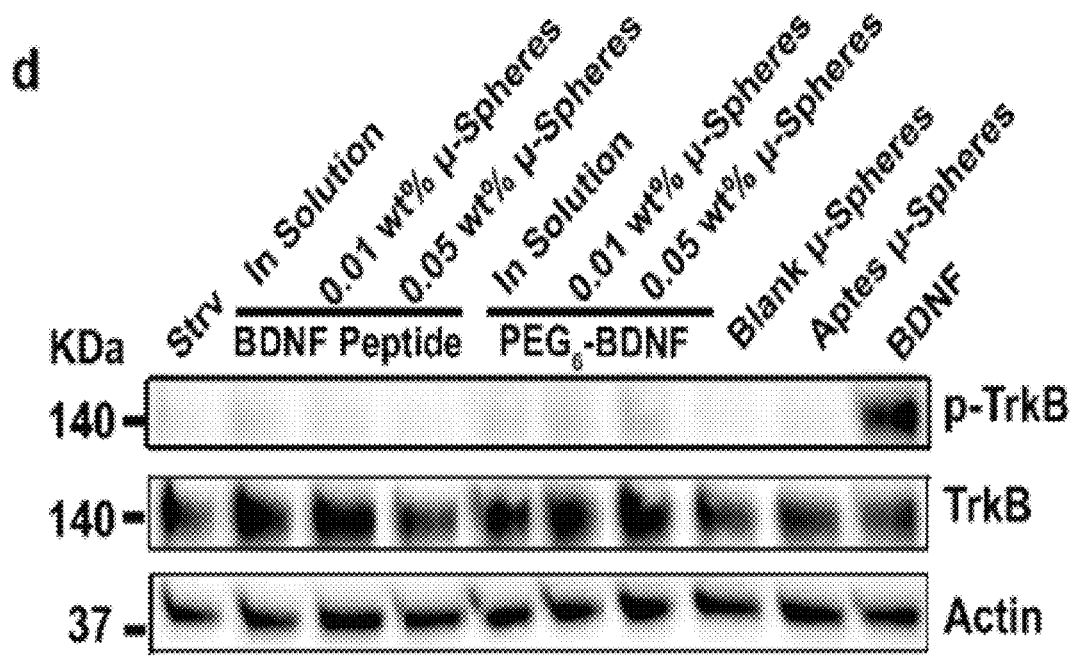
Figure 26:
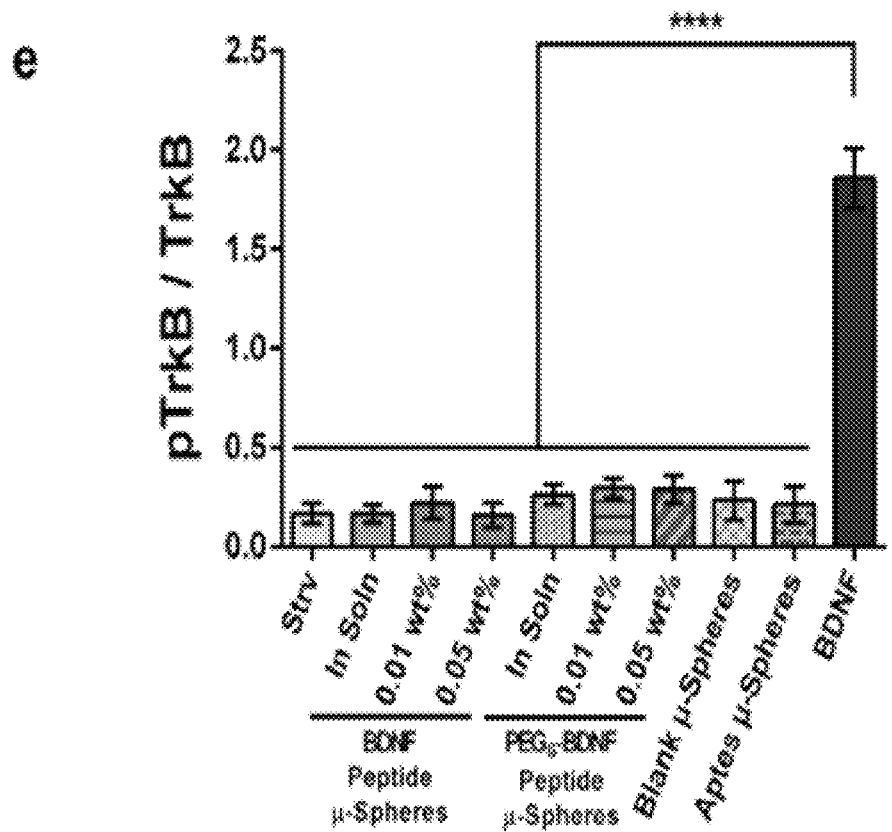

Experiments were conducted during development of embodiments herein to demonstrate to repeat receptor activation experiments with an additional control. Initial experiments utilized a control in which the BDNF mimetic peptide was immobilized onto glass coverslips and silica microspheres and demonstrated that it had no effect on cells. For the additional control, a PEG6 linker was added between the BDNF mimetic peptide and the glass or silica surface. The results from these experiments demonstrated that this additional control was not able to activate the BDNF-specific receptor, TrkB, in the same manner as the BDNF-PA (See FIG. 23 (synthesis Schematic of PEG6 BDNF Peptide Control), FIG. 24 (NMR Characterization of PEG6-BDNF Peptide), FIG. 25 (PEG6 BDNF Peptide Immobilized on Glass Coverslips—Cell Viability Assay), and FIG. 26 (PEG6 BDNF Immobilized on Silica Microspheres—Receptor Activation Assay)).

REFERENCES

The following references, some of which are cited above by number, are herein incorporated by reference in their entireties.
1. Eide, F. F.; Lowenstein, D. H.; Reichardt, L. F., Neurotrophins and their receptors—current concepts and implications for neurologic disease. Exp Neurol 1993, 121 (2), 200-14.
2. Ibáñez, C. F., Neurotrophic factors: from structure-function studies to designing effective therapeutics. Trends Biotechnol 1995, 13 (6), 217-27.
3. Hallböök, F., Evolution of the vertebrate neurotrophin and Trk receptor gene families. Curr Opin Neurobiol 1999, 9 (5), 616-21.
4. Park, H.; Poo, M. M., Neurotrophin regulation of neural circuit development and function. Nat Rev Neurosci 2013, 14 (1), 7-23.
5. Lu, P.; Jones, L. L.; Tuszynski, M. H., BDNF-expressing marrow stromal cells support extensive axonal growth at sites of spinal cord injury. Exp Neurol 2005, 191 (2), 344-60.
6. Huang, E. J.; Reichardt, L. F., Trk receptors: roles in neuronal signal transduction. Annu Rev Biochem 2003, 72, 609-42.
7. Rodriguez-Tébar, A.; Dechant, G.; Barde, Y. A., Binding of brain-derived neurotrophic factor to the nerve growth factor receptor. Neuron 1990, 4 (4), 487-92.
8. Gentry, J. J.; Barker, P. A.; Carter, B. D., The p75 neurotrophin receptor: multiple interactors and numerous functions. Prog Brain Res 2004, 146, 25-39.
9. Lu, B.; Nagappan, G.; Guan, X.; Nathan, P. J.; Wren, P., BDNF-based synaptic repair as a disease-modifying strategy for neurodegenerative diseases. Nat Rev Neurosci 2013, 14 (6), 401-16.
10. Barde, Y. A.; Edgar, D.; Thoenen, H., Purification of a new neurotrophic factor from mammalian brain. EMBO J 1982, 1 (5), 549-53.
11. Nagahara, A. H.; Merrill, D. A.; Coppola, G.; Tsukada, S.; Schroeder, B. E.; Shaked, G. M.; Wang, L.; Blesch, A.; Kim, A.; Conner, J. M.; Rockenstein, E.; Chao, M. V.; Koo, E. H.; Geschwind, D.; Masliah, E.; Chiba, A. A.; Tuszynski, M. H., Neuroprotective effects of brain-derived neurotrophic factor in rodent and primate models of Alzheimer's disease. Nat Med 2009, 15 (3), 331-7.
12. Nagahara, A. H.; Tuszynski, M. H., Potential therapeutic uses of BDNF in neurological and psychiatric disorders. Nature Reviews Drug Discovery 2011, 10 (3), 209-219.
13. Rauskolb, S.; Zagrebelsky, M.; Dreznjak, A.; Deogracias, R.; Matsumoto, T.; Wiese, S.; Erne, B.; Sendtner, M.; Schaeren-Wiemers, N.; Korte, M.; Barde, Y. A., Global deprivation of brain-derived neurotrophic factor in the CNS reveals an area-specific requirement for dendritic growth. J Neurosci 2010, 30 (5), 1739-49.
14. Tanaka, J.; Horiike, Y.; Matsuzaki, M.; Miyazaki, T.; Ellis-Davies, G. C.; Kasai, H., Protein synthesis and neurotrophin-dependent structural plasticity of single dendritic spines. Science 2008, 319 (5870), 1683-7.
15. Connor, B.; Young, D.; Yan, Q.; Fault, R. L.; Synek, B.; Dragunow, M., Brain-derived neurotrophic factor is reduced in Alzheimer's disease. Brain Res Mol Brain Res 1997, 49 (1-2), 71-81.
16. Mogi, M.; Togari, A.; Kondo, T.; Mizuno, Y.; Komure, O.; Kuno, S.; Ichinose, H.; Nagatsu, T., Brain-derived growth factor and nerve growth factor concentrations are decreased in the substantia nigra in Parkinson's disease. Neurosci Lett 1999, 270 (1), 45-8.
17. Pardridge, W. M., Neurotrophins, neuroprotection and the blood-brain barrier. Curr Opin Investig Drugs 2002, 3 (12), 1753-7.
18. Ochs, G.; Penn, R. D.; York, M.; Giess, R.; Beck, M.; Tonn, J.; Haigh, J.; Malta, E.; Traub, M.; Sendtner, M.; Toyka, K. V., A phase I/II trial of recombinant methionyl human brain derived neurotrophic factor administered by intrathecal infusion to patients with amyotrophic lateral sclerosis. Amyotroph Lateral Scler Other Motor Neuron Disord 2000, 1 (3), 201-6.
19. Wellmer, A.; Misra, V. P.; Sharief, M. K.; Kopelman, P. G.; Anand, P., A double-blind placebo-controlled clinical trial of recombinant human brain-derived neurotrophic factor (rhBDNF) in diabetic polyneuropathy. J Peripher Nery Syst 2001, 6 (4), 204-10.
20. Thoenen, H.; Sendtner, M., Neurotrophins: from enthusiastic expectations through sobering experiences to rational therapeutic approaches. Nat Neurosci 2002, 5 Suppl, 1046-50.
21. O'Leary, P. D.; Hughes, R. A., Design of potent peptide mimetics of brain-derived neurotrophic factor. Journal of Biological Chemistry 2003, 278 (28), 25738-25744.
22. O'Leary, P. D.; Hughes, R. A., Structure-activity relationships of conformationally constrained peptide analogues of loop 2 of brain-derived neurotrophic factor. J Neurochem 1998, 70 (4), 1712-21.
23. Fletcher, J. M.; Hughes, R. A., Novel monocyclic and bicyclic loop mimetics of brain-derived neurotrophic factor. Journal of Peptide Science 2006, 12 (8), 515-524.
24. Fletcher, J. M.; Morton, C. J.; Zwar, R. A.; Murray, S. S.; O'Leary, P. D.; Hughes, R. A., Design of a Conformationally Defined and Proteolytically Stable Circular Mimetic of Brain-derived Neurotrophic Factor. Journal of Biological Chemistry 2008, 283 (48), 33375-33383.
25. Gonsalvez, D. G.; Tran, G.; Fletcher, J. L.; Hughes, R. A.; Hodgkinson, S.; Wood, R. J.; Yoo, S. W.; De Silva, M.; Agnes, W. W.; McLean, C.; Kennedy, P.; Kilpatrick, T. J.; Murray, S. S.; Xiao, J., A Brain-Derived Neurotrophic Factor-Based p75NTR Peptide Mimetic Ameliorates Experimental Autoimmune Neuritis Induced Axonal Pathology and Demyelination. eNeuro 2017, 4 (3).
26. Hartgerink, J. D.; Beniash, E.; Stupp, S. I., Self-assembly and mineralization of peptide-amphiphile nanofibers. Science 2001, 294 (5547), 1684-8.
27. Zhang, S.; Greenfield, M. A.; Mata, A.; Palmer, L. C.; Bitton, R.; Mantei, J. R.; Aparicio, C.; de la Cruz, M. O.; Stupp, S. I., A self-assembly pathway to aligned monodomain gels. Nat Mater 2010, 9 (7), 594-601.
28. Pan, L.; North, H. A.; Sahni, V.; Jeong, S. J.; McGuire, T. L.; Berns, E. J.; Stupp, S. I.; Kessler, J. A., beta1-

28. Integrin and integrin linked kinase regulate astrocytic differentiation of neural stem cells. PLoS One 2014, 9 (8), e104335.
29. Berns, E. J.; Álvarez, Z.; Goldberger, J. E.; Boekhoven, J.; Kessler, J. A.; Kuhn, H. G.; Stupp, S. I., A tenascin-C mimetic peptide amphiphile nanofiber gel promotes neurite outgrowth and cell migration of neurosphere-derived cells. Acta Biomater 2016, 37, 50-8.
30. Rubert Pérez, C. M.; Álvarez, Z.; Chen, F.; Aytun, T.; Stupp, S. I., Mimicking the Bioactivity of Fibroblast Growth Factor-2 Using Supramolecular Nanoribbons. ACS Biomater Sci Eng 2017, 3 (9), 2166-2175.
31. Webber, M. J.; Tongers, J.; Newcomb, C. J.; Marquardt, K. T.; Bauersachs, J.; Losordo, D. W.; Stupp, S. I., Supramolecular nanostructures that mimic VEGF as a strategy for ischemic tissue repair. Proc Natl Acad Sci USA 2011, 108 (33), 13438-43.
32. Fletcher, J. M.; Hughes, R. A., Modified low molecular weight cyclic peptides as mimetics of BDNF with improved potency, proteolytic stability and transmembrane passage in vitro. Bioorganic & Medicinal Chemistry 2009, 17 (7), 2695-2702.
33. Sur, S.; Tantakitti, F.; Matson, J. B.; Stupp, S. I., Epitope topography controls bioactivity in supramolecular nanofibers. Biomater Sci 2015, 3 (3), 520-32.
34. Goldberger, J. E.; Berns, E. J.; Bitton, R.; Newcomb, C. J.; Stupp, S. I., Electrostatic control of bioactivity. Angew Chem Int Ed Engl 2011, 50 (28), 6292-5.
35. Burkhalter, J.; Fiumelli, H.; Allaman, I.; Chatton, J. Y.; Martin, J. L., Brain-derived neurotrophic factor stimulates energy metabolism in developing cortical neurons. J Neurosci 2003, 23 (23), 8212-20.
36. Ji, Y.; Pang, P. T.; Feng, L.; Lu, B., Cyclic AMP controls BDNF-induced TrkB phosphorylation and dendritic spine formation in mature hippocampal neurons. Nat Neurosci 2005, 8 (2), 164-72.
37. Brewer, G. J., Serum-free B27/neurobasal medium supports differentiated growth of neurons from the striatum, substantia nigra, septum, cerebral cortex, cerebellum, and dentate gyrus. J Neurosci Res 1995, 42 (5), 674-83.
38. Tapley, P.; Lamballe, F.; Barbacid, M., K252a is a selective inhibitor of the tyrosine protein kinase activity of the trk family of oncogenes and neurotrophin receptors. Oncogene 1992, 7 (2), 371-81.
39. Olbrich, K. C.; Andersen, T. T.; Blumenstock, F. A.; Bizios, R., Surfaces modified with covalently-immobilized adhesive peptides affect fibroblast population motility. Biomaterials 1996, 17 (8), 759-64.
40. Kang, H.; Schuman, E. M., Long-lasting neurotrophin-induced enhancement of synaptic transmission in the adult hippocampus. Science 1995, 267 (5204), 1658-62.
41. Ji, Y.; Lu, Y.; Yang, F.; Shen, W.; Tang, T. T.; Feng, L.; Duan, S.; Lu, B., Acute and gradual increases in BDNF concentration elicit distinct signaling and functions in neurons. Nat Neurosci 2010, 13 (3), 302-9.
42. Figurov, A.; Pozzo-Miller, L. D.; Olafsson, P.; Wang, T.; Lu, B., Regulation of synaptic responses to high-frequency stimulation and LTP by neurotrophins in the hippocampus. Nature 1996, 381 (6584), 706-9.
43. Martínez, A.; Alcántara, S.; Borrell, V.; Del Rio, J. A.; Blasi, J.; Otal, R.; Campos, N.; Boronat, A.; Barbacid, M.; Silos-Santiago, I.; Soriano, E., TrkB and TrkC signaling are required for maturation and synaptogenesis of hippocampal connections. J Neurosci 1998, 18 (18), 7336-50.
44. Cohen-Cory, S.; Kidane, A. H.; Shirkey, N. J.; Marshak, S., Brain-derived neurotrophic factor and the development of structural neuronal connectivity. Dev Neurobiol 2010, 70 (5), 271-88.
45. Hu, B.; Nikolakopoulou, A. M.; Cohen-Cory, S., BDNF stabilizes synapses and maintains the structural complexity of optic axons in vivo. Development 2005, 132 (19), 4285-98.
46. Gorski, J. A.; Zeiler, S. R.; Tamowski, S.; Jones, K. R., Brain-derived neurotrophic factor is required for the maintenance of cortical dendrites. J Neurosci 2003, 23 (17), 6856-65.
47. Chao, M. V., Neurotrophins and their receptors: a convergence point for many signalling pathways. Nat Rev Neurosci 2003, 4 (4), 299-309.
48. Gottschalk, W. A.; Jiang, H.; Tartaglia, N.; Feng, L.; Figurov, A.; Lu, B., Signaling mechanisms mediating BDNF modulation of synaptic plasticity in the hippocampus. Learn Mem 1999, 6 (3), 243-56.
49. Okada, D.; Yamagishi, S.; Sugiyama, H., Differential effects of phospholipase inhibitors in long-term potentiation in the rat hippocampal mossy fiber synapses and Schaffer/commissural synapses. Neurosci Lett 1989, 100 (1-3), 141-6.
50. Thomas, G. M.; Huganir, R. L., MAPK cascade signalling and synaptic plasticity. Nat Rev Neurosci 2004, 5 (3), 173-83.
51. Yoshii, A.; Constantine-Paton, M., Postsynaptic BDNF-TrkB signaling in synapse maturation, plasticity, and disease. Dev Neurobiol 2010, 70 (5), 304-22.
52. Huang, E. J.; Reichardt, L. F., Neurotrophins: Roles in Neuronal Development and Function. Annual Review of Neuroscience 2001, 24 (1), 677-736.
53. Dehmelt, L.; Halpain, S., The MAP2/Tau family of microtubule-associated proteins. Genome Biol 2005, 6 (1), 204.
54. Meyer, D.; Bonhoeffer, T.; Scheuss, V., Balance and stability of synaptic structures during synaptic plasticity. Neuron 2014, 82 (2), 430-43.
55. Discher, D. E.; Mooney, D. J.; Zandstra, P. W., Growth factors, matrices, and forces combine and control stem cells. Science 2009, 324 (5935), 1673-7.
56. Chiaramello, S.; Dalmasso, G.; Bezin, L.; Marcel, D.; Jourdan, F.; Peretto, P.; Fasolo, A.; De Marchis, S., BDNF/TrkB interaction regulates migration of SVZ precursor cells via PI3-K and MAP-K signalling pathways. Eur J Neurosci 2007, 26 (7), 1780-90.
57. Behar, T. N.; Dugich-Djordjevic, M. M.; Li, Y. X.; Ma, W.; Somogyi, R.; Wen, X.; Brown, E.; Scott, C.; McKay, R. D.; Barker, J. L., Neurotrophins stimulate chemotaxis of embryonic cortical neurons. Eur J Neurosci 1997, 9 (12), 2561-70.
58. Huang, E. J.; Reichardt, L. F., Neurotrophins: roles in neuronal development and function. Annu Rev Neurosci 2001, 24, 677-736.
59. Blesch, A.; Tuszynski, M. H., Transient growth factor delivery sustains regenerated axons after spinal cord injury. Journal of Neuroscience 2007, 27 (39), 10535-10545.
60. Sleep, E.; Cosgrove, B. D.; McClendon, M. T.; Preslar, A. T.; Chen, C. H.; Sangji, M. H.; Pérez, C. M. R.; Haynes, R. D.; Meade, T. J.; Blau, H. M.; Stupp, S. I., Injectable biomimetic liquid crystalline scaffolds enhance muscle stem cell transplantation. Proc Natl Acad Sci USA 2017, 114 (38), E7919-E7928.

61. Sargent, D. F.; Schwyzer, R., Membrane lipid phase as catalyst for peptide-receptor interactions. Proc Natl Acad Sci USA 1986, 83 (16), 5774-8.

The invention claimed is:

1. A composition comprising brain derived neurotrophic factor (BDNF) peptide amphiphiles, the BDNF peptide amphiphiles comprising a hydrophobic non-peptide tail, a structured peptide segment of 2-8 non-polar residues, a charged peptide segment, and a BDNF peptide comprising RKK(aK)(dP):

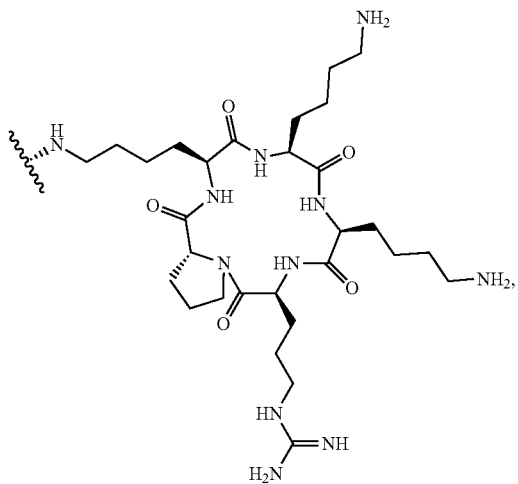

wherein the hydrophobic non-peptide tail is linked to the structured peptide segment, wherein the structured peptide segment is linked to the charged peptide segment.

2. The composition of claim 1, wherein the hydrophobic non-peptide tail comprises an 8-24 carbon alkyl chain ($C_{8-24}$).

3. The composition of claim 1, wherein the structured peptide segment comprises VVAA (SEQ ID NO: 2) or AAVV (SEQ ID NO: 7).

4. The composition of claim 1, wherein the charged peptide segment comprises an acidic, basic, or zwitterionic peptide segment.

5. The composition of claim 1, wherein the charged peptide segment comprises EE or KK.

6. The composition of claim 5, wherein the peptide amphiphile comprises EEEEAAVV-$C_{8-24}$ (SEQ ID NO: 3).

7. The composition of claim 1, wherein the peptide amphiphile comprises RKK(aK)(dP)-(PEG6 Spacer)-EE-EEAAVV-$C_{16}$ (SEQ ID NO: 5).

8. A nanofiber comprising a self-assembled complex of the BDNF peptide amphiphiles of claim 1.

9. The nanofiber of claim 8, further comprising filler peptide amphiphiles, wherein the filler peptide amphiphiles comprise a hydrophobic non-peptide tail, a structured peptide segment, and a charged peptide segment, but do not comprise a bioactive moiety.

10. The nanofiber of claim 9, wherein the filler peptide amphiphile comprises EEAAVV-$C_{8-24}$ (SEQ ID NO: 6).

11. A method comprising administering a pharmaceutically formulated nanofiber of claim 8 to a subject.

12. The method of claim 11, wherein the nanofiber is administered by injection.

* * * * *

```
                          SEQUENCE LISTING

<160> NUMBER OF SEQ ID NOS: 10

<210> SEQ ID NO 1
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = d-Proline

<400> SEQUENCE: 1

Arg Lys Lys Ala Xaa
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Val Val Ala Ala
1

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Glu Glu Glu Glu Ala Ala Val Val
1               5

<210> SEQ ID NO 4
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = d-Proline
<220> FEATURE:
<221> NAME/KEY: CHAIN
<222> LOCATION: (13)..(13)
<223> OTHER INFORMATION: 8-24 carbon alkyl chain

<400> SEQUENCE: 4

Arg Lys Lys Lys Xaa Glu Glu Glu Glu Ala Ala Val Val
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (5)..(5)
<223> OTHER INFORMATION: Xaa = d-Proline
<220> FEATURE:
<221> NAME/KEY: CHAIN
<222> LOCATION: (13)..(13)
<223> OTHER INFORMATION: 16 carbon alkyl chain

<400> SEQUENCE: 5

Arg Lys Lys Lys Xaa Glu Glu Glu Ala Ala Val Val
1               5                   10

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Glu Glu Ala Ala Val Val
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Ala Ala Val Val
1

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Ala Ala Ala Val Val Val
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic peptide

<400> SEQUENCE: 9

Lys Lys Ala Ala Val Val Lys
1               5

<210> SEQ ID NO 10
<211> LENGTH: 4
<212> TYPE: PRT
<213> ORGANISM: Artificial sequence
<220> FEATURE:
<223> OTHER INFORMATION: Synthetic peptide

<400> SEQUENCE: 10

Glu Glu Glu Glu
1
```